United States Patent
Li et al.

(10) Patent No.: US 9,062,055 B2
(45) Date of Patent: Jun. 23, 2015

(54) FUSED PYRROLE DERIVATIVES AS PI3K INHIBITORS

(75) Inventors: Yun-Long Li, Chadds Ford, PA (US); Andrew P. Combs, Kennett Square, PA (US)

(73) Assignee: Incyte Corporation, Wilmington, DE (US)

( * ) Notice: Subject to any disclaimer, the term of this patent is extended or adjusted under 35 U.S.C. 154(b) by 742 days.

(21) Appl. No.: 13/165,187

(22) Filed: Jun. 21, 2011

(65) Prior Publication Data

US 2011/0312979 A1 Dec. 22, 2011

Related U.S. Application Data

(60) Provisional application No. 61/356,976, filed on Jun. 21, 2010.

(51) Int. Cl.
*A61K 31/52* (2006.01)
*C07D 473/34* (2006.01)
*C07D 519/00* (2006.01)

(52) U.S. Cl.
CPC ............... *C07D 473/34* (2013.01); *A61K 31/52* (2013.01); *C07D 519/00* (2013.01)

(58) Field of Classification Search
USPC ........................................................ 544/277
See application file for complete search history.

(56) References Cited

U.S. PATENT DOCUMENTS

| | | | |
|---|---|---|---|
| 3,037,980 A | 6/1962 | Hitchings et al. |
| 3,169,967 A | 2/1965 | Schittler |
| 3,506,643 A | 4/1970 | Thiel et al. |
| 3,862,189 A | 1/1975 | Schwender et al. |
| 3,936,454 A | 2/1976 | Schwender et al. |
| 3,962,443 A | 6/1976 | Minami et al. |
| 4,482,629 A | 11/1984 | Nakagawa et al. |
| 4,840,951 A | 6/1989 | Iwasaki et al. |
| 4,845,020 A | 7/1989 | Itoh et al. |
| 4,861,701 A | 8/1989 | Burns et al. |
| 5,124,331 A | 6/1992 | Arita et al. |
| 5,208,250 A | 5/1993 | Cetenko et al. |
| 5,252,580 A | 10/1993 | Takahashi et al. |
| 5,294,620 A | 3/1994 | Ratcliffe et al. |
| 5,314,883 A | 5/1994 | Tanikawa et al. |
| 5,459,132 A | 10/1995 | Bru-Magniez et al. |
| 5,521,184 A | 5/1996 | Zimmermann |
| 5,646,153 A | 7/1997 | Spada et al. |
| 5,811,439 A | 9/1998 | Ogawa et al. |
| 5,866,702 A | 2/1999 | Mackman et al. |
| 6,028,076 A | 2/2000 | Hirota et al. |
| 6,342,501 B1 | 1/2002 | Townsend et al. |
| 6,376,501 B1 | 4/2002 | Isobe et al. |
| 6,392,047 B1 | 5/2002 | Geissler et al. |
| 6,479,487 B1 | 11/2002 | Dumont et al. |
| 6,630,496 B1 | 10/2003 | Seehra et al. |
| 6,734,187 B1 | 5/2004 | Tanaka et al. |
| 6,828,344 B1 | 12/2004 | Seehra et al. |
| 7,129,264 B2 | 10/2006 | Smallheer et al. |
| 7,495,002 B2 | 2/2009 | Langkopf et al. |
| 7,612,114 B2 | 11/2009 | Hamaoka et al. |
| 8,680,108 B2 | 3/2014 | Li et al. |
| 8,759,359 B2 | 6/2014 | Combs et al. |
| 2003/0008898 A1 | 1/2003 | Mahboobi et al. |
| 2003/0157052 A1 | 8/2003 | Choe et al. |
| 2004/0058930 A1 | 3/2004 | Belema et al. |
| 2004/0063658 A1 | 4/2004 | Roberts et al. |
| 2004/0067964 A1 | 4/2004 | Matsuoka et al. |
| 2004/0142941 A1 | 7/2004 | Gudmundsson et al. |
| 2004/0209866 A1 | 10/2004 | Wang et al. |
| 2004/0242615 A1 | 12/2004 | Yamamori et al. |
| 2005/0043328 A1 | 2/2005 | Dolezal |
| 2005/0059677 A1 | 3/2005 | Alberti et al. |
| 2005/0107343 A1 | 5/2005 | Kasibhatla et al. |

(Continued)

FOREIGN PATENT DOCUMENTS

| | | |
|---|---|---|
| AT | 388372 | 6/1989 |
| CA | 1066701 | 11/1979 |
| DE | 1770420 | 11/1971 |
| DE | 2139107 | 2/1973 |
| EP | 255085 | 2/1988 |
| EP | 464612 | 1/1992 |
| EP | 481614 | 4/1992 |
| EP | 1138328 | 11/2001 |
| EP | 1109805 | 12/2003 |
| EP | 1783114 | 5/2007 |
| EP | 1972631 | 9/2008 |
| EP | 2031037 | 3/2009 |

(Continued)

OTHER PUBLICATIONS

Cannon, J. G., Burger's Medicinal Chemistry and Drug Discovery, Fifth Edition, vol. I Principles and Practice, Wiley-Interscience 1995, Ch. 19, pp. 783-802, 784.*

(Continued)

*Primary Examiner* — Noble Jarrell
*Assistant Examiner* — John Mauro
(74) *Attorney, Agent, or Firm* — Fish & Richardson P.C.

(57) ABSTRACT

The present invention provides fused pyrrole derivatives of Formula I:

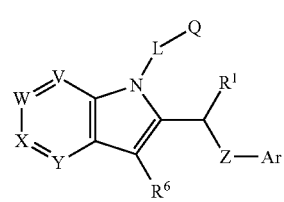

wherein V, W, X, Y, L, Q, Ar, Z, $R^1$ and $R^6$ are defined herein, that modulate the activity of phosphoinositide 3-kinases (PI3Ks) and are useful in the treatment of diseases related to the activity of PI3Ks including, for example, inflammatory disorders, immune-based disorders, cancer, and other diseases.

18 Claims, No Drawings

(56) References Cited

U.S. PATENT DOCUMENTS

| | | |
|---|---|---|
| 2005/0165030 A1 | 7/2005 | Liu et al. |
| 2005/0261317 A1 | 11/2005 | Sadhu et al. |
| 2005/0267110 A1 | 12/2005 | Hirano et al. |
| 2005/0282831 A1 | 12/2005 | Beauglehole et al. |
| 2006/0025383 A1 | 2/2006 | Wishart et al. |
| 2006/0052403 A1 | 3/2006 | Isobe et al. |
| 2006/0074102 A1 | 4/2006 | Cusack et al. |
| 2006/0084687 A1 | 4/2006 | Boyce et al. |
| 2006/0166925 A1 | 7/2006 | Dolezal et al. |
| 2006/0247245 A1 | 11/2006 | Xu |
| 2006/0293334 A1 | 12/2006 | Fuji et al. |
| 2007/0060577 A1 | 3/2007 | Player et al. |
| 2007/0066624 A1 | 3/2007 | Zhou et al. |
| 2007/0167443 A1 | 7/2007 | Melikian et al. |
| 2007/0191395 A1 | 8/2007 | Kawakami et al. |
| 2007/0225303 A1 | 9/2007 | Ogita et al. |
| 2007/0275984 A1 | 11/2007 | Imogai et al. |
| 2008/0004269 A1 | 1/2008 | Xu et al. |
| 2008/0009508 A1 | 1/2008 | Szucova et al. |
| 2008/0014227 A1 | 1/2008 | Popa et al. |
| 2008/0114007 A1 | 5/2008 | Player |
| 2008/0161332 A1 | 7/2008 | Bissantz et al. |
| 2008/0194616 A1 | 8/2008 | Liu et al. |
| 2008/0249155 A1 | 10/2008 | Gong et al. |
| 2008/0287469 A1 | 11/2008 | Diacovo et al. |
| 2008/0293739 A1 | 11/2008 | Trede |
| 2008/0306093 A1 | 12/2008 | Servant et al. |
| 2009/0023729 A1 | 1/2009 | Nakamura et al. |
| 2009/0047249 A1 | 2/2009 | Graupe et al. |
| 2009/0053192 A1 | 2/2009 | Millan et al. |
| 2009/0074884 A1 | 3/2009 | Chesney et al. |
| 2009/0118263 A1 | 5/2009 | Hashimoto |
| 2009/0137581 A1 | 5/2009 | Chen et al. |
| 2009/0163545 A1 | 6/2009 | Goldfarb |
| 2009/0170879 A1 | 7/2009 | Szucova et al. |
| 2009/0253717 A1 | 10/2009 | Brown et al. |
| 2009/0325930 A1 | 12/2009 | Hamaoka et al. |
| 2010/0010059 A1 | 1/2010 | Yeh et al. |
| 2010/0035756 A1 | 2/2010 | Luthy et al. |
| 2010/0105683 A1 | 4/2010 | Keegan et al. |
| 2010/0190819 A1 | 7/2010 | Kanner |
| 2010/0240537 A1 | 9/2010 | Spichal et al. |
| 2010/0256118 A1 | 10/2010 | Isobe et al. |
| 2010/0298351 A1 | 11/2010 | Konakanchi et al. |
| 2011/0015212 A1 | 1/2011 | Li et al. |
| 2011/0028715 A1 | 2/2011 | Isobe et al. |
| 2011/0098248 A1 | 4/2011 | Halcomb et al. |
| 2011/0105508 A1 | 5/2011 | Allen et al. |
| 2011/0183985 A1 | 7/2011 | Li et al. |
| 2011/0190319 A1 | 8/2011 | Combs |
| 2011/0224155 A1 | 9/2011 | Tachdjian et al. |
| 2011/0281884 A1 | 11/2011 | Combs et al. |
| 2012/0157430 A1 | 6/2012 | Li et al. |
| 2013/0029982 A1 | 1/2013 | Castro et al. |
| 2013/0059835 A1 | 3/2013 | Li et al. |
| 2013/0261101 A1 | 10/2013 | Combs et al. |
| 2014/0057912 A1 | 2/2014 | Combs et al. |
| 2014/0066448 A1 | 3/2014 | Combs et al. |
| 2014/0121222 A1 | 5/2014 | Li et al. |

FOREIGN PATENT DOCUMENTS

| | | |
|---|---|---|
| EP | 934307 | 4/2011 |
| GB | 1440478 | 6/1976 |
| GB | 1472342 | 5/1977 |
| JP | 50111080 | 9/1975 |
| JP | 53059663 | 5/1978 |
| JP | 53092767 | 8/1978 |
| JP | 56025234 | 6/1981 |
| JP | 56123981 | 9/1981 |
| JP | 58083698 | 5/1983 |
| JP | 62103640 | 5/1987 |
| JP | 62245252 | 10/1987 |
| JP | 1250316 | 10/1989 |
| JP | 4190232 | 7/1992 |
| JP | 9087282 | 3/1997 |
| JP | 9176116 | 7/1997 |
| JP | 10025294 | 1/1998 |
| JP | 10231297 | 9/1998 |
| JP | 2000080295 | 3/2000 |
| JP | 2000281654 | 10/2000 |
| JP | 2001151771 | 6/2001 |
| JP | 2005035924 | 2/2005 |
| JP | 2009080233 | 4/2009 |
| JP | 2009120686 | 6/2009 |
| JP | 2011136925 | 7/2011 |
| RU | 2233842 | 8/2004 |
| SU | 1712359 | 2/1992 |
| WO | WO 93/16076 | 8/1993 |
| WO | WO 93/25524 | 12/1993 |
| WO | WO 99/43651 | 9/1999 |
| WO | WO 99/43672 | 9/1999 |
| WO | WO 00/09495 | 2/2000 |
| WO | WO 00/44750 | 8/2000 |
| WO | WO 00/53595 | 9/2000 |
| WO | WO 01/14402 | 3/2001 |
| WO | WO 01/64639 | 9/2001 |
| WO | WO 01/64655 | 9/2001 |
| WO | WO 01/72709 | 10/2001 |
| WO | WO 02/00196 | 1/2002 |
| WO | WO 02/06477 | 1/2002 |
| WO | WO 02/24685 | 3/2002 |
| WO | WO 02/064599 | 8/2002 |
| WO | WO 02/066478 | 8/2002 |
| WO | WO 02/078701 | 10/2002 |
| WO | WO 03/020721 | 3/2003 |
| WO | WO 03/024967 | 3/2003 |
| WO | WO 03/029209 | 4/2003 |
| WO | WO 03/037347 | 5/2003 |
| WO | WO 03/044014 | 5/2003 |
| WO | WO 03/049678 | 6/2003 |
| WO | WO 03/050064 | 6/2003 |
| WO | WO 03/068750 | 8/2003 |
| WO | WO 03/074497 | 9/2003 |
| WO | WO 03/099771 | 12/2003 |
| WO | WO 2004/005281 | 1/2004 |
| WO | WO 2004/024693 | 3/2004 |
| WO | WO 2004/046120 | 6/2004 |
| WO | WO 2004/048365 | 6/2004 |
| WO | WO 2004/056786 | 7/2004 |
| WO | WO 2004/069256 | 8/2004 |
| WO | WO 2004/076455 | 9/2004 |
| WO | WO 2004/080980 | 9/2004 |
| WO | WO 2004/087704 | 10/2004 |
| WO | WO 2004/107863 | 12/2004 |
| WO | WO 2004/113335 | 12/2004 |
| WO | WO 2005/000309 | 1/2005 |
| WO | WO 2005/016528 | 2/2005 |
| WO | WO 2005/028444 | 3/2005 |
| WO | WO 2005/046578 | 5/2005 |
| WO | WO 2005/091857 | 10/2005 |
| WO | WO 2005/113556 | 12/2005 |
| WO | WO 2006/008523 | 1/2006 |
| WO | WO 2006/030031 | 3/2006 |
| WO | WO 2006/056399 | 6/2006 |
| WO | WO 2006/068760 | 6/2006 |
| WO | WO 2006/089106 | 8/2006 |
| WO | WO 2007/002701 | 1/2007 |
| WO | WO 2007/012724 | 2/2007 |
| WO | WO 2007/042806 | 4/2007 |
| WO | WO 2007/076092 | 7/2007 |
| WO | WO 2007/087548 | 8/2007 |
| WO | WO 2007/102392 | 9/2007 |
| WO | WO 2007/126841 | 11/2007 |
| WO | WO 2008/002490 | 1/2008 |
| WO | WO 2008/005303 | 1/2008 |
| WO | WO 2008/025821 | 3/2008 |
| WO | WO 2008/032033 | 3/2008 |
| WO | WO 2008/064018 | 5/2008 |
| WO | WO 2008/082490 | 7/2008 |
| WO | WO 2008/097991 | 8/2008 |
| WO | WO 2008/100867 | 8/2008 |
| WO | WO 2008/116129 | 9/2008 |

(56) References Cited

FOREIGN PATENT DOCUMENTS

| | | |
|---|---|---|
| WO | WO 2008/118454 | 10/2008 |
| WO | WO 2008/118468 | 10/2008 |
| WO | WO 2009/034386 | 3/2009 |
| WO | WO 2009/062118 | 5/2009 |
| WO | WO 2009/063235 | 5/2009 |
| WO | WO 2009/081105 | 7/2009 |
| WO | WO 2009/086123 | 7/2009 |
| WO | WO 2009/097446 | 8/2009 |
| WO | WO 2009/130560 | 10/2009 |
| WO | WO 2009/140215 | 11/2009 |
| WO | WO 2009/151972 | 12/2009 |
| WO | WO 2010/006234 | 1/2010 |
| WO | WO 2010/008739 | 1/2010 |
| WO | WO 2010/018458 | 2/2010 |
| WO | WO 2010/036380 | 4/2010 |
| WO | WO 2010/057048 | 5/2010 |
| WO | WO 2010/074588 | 7/2010 |
| WO | WO 2010/075068 | 7/2010 |
| WO | WO 2010/092340 | 8/2010 |
| WO | WO 2010/114900 | 10/2010 |
| WO | WO 2010/118367 | 10/2010 |
| WO | WO 2010/123931 | 10/2010 |
| WO | WO 2010/127208 | 11/2010 |
| WO | WO 2010/129816 | 11/2010 |
| WO | WO 2010/151735 | 12/2010 |
| WO | WO 2010/151740 | 12/2010 |
| WO | WO 2011/001052 | 1/2011 |
| WO | WO 2011/002708 | 1/2011 |
| WO | WO 2011/002817 | 1/2011 |
| WO | WO 2011/008302 | 1/2011 |
| WO | WO 2011/008487 | 1/2011 |
| WO | WO 2011/011550 | 1/2011 |
| WO | WO 2011/025889 | 3/2011 |
| WO | WO 2011/048082 | 4/2011 |
| WO | WO 2011/055215 | 5/2011 |
| WO | WO 2011/058111 | 5/2011 |
| WO | WO 2011/058113 | 5/2011 |
| WO | WO 2011/058474 | 5/2011 |
| WO | WO 2011/069294 | 6/2011 |
| WO | WO 2011/075628 | 6/2011 |
| WO | WO 2011/075630 | 6/2011 |
| WO | WO 2011/075643 | 6/2011 |
| WO | WO 2011/092198 | 8/2011 |
| WO | WO 2011/117711 | 9/2011 |
| WO | WO 2011/123751 | 10/2011 |
| WO | WO 2011/130342 | 10/2011 |
| WO | WO 2011/146882 | 11/2011 |
| WO | WO 2011/156759 | 12/2011 |
| WO | WO 2012/003262 | 1/2012 |
| WO | WO 2012/003271 | 1/2012 |
| WO | WO 2012/003274 | 1/2012 |
| WO | WO 2012/040634 | 3/2012 |
| WO | WO 2012/061696 | 5/2012 |
| WO | WO 2012/064973 | 5/2012 |
| WO | WO 2012/068343 | 5/2012 |
| WO | WO 2012/080729 | 6/2012 |
| WO | WO 2012/087784 | 6/2012 |
| WO | WO 2012/087881 | 6/2012 |
| WO | WO 2012/097000 | 7/2012 |
| WO | WO 2012/125629 | 9/2012 |
| WO | WO 2012/135009 | 10/2012 |
| WO | WO 2013/033569 | 3/2013 |
| WO | WO 2013/151930 | 10/2013 |

OTHER PUBLICATIONS

Schafer, S., Drug Discovery Today 2008, 13 (21/22), 913-916.*
Arthritis: MedlinePlus Medical Encyclopedia (2014), p. 1-5; accessed online Oct. 7, 2014; http://www.nlm.nih.gov/medlineplus/ency/article/001243.htm.*
Autoimmune disorders: MedlinePlus Medical Encyclopedia (2013), p. 1-4; accessed online Oct. 7, 2014; http://www.nlm.nih.gov/medlineplus/ency/article/000816.htm.*
Ball, J.,"PI3K inhibitors as potential therapeutics for autoimmune disease." Drug discovery today (2014) p. 1195-1199.*
Barber, D.F.,"PI3Kγ inhibition blocks glomerulonephritis and extends lifespan in a mouse model of systemic lupus." Nature medicine 11.9 (2005): 933-935.*
Devauchelle-Pensec, V.,Treatment of Primary Sjogren Syndrome With Rituximab (2014) Annals of Internal Medicine 160: 233-242.*
Merrill, J.T., "Efficacy and safety of rituximab in moderately-to-severely active systemic lupus erythematosus: The randomized, double-blind, phase ii/iii systemic lupus erythematosus evaluation of rituximab trial." Arthritis & Rheumatism 62.1 (2010): 222-233.*
"Adult Acute Myeloid Leukemia Treatment (PDQ®)—Patient Version, Last Modified Jul. 30, 2012," National Cancer Institute, [retrieved from the interne on Nov. 26, 2012] at http://www.cancer.gov/cancertopics/pdq/treatment/adultAML/Patient/page1, 5 pgs.
Ali, et al., "Essential role for the p110δ phosphoinositide 3-kinase in the allergic response," Nature. 2004, 431(7011):1007-11.
Allen, et al., "Synthesis of C-6 substituted pyrazolo[1,5-a]pyridines with potent activity against herpesviruses," Bioorganic & Medicinal Chemistry (2006), 14(4), 944-954.
Bader, et al., "Cancer-specific mutations in PIK3CA are oncogenic in vivo," Proc Natl Acad Sci U S A. 2006, 103(5):1475-9.
Barber, et al., "PI3Kγ inhibition blocks glomerulonephritis and extends lifespan in a mouse model of systemic lupus," Nat Med. 2005, 11(9):933-5.
Barragan et al., "Protein Kinases in the Regulation of Apoptosis in B-cell Chronic Lymphocytic Leukemia," Leukemia and Lymphoma, 2003, 44(11):1865-1870.
Belema, et al., "Synthesis and structure-activity relationship of imidazo(1,2-a)thieno(3,2-e)pyrazines as IKK-β inhibitors," Bioorganic & Medicinal Chemistry Letters (2007), 17(15), 4284-4289.
Benistant, et al., "A specific function for phosphatidylinositol 3-kinase α (p85α-p110α) in cell survival and for phosphatidylinositol 3-kinase β (p85α-p110β) in de novo DNA synthesis of human colon carcinoma cells," Oncogene, 2000, 19(44):5083-90.
Bennasar, et al., "Generation and Intermolecular Reactions of 2-Indolylacyl Radicals," Organic Letters (2001), 3(11), 1697-1700, CODEN: ORLEF7; ISSN: 1523-7060.
Berge et al., "Pharmaceutical Salts," J Pharma Sci, 1977, 66(1):1-19.
Bergman, et al., "Synthesis of indolocarbazole quinones; potent aryl hydrocarbon receptor ligands," Tetrahedron (2002), 58(7), 1443-1452.
Bhovi, et al., "1,3-dipolar cycloaddition reaction: Synthesis and antimicrobial activity of some new3-ethoxycarbonyl-5-methoxy-6-bromo-2-triazolylmethylindoles," Indian Journal of Heterocyclic Chemistry (2004), 14(1), 15-18 CODEN: IJCHEI; ISSN: 0971-1627.
Billottet, et al., "A selective inhibitor of the p110δ isoform of PI 3-kinase inhibits AML cell proliferation and survival and increases the cytotoic effects of VP16," Oncogene. 2006, 25(50):6648-59.
Biswas, et al., "Synthesis of a trifluoromethylindolocarbazole, novel cyclic 27- and 36-membered N-benzyltri- and -tetraindoles, and an N-benzyltetraindolyltrimethane," Monatshefte fuer Chemie (1999), 130(10), 1227-1239, CODEN: MOCMB7; ISSN: 0026-9247.
Blom et al., Preparative LC-MS Purification: Improved Compound Specific Method Optimization, J. Combi. Chem. 2004, 6(6), 874-883.
Boger, et al., "First and Second Generation Total Synthesis of the Teicoplanin Aglycon," JACS, 123(9), 1862-1871, 2001.
Bringmann, et al., "Novel concepts in directed biaryl synthesis. Part 65. Synthesis and structure of a novel twofold lactone-bridged ternaphthyl," Tetrahedron Letters (1998), 39(12), 1545-1548 CODEN: TELEAY; ISSN: 0040-4039.
Brock et al., "Roles of Gβγ in membrane recruitment and activation of p110γ/p101 phosphoinositide 3-kinaseγ," J Cell Biol., 2003, 160(1):89-99.
Brown, et al., "Small molecule inhibitors of IgE synthesis," Bioorganic & Medicinal Chemistry Letters (2006), 16(17), 4697-4699.
Camps, et al., "Blockade of PI3Kγ suppresses joint inflammation and damage in mouse models of rheumatoid arthritis," Nat Med. 2005, 11(9):936-43.
Cantley, "The Phosphoinositide 3-Kinase Pathway," Science, (2002) 296 (5573):1655-7.

(56) References Cited

OTHER PUBLICATIONS

Chai, et al., "Synthesis and in vitro anti-hepatitis B virus activities of some ethyl 6-bromo-5-hydroxy-1H-indole-3-carboxylates,"*Bioorganic & Medicinal Chemistry* (2006), 14(4), 911-917.
Clayton, et al., "A Crucial Role for the p110δ Subunit of Phosphatidylinositol 3-Kinase in B Cell Development and Activation," J Exp Med. 2002, 196(6):753-63.
DeBerardinis et al., "The Biology of Cancer: Metabolic Reprogramming Fuels Cell Growth and Proliferation," Cell Metabolism, Jan. 2008, 7:11-20.
Dolezal et al., "Preparation and biological activity of 6-benzylaminopurine derivatives in plants and human cancer cells," *Bioorganic & Medicinal Chemistry* (2006), 14(3), 875-884.
Dolezal et al., "Preparation, biological activity and endogenous occurrence of N6-benzyladenosines," *Bioorganic & Medicinal Chemistry* (2007), 15(11), 3737-3747.
Dorokhov, et al., "Synthesis of functionalized pyrimidine-4-thiones and pyrido[2,3-d]pyrimidin-5-one derivatives from aminals of monoacylketenes", Izvestiya Akademii Nauk, Seriya Khimicheskaya (1993), (11), 1932-7.
Doukas et al., "Aerosolized Phosphoinositide 3-Kinase γ/δ Inhibitor TG100-115 [3[2,4-Diamino-6-(3-hydroxyphenyl)pteridin-7-yl]phenol] as a Therapeutic Candidate for Asthma and Chronic Obstructive Pulmonary Disease," The Journal of Pharmacology and Experimental Therapeutics, 328(3):758-765, 2009.
Fadeyeva, et al., "Inhibitors of early virus-cell interaction stages among 3-ethoxycarbonyl-5-hydroxy-bromoindole derivatives," *Khimiko-Farmatsevticheskii Zhurnal* (1992), 26(9-10), 17-20 (with English abstract).
Flinn et al., "Preliminary evidence of clinical activity in a phase I study of CAL-101, a selective inhibitor of the p110δ isoform of phosphatidylinositol 3-kinase (PI3K), in patients with select hematologic malignancies," Journal of Clinical Oncology, (abstract), 27(15S):3543, 2009.
Floberg et al., "Extractive alkylation of 6-mercaptopurine and determination in plasma by gas chromatography-mass spectrometry," *Journal of Chromatography, Biomedical Applications,* (1981), 225(1), 73-81.
Fruman and Bismuth, "Fine Tuning the Immune Response with PI3K," *Immunological Revs.,* 2006, 228:253-272.
Gati et al., "(125I)Iodohydroxynitrobenzylthioinosine: a new high-affinity nucleoside transporter probe," *Biochemistry and Cell Biology* (1987), 65(5), 467-73.
Geng, et al., "Exploring 9-benzyl purines as inhibitors of glutamate racemase (MurI) in Gram-positive bacteria", Bioorganic & Medicinal Chemistry Letters (2008),18(15), 4368-4372.
Golantsov, et al., "Chirally N-substituted indole-2-carbaldehydes. Preparation and use in asymmetric synthesis," *Chemistry of Heterocyclic Compounds* (New York, NY, United States) (2005), 41(10), 1290-1299.
Granik, "Acetals of lactams and amides of acids. 40. Synthesis and hydrolytic splitting of mono- and bicyclic derivatives of 4-pyrimidinone", Khimiya Geterotsiklicheskikh Soedinenii (1984), (4),532-7 (with English abstract).
Greene and P. G. M. Wuts, Protective Groups in Organic Synthesis, 3rd Ed., Wiley & Sons, Inc., New York (1999).
Harris et al., "Alkyl 4-Chlorobenzoyloxycarbamates as Highly Effective Nitrogen Source Reagents for the Base-Free, Intermolecular Aminohydroxylation Reaction," J. Org. Chem., 76, 358-372, 2011.
Hauser et al., "B-Cell Depletion with Rituximab in Relapsing-Remitting Multiple Sclerosis," The New England Journal of Medicine, 358(7):676-688, 2008.
Hickey, et al., "BCR-ABL Regulates Phosphatidylinositol 3-Kinase-p110γ Transcription and Activation and is Required for Proliferation and Drug Resistance," J Biol Chem. 2006, 281(5):2441-50.
Hirose, et al., "Pyridone-carboxylic acids as antibacterial agents. I. Synthesis and antibacterial activity of 1-alkyl-1,4-dihydro-4-oxo-1,8- and -1,6-naphthyridine-3-carboxylic acids", Chemical & Pharmaceutical Bulletin (1982), 30(7), 2399-409.

Hirota, "Efficient synthesis of 2,9-disubstituted 8-hydroxyadenine derivatives", Organic & Biomolecular Chemistry (2003), 1(8), 1354-1365.
Huang et al., "Design and synthesis of a pyrido[2,3-d]pyrimidin-5-one class of anti-inflammatory FMS inhibitors,", *Bioorganic & Medicinal Chemistry Letters* (2008), 18(7), 2355-2361.
Huang et al., "Synthesis and bioassay of a fluorine-containing cytokinin, N6-pentafluoro-benzyladenosine," *Youji Huaxue* (1988), 8(2), 147-8 (with English abstract).
Ihle et al , "Inhibitors of phosphatidylinositol-3-kinase in cancer therapy", *Molecular Aspects of Medicine,* 31(2):135-144, 2010.
Irie, et al., "Discovery of selective and nonpeptidic cathepsin S inhibitors," *Bioorganic & Medicinal Chemistry Letters* (2008), 18(14), 3959-3962.
Isobe, et al., "Synthesis and Biological Evaluation of Novel 9-Substituted-8-Hydroxyadenine Derivatives as Potent Interferon Inducers", Journal of Medicinal Chemistry (2006), 49(6),2088-2095.
Itaya, et al., "Syntheses of the marine ascidian purine aplidiamine and its 9-β-D-ribofuranoside," *Tetrahedron Letters* (1998), 39(26), 4695-4696.
Itaya, et al., "Synthesis and structure of the marine ascidian 8-oxoadenine aplidiamine," *Chemical & Pharmaceutical Bulletin* (1999), 47(9), 1297-1300.
Jager et al., "Molecular recognition. II Discrimination of specific and non-specific intermolecular interactions by means of magnetic resonance spectroscopy," *Magnetic Resonance in Chemistry* (1998), 36(3), 205-210, CODEN: MRCHEG; ISSN: 0749-1581.
Jager, et al., "Molecular recognition analyzed by EPR, ENDOR, and NMR spectroscopy," *Angewandte Chemie,* International Edition in English (1996), 35(16), 1815-1818.
Jimenez, et al, "The p85 Regulator Subunit Controls Sequential Activation of Phosphoinositide 3-Kinase by Tyr Kinases and Ras," J Biol Chem., 2002, 277(44):41556-62.
Jou, et al., "Essential, Nonredundant Role for the Phosphoinositide 3-Kinase p110δ in Signaling by the B-Cell Receptor Complex," Mol Cell Biol. 2002, 22(24):8580-91.
Kang et al., "Aplidiamine, a unique zwitterionic benzyl hydroxyadenine from the Western Australian marine ascidian *Aplidiopsis* sp.," *Tetrahedron Letters* (1997), 38(6), 941-944.
Kang, et al., "Phosphtidylinositol 3-kinase mutations identified in human cancer are oncogenic," Proc Natl Acad Sci U S A. 2005, 102(3):802-7.
Kasibhatla, "Rationally Designed High-Affinity 2-Amino-6-halopurine Heat Shock Protein 90 Inhibitors That Exhibit Potent Antitumor Activity",Journal of Medicinal Chemistry (2007), 50(12),2767-2778.
Katritzky, et al., "Facile Synthesis of 2-Substituted Indoles and Indolo[3,2-b]carbazoles from 2-(Benzotriazol-1-ylmethyl)indole," *Journal of Organic Chemistry* (1995), 60(11), 3401-4.
Kim, et al., "A new structural class of S-adenosylhomocysteine hydrolase inhibitors", Bioorganic & Medicinal Chemistry (2009), 17(18), 6707-6714.
Kim, et al., "Synthesis and evaluation of antitumor activity of novel 1,4-naphthoquinone derivatives," *Archives of Pharmacal Research* (2006), 29(2), 123-130 CODEN: APHRDQ; ISSN: 0253-6269.
Knobbe, et al., "Genetic alteration and expression of the phosphoinositol-3-kinase/Akt pathway genes *PIK3CA* and *PIKE* in human glioblastomas," Neuropathol Appl Neurobiol. 2005, 31(5):486-90.
Kolasa, et al., "Synthesis of indolylalkoxyiminoalkylcarboxylates as leukotriene biosynthesis inhibitors," *Bioorganic & Medicinal Chemistry* (1997), 5(3), 507-514.
Kong and Yamori, "Advances in Development of Phosphatidylinositol 3-Kinase Inhibitors," Current Medicinal Chemistry, 16:2839-2854, 2009.
Kuduk et al., "Heterocyclic fused pyridone carboxylic acid M1 positive allosteric modulators," *Bioorganic & Medicinal Chemistry Letters* (2010), 20(8), 2533-2537.
Kung et al., "Characterization of a Murine Model of Allergic Pulmonary Inflammation," Int. Arch. Allergy Immunol , (abstract), 105(1):83-90, 1994.

(56) References Cited

OTHER PUBLICATIONS

Kurimoto, et al., "Synthesis and Biological Evaluation of 8-Oxoadenine Derivatives as Toll-like Receptor 7 Agonists Introducing the Antedrug Concept", *Journal of Medicinal Chemistry* (2010), 53(7),2964-2972.
Kutney, et al., "Dihydropyridines in synthesis and biosynthesis. IV. Dehydrosecodine, in vitro precursor of indole alkaloids," *Canadian Journal of Chemistry* (1982), 60(11), 1269-78.
Lee, et al , "Inhibition of phosphoinositide 3-kinase δ attenuates allergic airway inflammation and hyperresponsiveness in murine asthma model," FASEB J. 2006, 20(3):455-65.
Li et al., "Design, synthesis and antitumor activities of novel 4-anilino-5H-pyridazino[4,5-b]indoles," *Zhongnan Yaoxue* (2008), 6(2), 144-148, CODEN: ZYHAC6; ISSN: 1672-2981, Publisher: Zhongnan Yaoxue Zazhishe (with English abstract within the article).
Li et al., "Synthesis and antitumor activities of novel 1-anilino 5H-pyridazino[4,5-b]indoles," *Zhongguo Yaowu Huaxue Zazhi* (2007), 17(6), 339-343, CODEN: ZYHZEF; ISSN: 1005-0108 (with English abstract within the article).
Li, et al., "Synthesis and anti-tumor activities of a novel series of tricyclic 1-anilino-5H-pyridazino[4,5-b]indoles," *Archiv der Pharmazie* (Weinheim, Germany) (2007), 340(8), 424-428, CODEN: ARPMAS; ISSN: 0365-6233.
Li, et al., "Optimization of the heterocyclic core of the quinazolinone-derived CXCR3 antagonists," *Bioorganic & Medicinal Chemistry Letters* (2008), 18(2), 688-693.
Lindsay, et al., "SmI2-Promoted Radical Addition Reactions with N-(2-Indolylacyl)oxazolidinones: Synthesis of Bisindole Compounds," *Journal of Organic Chemistry* (2007), 72(11), 4181-4188, CODEN: JOCEAH; ISSN: 0022-3263.
Link, J. T., "The intramolecular Heck reaction," *Organic Reactions* (Hoboken, NJ, United States) (2002), 60, No pp. given CODEN: ORHNBA URL: http://www3.interscience.wiley.com/cgi-bin/mrwhome/107610747/HOME.
Lucas, et al., "Rauwolfia alkaloids. XXXI. The synthesis and activity of some reserpine analogs," *Journal of the American Chemical Society* (1959), 81, 1928-32.
Ma, et al., "Two new constituents from *Artemisia capillaris* Thunb", Molecules (2008), 13(2), 267-271.
Ma, et al., "Bromophenols Coupled with Nucleoside Bases and Brominated Tetrahydroisoquinolines from the Red Alga *Rhodomela confervoides*", Journal of Natural Products (2007), 70(3), 337-341.
Mahboobi, et al., "Bis(1H-2-indolyl)methanones as a Novel Class of Inhibitors of the Platelet-Derived Growth Factor Receptor Kinase," Journal of Medicinal Chemistry (2002), 45(5):1002-1018.
Matsumoto, et al., "Pyrido[2,3-d]pyrimidine antibacterial agents. 3. 8-Alkyl- and 8-vinyl-5,8-dihydro-5-oxo-2-(1-piperazinyl)pyrido[2,3-d]pyrimidine-6-carboxylic acids and their derivatives", *J Medicinal Chem* (1975), 18(1), 74-9.
McLean, et al., "Discovery of covalent inhibitors for MIF tautomerase via cocrystal structures with phantom hits from virtual screening ," *Bioorganic & Medicinal Chemistry Letters* (2009), 19(23), 6717-6720.
McMahon, G., "VEGF Receptor Signaling in Tumor Angiogenesis," The Oncologist, 5(1):3-10, 2000.
Meade, et al., "Anxiolytic activity of analogs of 4-benzylamino-2-methyl-7H-pyrrolo[2,3-d]pyrimidines," *European Journal of Medicinal Chemistry* (1998), 33(5), 363-374.
Meijer et al., "Treatment of primary Sjögren syndrome with rituximab: extended follow-up, safety and efficacy of retreatment," Ann. Rheum. Dis., 68(2):284-285, 2009.
Miki, et al., "Reaction of 1-benzylindole-2,3-dicarboxylic anhydride with 3-bromo-4-lithiopyridine: formal synthesis of ellipticine," *Heterocycles* (1998), 48(8), 1593-1597.
Miki, et al., "Synthesis of caulersin and its isomers by reaction of indole-2,3-dicarboxylic anhydrides with methyl indoleacetates," *Tetrahedron Letters* (2006), 47(29), 5215-5218, CODEN: TELEAY; ISSN: 0040-4039.
Miki, et al., "Synthesis of ellipticine by reaction of 1-(4-methoxybenzyl)indole-2,3-dicarboxylic anhydride with (3-bromo-4-pyridyl)triisopropoxytitanium," *Journal of the Chemical Society, Perkin Transactions* 1 (2001), (18), 2213-2216.
Miki, et al., "Reaction of indole-2,3-dicarboxylic anhydride with (3-bromo-4-pyridyl)triisopropoxytitanium: synthesis of ellipticine," *Tetrahedron Letters* (1996), 37(43), 77537754.
Mishra et al., "Decanuclear Copper Framework Supported by a Tripodal Adenine Ligand," *Inorganic Chemistry* (Washington, DC, United States), (2010), 49(8), 3691-3693.
Mizoguchi, et al., "Genetic Alterations of Phosphoinositide 3-kinase Subunit Genes in Human Glioblastomas," Brain Pathol. 2004, 14(4):372-7.
Moffett, "Antiulcer agents. p-Aminobenzamido aromatic compounds", Journal of Medicinal Chemistry (1971), 14(10), 963-8.
Mohammadizadeh, et al., "A novel and expedient synthesis of 7-pyrimidinylpyrimido[4,5-d]pyrimidinones," *Helvetica Chimica Acta* (2010), 93(1), 153-157.
Morrison, et al., "Pyrimido[4,5-c]pyridazines. 1. Cyclizations with α-keto esters", *Journal of Organic Chemistry* (1978), 43(25), 4844-9.
Mukhopadhyay, et al., "An ionic liquid {[secbmim]+ Br-} as a "dual reagent catalyst" for the multicomponent synthesis of (quinolinyl- and isoquinolinyl-amino) alkylnaphthols, their bis-analogs and a facile route to naphthoxazines," ARKIVOC (Gainesville, FL, United States) (2010), (10), 291-304.
Musmuca, et al., "Small-Molecule Interferon Inducers. Toward the Comprehension of the Molecular Determinants through Ligand-Based Approaches", Journal of Chemical Information and Modeling (2009),49(7), 1777-1786.
Najiwara, et al., Generation and behavior of naphthoyloxyl radicals in photocleavage of 1-(naphthoyloxy)-2-pyridones, *Chemistry Letters* (2001), (10), 1064-1065.
Najiwara, et al., "Behavior of naphthoyloxyl and methoxynaphthoyloxyl radicals generated from the photocleavage of dinaphthoyl peroxides and 1-(naphthoyloxy)-2-pyridones," *Bulletin of the Chemical Society of Japan* (2003), 76(3), 575-585.
Nettekoven, M., "A combinatorial approach towards 2-acyl-3-amino-indole derivatives," *Tetrahedron Letters* (2000), 41(43), 8251-8254.
Norman, P., "Selective PI3Kδ inhibitors , a review of the patent literature", Expert Opinion on Therapeutic Patents, Informa Healthcare, 21(11):1773-1790, 2011.
Oki, et al., "Reactivities of Stable Rotamers. XLII. Generation and Fates of Rotameric [1-(9-Fluorenyl)-2-naphthyl]methyl Radicals," *Bulletin of the Chemical Society of Japan* (1999), 72(10), 2327-2336.
Okkenhaug, et al., "Impaired B and T Cell Antigen Receptor Signaling in p110δ PI 3-Kinase Mutant Mice," Science, 2002, 297(5583):1031-4).
Park et al., "Phosphoinositide 3-kinase δ inhibitor as a novel therapeutic agent in asthma," Respirology, 13:764-771, 2008.
Phillips, et al., "The reaction of anils with 8-quinolinol," *Journal of Organic Chemistry* (1954), 19, 907-9 CODEN: JOCEAH; ISSN: 0022-3263.
Pinedo and Slamon, "Translational Research: The Role of VEGF in Tumor Angiogenesis," The Oncologist, 5(1):1-2, 2000.
Platts, et al., "A concise synthesis of HIV integrase inhibitors bearing the dipyridone acid motif," *Tetrahedron Letters* (2011), 52(4), 512-514.
Portnaya, et al., "Azomethine dyes. IV. Indoaniline dyes derived from heterocyclic N-substituted 1-hydroxy-2-naphthamides," *Ts. Vses. Nauchn.-Issled. Kinofotoinst.* (1960), (No. 40), 106-18 (with English abstract).
Prezent, et al., STN Abstract, Accession No. 2004:358794, "Boron chelates as intermediates in the synthesis of new functionalized pyridines and pyrimidines from α,α-dioxoketene aminals," *Boron Chemistry at the Beginning of the 21st Century*, [Proceedings of the International Conference on the Chemistry of Boron], 11th, Moscow, Russian Federation, Jul. 28-Aug. 1, 2002 (2003), Meeting Date 2002, 91-93. Editor(s): Bubnov, Yu. N. A. N. Nesmeyanov Institute of Organoelement Compounds, Russian Academy of Sciences: Moscow, Russia.
Puri and Gold, "Selective inhibitors of phosphoinositide 3-kinase delta: modulators of B-cell function with potential for treating

(56) References Cited

OTHER PUBLICATIONS autoimmune inflammatory diseases and B-cell malignancies," Frontiers in Immunology, 3(256):1-16, 2012.
Ramos-Casals et al., "Rituximab in systemic lupus erythematosus; A systematic review of off-label use in 188 cases," Lupus, 18:767-776, 2009.
Randis, et al., "Role of PI3Kδ and PI3Kγ in inflammatory arthritis and tissue localization of neutrophils," Eur. J. Immunol , 2008, 38(5):1215-24.
Reich, et al., "Preparation of a,b-unsaturated carbonyl compounds and nitriles by selenoxide elimination ," *Organic Reactions* (Hoboken, NJ, United States) (1993), 44, No pp. given.
Remington's Pharmaceutical Sciences, 17th ed., Mack Publishing Company, Easton, Pa., 1985, p. 1418.
Ringshausen et al., "Constitutively Actived phosphatidylinositol-3-kinase (PI-3K) is involved in the defect of apoptosis is B-CLL: assocaite with protein kinase C delta," Blood, 2002, 100:3741-3748.
Roxas-Duncan, et al., "Identification and biochemical characterization of small-molecule inhibitors of *Clostridium botulinum* neurotoxin serotype A," *Antimicrobial Agents and Chemotherapy* (2009), 53(8), 3478-3486.
Sahoo, et al., "Antispasmodic compounds. IV," Journal of the Indian Chemical Society (1959), 36, 421-4.
Sako, M., "Product class 19: pyridopyrimidines," *Science of Synthesis* (2004), 16, 1155-1267.
Samuels, et al., "High Frequency of Mutations of the PIK3CA Gene in Human Cancers," Science, 2004, 304(5670):554.
Samuels and Ericson, "Oncogenic PI3K and its role in cancer," Curr Opin Oncol., 2006, 18(1):77-82.
Sasaki, et al., "Function of PI3Kγ in Thymocyte Development, T Cell Activation, and Neutrophil Migration," Science, 2000, 287(5455):1040-6.
Saxena, et al., "Pharmacophore-based virtual screening and docking studies on Hsp90 inhibitors", SAR and QSAR in Environmental Research (2010), 21(5-6), 445-462.
Schell, et al., "Versatile Solid-Phase Synthesis of Trisubstituted 1H-Pyrido[2,3-d]pyrimidin-4-ones and Related Heterocycles," *Journal of Combinatorial Chemistry* (2005), 7(1), 96-98.
Sen, et al., "Reaction of aldehydes and amines with 8-hydroxyquinaldine and 8-quinolinol. II," *Journal of the Indian Chemical Society* (1960), 37, 640-2.
Shi, et al., "Synthesis and preliminary cytotoxic evaluation of substituted indoles as potential anticancer agents," *Chinese Chemical Letters* (2007), 18(8), 899-901, CODEN: CCLEE7; ISSN: 1001-8417.
Shuttleworth et al., "Progress in the Preclinical Discovery and Clinical Development of Class 1 and Dual Class I/IV Phosphoinositide 3-Kinase (PI3K) Inhibitors", Current Medicinal Chemistry, 18(1):2686-2714, 2011.
Singh et al., "Application of Nazarov cyclization to access [6-5-6] and [6-5-5]tricyclic core embedded new heterocycles: an easy entry to structures related to Taiwaniaquinoids," *Organic & Biomolecular Chemistry* (2009), 7(9), 1858-1867, CODEN: OBCRAK; ISSN: 1477-0520.
Steliou, et al., "Does diatomic sulfur(S2) react as a free species?", *Journal of the American Chemical Society* (1992), 114(4), 1456-62.
Stüve et al., "Long-term B-Lymphocyte Depletion With Rituximab in Patients With Relapsing-Remitting Multiple Sclerosis," Arch. Neurol., 66(2):259-261, 2009.
Sujobert, et al., "Essential role for the p110δ isoform in phosphoinositide 3-kinase activation and cell proliferation in acute myeloid leukemia," Blood, 2005, 106(3):1063-6.
Szuecova, et al., "Synthesis, characterization and biological activity of ring-substituted 6-benzylamino-9-tetrahydropyran-2-yl and 9-tetrahydrofuran-2-ylpurine derivatives," *Bioorganic & Medicinal Chemistry* (2009), 17(5), 1938-1947.
Thomas, et al., "Airway inflammation: chemokine-induced neutrophilia and the class I phosphoinositide 3-kinases," Eur J Immunol 2005, 35(4):1283-91.
Travnickek, et al., "2-Chloro-6-[(4-hydroxy-3,5-dimethoxybenzyl)amino]-9-isopropylpurine," *Acta Crystallographica*, Section E: Structure Reports Online (2007), E63(2), o728-o730 CODEN: ACSEBH; ISSN: 1600-5368 URL: http://journals.iucr.org/e/issues/2007/02/00/1h2285/1h2285.pdf.
Uddin et al., "Role of phosphatidylinositol 3'-kinase/Akt pathway in diffuse large B-cell lymphomas survival," Blood, 2006, 108:4178-4186.
Vanhaesebroeck et al., "Signalling by PI3K isoforms: insights from gene-targeted mice," Trends Biochem Sci., 2005, 30(4):194-204.
Vasil'ev, et al, "Chelate synthesis of 1-alkyl-5-(trifluoromethyl)-1,6-naphthyridin-4(1H)-ones", Izvestiya Akademii Nauk, Seriya Khimicheskaya (1994),(8), 1510-11 (with English abstract).
Venet et al., "Lymphocytes in the Development of Lung Inflammation: A role of Regulatory CD4+ T Cells in Indirect Pulmonary Lung Injury," *J Immunol.*, 2009, 183:6472-3480.
Xu et al., "Activation of the PI3K/ACT/mTOR pathway in diffuse large B cell lymphoma: clinical significance and inhibitory effect of rituximab," Ann Hematol., 2013, 92:1351-1358.
Yaguchi et al., "Antitumor Activity of ZSTK474, a new Phosphatidinylinositol 3-Kinase Inhibitor," *J Natl. Cancer Inst.*, 2006, 98(8):545-556.
Yahyazadeh, et al., "Synthesis of 9-benzyl-6-aminopurines from 5-amino-1-benzyl-4-cyanoimidazoles", Bulletin of the Korean Chemical Society (2003), 24(12), 1723-1724.
Yahay-Zadeh, "Synthesis of 9-Aryl-6-aminopurines from 5-Amino-1-aryl-1H-imidazole-4-carbonitriles", Russian Journal of Organic Chemistry (Translation of Zhurnal Organicheskoi Khimii) (2003), 39(11),1649-1651.
Yanni, et al., "Synthesis and biological activity of some 7-substituted aminomethyl-8-hydroxyquinoline-5-sulfonic acids," *Indian Journal of Chemistry, Section B: Organic Chemistry Including Medicinal Chemistry* (1982), 21B(7), 705-6.
Yanni, A. S., "Synthesis of some new 5-iodo-7-substituted-aminomethyl-8-hydroxyquinoline," *Revue Roumaine de Chimie* (1994), 39(7), 833-6 CODEN: RRCHAX; ISSN: 0035-3930.
Yoo, et al., "Synthesis and evaluation of antitumor activity of novel 2-[N-methyl-N-(4-methyl-1,3-benzothiazol-2-yl)aminomethyl]-5,8-diacyloxy-1,4-naphthoquinones," *Archives of Pharmacal Research* (2008), 31(2), 142-147 CODEN: APHRDQ; ISSN: 0253-6269.
Yoshida, et al., "MexAB-OprM specific efflux pump inhibitors in *Pseudomonas aeruginosa*. Part 5: Carbon-substituted analogues at the C-2 position," *Bioorganic & Medicinal Chemistry* (2006), 14(6), 1993-2004.
Zhang et al., "Advances in preclinical small molecules for the treatment of NSCLC", Expert Opinion on Therapeutic Patents, 19(6):731-751, 2009.
Zhao, et al., "Synthesis and in vitro anti-hepatitis B virus activities of some ethyl 5-hydroxy-1H-indole-3-carboxylates," *Bioorganic & Medicinal Chemistry* (2006), 14(8), 2552-2558.
International Preliminary Report on Patentability dated Dec. 28, 2012 for International Appln. No. PCT/US2011/041202 (8 pgs.).
International Preliminary Report on Patentability dated Jul. 4, 2013 for International Appln. No. PCT/US2011/065743 (8 pgs).
International Preliminary Report on Patentability dated Jun. 19, 2012 for International Appln. No. PCT/US2010/061023 (6 pgs.).
International Preliminary Report on Patentability dated Jun. 19, 2012 for International Appln. No. PCT/US2010/060980 (8 pgs.).
International Preliminary Report on Patentability dated Oct. 16, 2012 for International Appln. No. PCT/US2011/032213 (6 pgs.).
International Preliminary Report on Patentability for PCT/US2010/040150 dated Jul. 5, 2011 (24pgs.).
International Preliminary Report on Patentability for PCT/US2012/030310 dated Oct. 1, 2013 (7pgs.).
International Search Report dated Jul. 11, 2013 for International Appln. No. PCT/US2013/034803 (15 pgs.).
International Search Report dated Dec. 21, 2012 for International Appln. No. PCT/US2012/053398 (11 pgs.).
International Search Report dated Feb. 28, 2012 for International Appln. No. PCT/US2011/065743 (13 pgs.).
International Search Report dated May 11, 2012 for International Appln. No. PCT/US2012/030310 (11 pgs.).

(56) References Cited

OTHER PUBLICATIONS

International Search Report dated May 31, 2012 for International Appln. No. PCT/US2012/028915 (11 pgs.).
International Search Report dated Sep. 23, 2011 for International Appln. No. PCT/US2011/041202 (12 pgs.).
International Search Report for PCT/US2010/040150 dated Nov. 8, 2010 (19 pgs.).
International Search Report for PCT/US2010/060980 dated Mar. 15, 2011 (12 pgs.).
International Search Report for PCT/US2010/061023 dated Feb. 16, 2011 (10 pgs.).
International Search Report for PCT/US2011/032213 dated Jun. 14, 2011 (11 pgs.).
STN Search Report, conducted Dec. 1, 2010, 132 pages.
STN Search Report, conducted Dec. 16, 2009, 72 pages.
STN Search Report, conducted prior to Jun. 21, 2011, 224 pages.
STN Search Report, conducted Apr. 5, 2010, 513 pages.
STN Search Report, conducted Apr. 24, 2009, 43 pages.
STN Search Report, conducted Dec. 7, 2010, 213 pages.
STN Search Report, conducted Aug. 29, 2011, 181 pages.
STN Search Report, conducted May 27, 2009, 2 pages.
STN Search Report, conducted May 28, 2009, 81 pages.
STN Search Report, conducted Apr. 2, 2010, 141 pages.
STN Search Report, conducted Aug. 30, 2011, 61 pages.
"Angiogenesis" Merriam-Webster.com. Merriam-Webster, n.d. Web Jun. 16, 2014, www.merriamwebster.com/dictionary/angiogenesis, 3 pages.
Baek et al., "Complete remission induced by rituximab in refractory, seronegative, muscle-specific, kinase-positive myasthenia gravis," J Neurol Neurosurg Psychiatry, 2007, 78(7):771.
Collins et al., "Rituximab treatment of fibrillary glomerulonephritis," Am J Kidney Dis., 2008, 52(6):1158-62.
Crabbe, "The PI3K inhibitor arsenal: choose your weapon!" Trends Biochem Sci., 2007, 32(10):450-56.
Lipsky, "Systemic lupus erythematosus: an autoimmune disease of B cell hyperactivity," Nat Immunol., 2001, 2(9):764-6.
Liu et al., "Inhibition of the mitotic kinesin Eg5 up-regulates Hsp70 through the phosphatidylinositol 3-kinase/Akt pathway in multiple myeloma cells," J Biol Chem., 2006, 281(26):18090-18097.
MedicineNet.com' [online]. "Definition of Cancer," Sep. 18, 2004, retrieved on Sep. 16, 2005. Retrieved from the Internet: http://www.medterms.com, 1 page.
Segarra et al., "Successful treatment of membranous glomerulonephritis with rituximab in calcineurin inhibitor-dependent patients," Clin J Am Soc Nephrol., 2009, 4(6):1083-8.
WebMD. Lung Disease & Respiratory Health Center: Lung Disease Overview, May 23, 2014, www.webmd.com/lung/lung-diseases-overview, 3 pages.
WebMD. Lung Disease & Respiratory Health Center: ARDS, May 21, 2014, www.webmd.com/lung/ardsacuterespiratory-distress-syndrome?page=2, 4 pages.
WebMD. Osteoarthritis Health Center: Osteroarthritis-prevention, Apr. 9, 2013, www.webmd.com/osteoarthritis/tc/osteoarthritis-prevention, 2 pages.
WebMD. Psoriasis Health Center: Psoriasis-prevention, Jan. 9, 2012, www.webmd.com/skinproblemsandtreatments/psoriasis/psoriasis-prevention, 1 page.
WebMD. Bladder Cancer Health Center: Bladder Cancer-Prevention, Apr. 30, 2013, www.webmd.com/cancer/bladder-cancer/bladder-cancer-prevention, 1 page.
WebMD. Arthritis Health Center: What is Inflammation? Jul. 6, 2012, www.webmd.com/arthritis/about-inflammation?page=2, 4 pages.
International Preliminary Report on Patentability for PCT/US2012/028915 dated Sep. 17, 2013 (6 pgs.).
International Preliminary Report on Patentability for PCT/US2012/053398, issued Mar. 4, 2014 (6 pgs.).
Office Action in CO Application No. 11-179.464, received on Mar. 14, 2014, 17 pages.

* cited by examiner

FUSED PYRROLE DERIVATIVES AS PI3K INHIBITORS

This application claims the benefit of priority of U.S. Provisional Application No. 61/356,976, filed Jun. 21, 2010, which is incorporated herein by reference in its entirety.

TECHNICAL FIELD

The present invention provides fused pyrrole derivatives that modulate the activity of phosphoinositide 3-kinases (PI3Ks) and are useful in the treatment of diseases related to the activity of PI3Ks including, for example, inflammatory disorders, immune-based disorders, cancer, and other diseases.

BACKGROUND

The phosphoinositide 3-kinases (PI3Ks) belong to a large family of lipid signaling kinases that phosphorylate phosphoinositides at the D3 position of the inositol ring (Cantley, Science, 2002, 296(5573):1655-7). PI3Ks are divided into three classes (class I, II, and III) according to their structure, regulation and substrate specificity. Class I PI3Ks, which include PI3Kα, PI3Kβ, PI3Kγ, and PI3Kδ, are a family of dual specificity lipid and protein kinases that catalyze the phosphorylation of phosphatidylinosito-4,5-bisphosphate ($PIP_2$) giving rise to phosphatidylinosito-3,4,5-trisphosphate ($PIP_3$). $PIP_3$ functions as a second messenger that controls a number of cellular processes, including growth, survival, adhesion and migration. All four class I PI3K isoforms exist as heterodimers composed of a catalytic subunit (p110) and a tightly associated regulatory subunit that controls their expression, activation, and subcellular localization. PI3Kα, PI3Kβ, and PI3Kδ associate with a regulatory subunit known as p85 and are activated by growth factors and cytokines through a tyrosine kinase-dependent mechanism (Jimenez, et al., J Biol Chem., 2002, 277(44):41556-62) whereas PI3Kγ associates with two regulatory subunits (p101 and p84) and its activation is driven by the activation of G-protein-coupled receptors (Brock, et al., J Cell Biol., 2003, 160(1):89-99). PI3Kα and PI3Kβ are ubiquitously expressed. In contrast, PI3Kγ and PI3Kδ are predominantly expressed in leukocytes (Vanhaesebroeck, et al., Trends Biochem Sci., 2005, 30(4):194-204).

The differential tissue distribution of the PI3K isoforms factors in their distinct biological functions. Genetic ablation of either PI3Kα or PI3Kβ results in embryonic lethality, indicating that PI3Kα and PI3Kβ have essential and non-redundant functions, at least during development (Vanhaesebroeck, et al., 2005). In contrast, mice which lack PI3Kγ and PI3Kδ are viable, fertile and have a normal life span although they show an altered immune system. PI3Kγ deficiency leads to impaired recruitment of macrophages and neutrophils to sites of inflammation as well as impaired T cell activation (Sasaki, et al., Science, 2000, 287(5455):1040-6). PI3Kδ-mutant mice have specific defects in B cell signaling that lead to impaired B cell development and reduced antibody responses after antigen stimulation (Clayton, et al., J Exp Med. 2002, 196(6):753-63; Jou, et al., Mol Cell Biol. 2002, 22(24):8580-91; Okkenhaug, et al., Science, 2002, 297(5583):1031-4).

The phenotypes of the PI3Kγ and PI3Kδ-mutant mice suggest that these enzymes may play a role in inflammation and other immune-based diseases and this is borne out in preclinical models. PI3Kγ-mutant mice are largely protected from disease in mouse models of rheumatoid arthritis (RA) and asthma (Camps, et al., Nat Med. 2005, 11(9):936-43; Thomas, et al., Eur J Immunol. 2005, 35(4):1283-91). In addition, treatment of wild-type mice with a selective inhibitor of PI3Kγ was shown to reduce glomerulonephritis and prolong survival in the MRL-1pr model of systemic lupus nephritis (SLE) and to suppress joint inflammation and damage in models of RA (Barber, et al., Nat Med. 2005, 11(9):933-5; Camps, et al., 2005). Similarly, both PI3Kδ-mutant mice and wild-type mice treated with a selective inhibitor of PI3Kδ have been shown to have attenuated allergic airway inflammation and hyper-responsiveness in a mouse model of asthma (Ali, et al., Nature. 2004, 431(7011):1007-11; Lee, et al., FASEB J. 2006, 20(3):455-65) and to have attenuated disease in a model of RA (Randis, et al., Eur. J. Immunol., 2008, 38(5):1215-24).

In addition to their potential role in inflammatory diseases, all four class I PI3K isoforms may play a role in cancer. The gene encoding p110α is mutated frequently in common cancers, including breast, prostate, colon and endometrial (Samuels, et al., Science, 2004, 304(5670):554; Samuels, et al., Curr Opin Oncol. 2006, 18(1):77-82). Eighty percent of these mutations are represented by one of three amino acid substitutions in the helical or kinase domains of the enzyme and lead to a significant upregulation of kinase activity resulting in oncogenic transformation in cell culture and in animal models (Kang, et al., Proc Natl Acad Sci USA. 2005, 102(3):802-7; Bader, et al., Proc Natl Acad Sci USA. 2006, 103(5):1475-9). No such mutations have been identified in the other PI3K isoforms although there is evidence that they can contribute to the development and progression of malignancies. Consistent overexpression of PI3Kδ is observed in acute myeloblastic leukemia (Sujobert, et al., Blood, 2005, 106(3):1063-6) and inhibitors of PI3Kδ can prevent the growth of leukemic cells (Billottet, et al., Oncogene. 2006, 25(50):6648-59). Elevated expression of PI3Kγ is seen in chronic myeloid leukemia (Hickey, et al., J Biol Chem. 2006, 281(5):2441-50). Alterations in expression of PI3Kβ, PI3Kγ and PI3Kδ have also been observed in cancers of the brain, colon and bladder (Benistant, et al., Oncogene, 2000, 19(44):5083-90; Mizoguchi, et al., Brain Pathol. 2004, 14(4):372-7; Knobbe, et al., Neuropathol Appl Neurobiol. 2005, 31(5):486-90). Further, these isoforms have all been shown to be oncogenic in cell culture (Kang, et al., 2006).

Thus, new or improved agents which inhibit kinases such as PI3K are continually needed for developing new and more effective pharmaceuticals that are aimed at augmentation or suppression of the immune and inflammatory pathways (such as immunosuppressive agents for organ transplants), as well as agents for the prevention and treatment of autoimmune diseases (e.g., multiple sclerosis, rheumatoid arthritis, asthma, type I diabetes, inflammatory bowel disease, Crohn's disease, autoimmune thyroid disorders, Alzheimer's disease, nephritis), diseases involving a hyperactive inflammatory response (e.g., eczema), allergies, lung diseases, cancer (e.g., prostate, breast, leukemia, multiple myeloma), and some immune reactions (e.g., skin rash or contact dermatitis or diarrhea) caused by other therapeutics. The compounds, compositions, and methods described herein are directed toward these needs and other ends.

SUMMARY

The present invention provides, inter alia, compounds of Formula I:

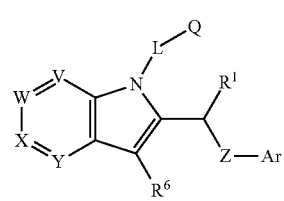

or a pharmaceutically acceptable salt thereof; wherein V, W, X, Y, L, Q, $R^1$, $R^6$, Z, and Ar are defined infra.

The present invention further provides compositions comprising a compound of the invention, or a pharmaceutically acceptable salt thereof, and at least one pharmaceutically acceptable carrier.

The present invention also provides methods of modulating an activity of a PI3K kinase, comprising contacting the kinase with a compound of the invention, or a pharmaceutically acceptable salt thereof.

The present invention further provides methods of treating a disease in a patient, wherein the disease is associated with abnormal expression or activity of a PI3K kinase, comprising administering to the patient a therapeutically effective amount of a compound of the invention, or a pharmaceutically acceptable salt thereof.

The present invention further provides methods of treating an immune-based disease in a patient, comprising administering to the patient a therapeutically effective amount of a compound of the invention, or a pharmaceutically acceptable salt thereof.

The present invention also provides methods of treating a cancer in a patient, comprising administering to the patient a therapeutically effective amount of a compound of the invention, or a pharmaceutically acceptable salt thereof.

The present invention further provides methods of treating a lung disease in a patient, comprising administering to the patient a therapeutically effective amount of a compound of the invention, or a pharmaceutically acceptable salt thereof.

The present invention also provides a compound of invention, or a pharmaceutically acceptable salt thereof, for use in any of the methods described herein.

The present invention further provides use of a compound, or a pharmaceutically acceptable salt thereof, for the manufacture of a medicament for use in any of the methods described herein.

DETAILED DESCRIPTION

The present invention provides, inter alia, a compound of Formula I:

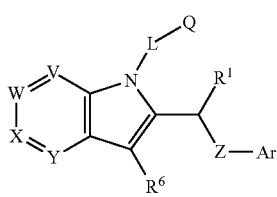

I or a pharmaceutically acceptable salt thereof; wherein:
V is $CR^2$ or N;
W is $CR^3$ or N;
X is $CR^4$ or N;
Y is $CR^5$ or N;
provided that —V=W—X=Y— is selected from —$CR^2$=$CR^3$—$CR^4$=$CR^5$—, —N=$CR^3$—$CR^4$=$CR^5$—, —$CR^2$=N—$CR^4$=$CR^5$—, —$CR^2$=$CR^3$—N=$CR^5$—, and —$CR^2$=$CR^3$—$CR^4$=N—;
Z is a bond, O, S, or $NR^A$;
L is a bond or $C_{1-4}$ alkylene;
provided that when L is $C_{1-4}$ alkylene, then Z is O, S, or $NR^A$;
provided that when Z is a bond, then Ar is attached to Z at a nitrogen atom of Ar;
provided that when $R^6$ is bromo or —$CO_2$(ethyl), then Z is bond, O, or $NR^A$;
Q is $C_{1-6}$ alkyl, $C_{2-6}$ alkenyl, $C_{2-6}$ alkynyl, or Cy; wherein $C_{1-6}$ alkyl, $C_{2-6}$ alkenyl, and $C_{2-6}$ alkynyl are each optionally substituted by 1, 2, 3, 4, or 5 independently selected $R^C$ groups;
Cy is cycloalkyl, heterocycloalkyl, aryl or heteroaryl, each of which is optionally substituted with 1, 2, 3, 4, or 5 independently selected $R^C$ groups;
each $R^C$ is independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein the $C_{1-6}$ alkyl, $C_{2-6}$ alkenyl, $C_{2-6}$ alkynyl, aryl, cycloalkyl, heteroaryl, and heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^g)NR^{c2}R^{d2}$, $NR^{c2}C(=NR^g)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;
$R^1$ is independently selected from H, $C_{1-6}$ alkyl, $C_{1-6}$ haloalkyl, $C_{2-6}$ alkenyl, and $C_{2-6}$ alkynyl; wherein the $C_{1-6}$ alkyl, $C_{2-6}$ alkenyl, and $C_{2-6}$ alkynyl are each optionally substituted with 1, 2, 3 or 4 substituents independently selected from halo, OH, CN, $NR^{1a}R^{2b}$, $C_{1-6}$ alkoxy, $C_{1-6}$ haloalkoxy, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl) aminocarbonyl amino;
each $R^{1a}$ and $R^{2b}$ is independently selected from H and $C_{1-6}$ alkyl;
or any $R^{1a}$ and $R^{2b}$ together with the N atom to which they are attached form a 4-, 5-, 6-, or 7-membered heterocycloalkyl group, which is optionally substituted with 1, 2, 3, or 4 substituents independently selected from $C_{1-6}$ alkyl;
$R^2$, $R^3$, $R^4$, $R^5$, and $R^6$ are each independently selected from H, OH, $NO_2$, CN, halo, $C_{1-6}$ alkyl, $C_{2-6}$ alkenyl, $C_{2-6}$ alkynyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl) aminosulfonylamino, aminocarbonylamino, $C_{1-6}$ alkylaminocarbonylamino, and di($C_{1-6}$ alkyl)aminocarbonylamino;
Ar is bicyclic azaheteroaryl, substituted with n independently selected $R^D$ groups; wherein n is 0, 1, 2, 3, 4, or 5;
each $R^D$ is independently selected from —($C_{1-4}$ alkyl)$_r$-$Cy^1$, halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^e)NR^{c1}R^{d1}$, $NR^{c1}C(=NR^e)NR^{c1}R^{d1}$, $NR^{c1}R^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$;

R$^A$ is selected from H, C$_{1-6}$ alkyl, C$_{2-6}$ alkenyl, and C$_{2-6}$ alkynyl;

each Cy$^1$ is, independently, aryl, heteroaryl, cycloalkyl, or heterocycloalkyl, each optionally substituted by 1, 2, 3, 4, or 5 substituents independently selected from OH, NO$_2$, CN, halo, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

each R$^a$, R$^c$, and R$^d$ is independently selected from H, C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein the C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from OH, NO$_2$, CN, halo, C$_{1-6}$ alkyl, C$_{2-6}$ alkenyl, C$_{2-6}$ alkynyl, C$_{3-7}$ cycloalkyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

each R$^b$ is independently selected from C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein the C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from OH, NO$_2$, CN, halo, C$_{1-6}$ alkyl, C$_{2-6}$ alkenyl, C$_{2-6}$ alkynyl, C$_{3-7}$ cycloalkyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

or any R$^c$ and R$^d$ together with the N atom to which they are attached form a 4-, 5-, 6-, or 7-membered heterocycloalkyl group or a heteroaryl group, each optionally substituted with 1, 2, or 3 substituents independently selected from OH, NO$_2$, CN, halo, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

each R$^e$ and R$^g$ is independently selected from H, C$_{1-6}$ alkyl, and CN;

each R$^{a1}$, R$^{c1}$, and R$^{d1}$ is independently selected from H, C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein the C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from OH, NO$_2$, CN, halo, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

each R$^{b1}$ is independently selected from C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein the C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from OH, NO$_2$, CN, halo, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

or any R$^{c1}$ and R$^{d1}$ together with the N atom to which they are attached form a 4-, 5-, 6-, or 7-membered heterocycloalkyl group or a heteroaryl group, each optionally substituted with 1, 2, or 3 substituents independently selected from OH, NO$_2$, CN, halo, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

each R$^{a2}$, R$^{c2}$, and R$^{d2}$ is independently selected from H, C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein the C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from OH, NO$_2$, CN, halo, C$_{1-6}$ alkyl, C$_{2-6}$ alkenyl, C$_{2-6}$ alkynyl, C$_{3-7}$ cycloalkyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

each R$^{b2}$ is independently selected from C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein the C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from OH, NO$_2$, CN, halo, C$_{1-6}$ alkyl, C$_{2-6}$ alkenyl, C$_{2-6}$ alkynyl, C$_{3-7}$ cycloalkyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

or any R$^{c2}$ and R$^{d2}$ together with the N atom to which they are attached form a 4-, 5-, 6-, or 7-membered heterocycloalkyl group or a heteroaryl group, each optionally substituted with 1, 2, or 3 substituents independently selected from OH, NO$_2$, CN, halo, C$_{1-6}$ alkyl, C$_{2-6}$ alkenyl, C$_{2-6}$ alkynyl, C$_{3-7}$ cycloalkyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino; and
r is 0 or 1.

In some embodiments, the compound is a compound of Formula Ia:

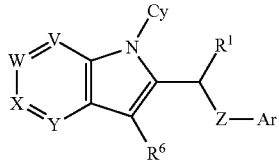

Ia or a pharmaceutically acceptable salt thereof; wherein:
V is CR$^2$ or N;
W is CR$^3$ or N;
X is CR$^4$ or N;
Y is CR$^5$ or N;
provided that —V=W—X=Y— is selected from —CR$^2$=CR$^3$—CR$^4$=CR$^5$—, —N=CR$^3$—CR$^4$=CR$^5$—, —CR$^2$=N—CR$^4$=CR$^5$—, —CR$^2$=CR$^3$—N=CR$^5$—, and —CR$^2$=CR$^3$—CR$^4$=N—;

Z is O, S, or NR$^A$;
provided that when R$^6$ is bromo or —CO$_2$(ethyl), then Z is a bond, O, or NR$^A$;
Cy is cycloalkyl, heterocycloalkyl, aryl or heteroaryl, each of which is optionally substituted with 1, 2, 3, 4, or 5 independently selected R$^C$ groups;

each R$^C$ is independently selected from halo, C$_{1-6}$ alkyl, C$_{2-6}$ alkenyl, C$_{2-6}$ alkynyl, C$_{1-6}$ haloalkyl, halosulfanyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$) NR$^c$R$^d$, NR$^c$S(O)R$^b$, NR$^c$S(O)$_2$R$^b$, NR$^c$S(O)$_2$NR$^c$R$^d$, S(O) R$^b$, S(O)NR$^c$R$^d$, S(O)$_2$R$^b$, and S(O)$_2$NR$^c$R$^d$; wherein the C$_{1-6}$ alkyl, C$_{2-6}$ alkenyl, C$_{2-6}$ alkynyl, aryl, cycloalkyl, heteroaryl, and heterocycloalkyl are each optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, halosulfanyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^g$)NR$^{c2}$R$^{d2}$; NR$^{c2}$C (=NR$^g$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S (O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$;

R$^1$ is independently selected from H, C$_{1-6}$ alkyl, C$_{1-6}$ haloalkyl, C$_{2-6}$ alkenyl, and C$_{2-6}$ alkynyl; wherein the C$_{1-6}$ alkyl, C$_{2-6}$ alkenyl, and C$_{2-6}$ alkynyl are each optionally substituted with 1, 2, 3 or 4 substituents independently selected from halo, OH, CN, NR$^{1a}$R$^{2b}$, C$_{1-6}$ alkoxy, C$_{1-6}$ haloalkoxy, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl) aminosulfonylamino, aminocarbonylamino, C$_{1-6}$ alkylaminocarbonylamino, and di(C$_{1-6}$ alkyl)aminocarbonylamino;

each R$^{1a}$ and R$^{2b}$ is independently selected from H and C$_{1-6}$ alkyl;
or any R$^{1a}$ and R$^{2b}$ together with the N atom to which they are attached form a 4-, 5-, 6-, or 7-membered heterocycloalkyl group, which is optionally substituted with 1, 2, 3, or 4 substituents independently selected from C$_{1-6}$ alkyl;

R$^2$, R$^3$, R$^4$, R$^5$, and R$^6$ are each independently selected from H, OH, NO$_2$, CN, halo, C$_{1-6}$ alkyl, C$_{2-6}$ alkenyl, C$_{2-6}$ alkynyl, C$_{3-7}$ cycloalkyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl) aminosulfonylamino, aminocarbonylamino, C$_{1-6}$ alkylaminocarbonylamino, and di(C$_{1-6}$ alkyl)aminocarbonylamino;

Ar is bicyclic azaheteroaryl, substituted with n independently selected R$^D$ groups; wherein n is 0, 1, 2, 3, 4, or 5;
each R$^D$ is independently selected from —(C$_{1-4}$ alkyl)$_r$-Cy$^1$, halo, C$_{1-6}$ alkyl, C$_{2-6}$ alkenyl, C$_{2-6}$ alkynyl, C$_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^e$)NR$^{c1}$R$^{d1}$, NR$^{c1}$C(=NR$^e$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S (O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$;

R$^A$ is selected from H, C$_{1-6}$ alkyl, C$_{2-6}$ alkenyl, and C$_{2-6}$ alkynyl;

each Cy$^1$ is, independently, aryl, heteroaryl, cycloalkyl, or heterocycloalkyl, each optionally substituted by 1, 2, 3, 4, or 5 substituents independently selected from OH, NO$_2$, CN, halo, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

each R$^a$, R$^c$, and R$^d$ is independently selected from H, C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein the C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from OH, NO$_2$, CN, halo, C$_{1-6}$ alkyl, C$_{2-6}$ alkenyl, C$_{2-6}$ alkynyl, C$_{3-7}$ cycloalkyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

each R$^b$ is independently selected from C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein the C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from OH, NO$_2$, CN, halo, C$_{1-6}$ alkyl, C$_{2-6}$ alkenyl, C$_{2-6}$ alkynyl, C$_{3-7}$ cycloalkyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

or any R$^c$ and R$^d$ together with the N atom to which they are attached form a 4-, 5-, 6-, or 7-membered heterocycloalkyl group or a heteroaryl group, each optionally substituted with 1, 2, or 3 substituents independently selected from OH, NO$_2$, CN, halo, C$_{1-6}$ alkyl, C$_{2-6}$ alkenyl, C$_{2-6}$ alkynyl, C$_{3-7}$ cycloalkyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

each R$^e$ and R$^g$ is independently selected from H, C$_{1-6}$ alkyl, and CN;

each R$^{a1}$, R$^{c1}$, and R$^{d1}$ is independently selected from H, C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein the C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from OH, NO$_2$, CN, halo, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

each R$^{b1}$ is independently selected from C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein the C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from OH, NO$_2$, CN, halo, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

or any R$^{c1}$ and R$^{d1}$ together with the N atom to which they are attached form a 4-, 5-, 6-, or 7-membered heterocycloalkyl group or a heteroaryl group, each optionally substituted with 1, 2, or 3 substituents independently selected from OH, NO$_2$, CN, halo, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

each R$^{a2}$, R$^{c2}$, and R$^{d2}$ is independently selected from H, C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein the C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from OH, NO$_2$, CN, halo, $C_{1-6}$ alkyl, $C_{2-6}$ alkenyl, $C_{2-6}$ alkynyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, amino sulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^{b2}$ is independently selected from $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein the $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from OH, $NO_2$, CN, halo, $C_{1-6}$ alkyl, $C_{2-6}$ alkenyl, $C_{2-6}$ alkynyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

or any $R^{c2}$ and $R^{d2}$ together with the N atom to which they are attached form a 4-, 5-, 6-, or 7-membered heterocycloalkyl group or a heteroaryl group, each optionally substituted with 1, 2, or 3 substituents independently selected from OH, $NO_2$, CN, halo, $C_{1-6}$ alkyl, $C_{2-6}$ alkenyl, $C_{2-6}$ alkynyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and r is 0 or 1.

In one embodiment of the preceding embodiment, when $R^6$ is bromo or —$CO_2$(ethyl), then Z is O or $NR^A$.

In some embodiments, Z is $NR^A$.

In some embodiments, Cy is aryl, optionally substituted with 1, 2, 3, 4, or 5 independently selected $R^C$ groups. In some embodiments, Cy is heterocycloalkyl, optionally substituted with 1, 2, 3, 4, or 5 independently selected $R^C$ groups. In some embodiments, Cy is monocyclic heterocycloalkyl, optionally substituted with 1, 2, 3, 4, or 5 independently selected $R^C$ groups. In some embodiments, Cy is heteroaryl, optionally substituted with 1, 2, 3, 4, or 5 independently selected $R^C$ groups. In some embodiments, Cy is monocyclic heteroaryl, optionally substituted with 1, 2, 3, 4, or 5 independently selected $R^C$ groups. In some embodiments, Cy is a phenyl ring, which is optionally substituted with 1, 2, 3, 4, or 5 independently selected $R^C$ groups.

In some embodiments, each $R^C$ is independently selected from halo, $C_{1-6}$ alkyl, $C_{2-6}$ alkenyl, $C_{2-6}$ alkynyl, $C_{1-6}$ haloalkyl, CN, $NO_2$, $OR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $S(O)R^b$, $S(O)NR^cR^d$, $S(O)_2R^b$, and $S(O)_2NR^cR^d$; wherein the $C_{1-6}$ alkyl is optionally substituted with 1, 2, 3, 4, or 5 substituents independently selected from hydroxy, $C_{1-6}$ alkoxy, and $C_{1-6}$ haloalkoxy. In some embodiments, each $R^C$ is independently halo.

In some embodiments, Ar is a purine ring, substituted with n independently selected $R^D$ groups; wherein n is 0, 1, or 2.

In some embodiments, Ar is a moiety of formula:

wherein n is 0 or 1.

In some embodiments, n is 0.

In some embodiments, each $R^D$ is, independently, $NR^{c1}R^{d1}$. In some embodiments, each $R^D$ is independently selected from amino, $C_{1-6}$ alkylamino, and di($C_{1-6}$-alkyl)amino.

In some embodiments, $R^1$ is selected from $C_{1-6}$ alkyl. In some embodiments, $R^1$ is methyl.

In some embodiments, $R^A$ is H.

In some embodiments, $R^2$, $R^3$, $R^4$, $R^5$, and $R^6$ are independently selected from H, CN, halo, $C_{1-6}$ alkyl, $C_{1-6}$ haloalkyl, $C_{1-6}$ alkoxy, and $C_{1-6}$ haloalkoxy. In some embodiments, $R^2$, $R^3$, $R^4$, $R^5$, and $R^6$ are independently selected from H, CN, halo, and $C_{1-6}$ alkyl.

In some embodiments, $R^6$ is H, CN, halo, or $C_{1-6}$ alkyl. In some embodiments, $R^6$ is H, F, Cl, CN, or methyl.

In some embodiments, V is $CR^2$. In some embodiments, V is N.

In some embodiments, W is $CR^3$.

In some embodiments, X is $CR^4$.

In some embodiments, Y is $CR^5$.

In some embodiments:

Z is NH;

Cy is heterocycloalkyl, aryl, or heteroaryl, each of which is optionally substituted with 1, 2, 3, 4, or 5 independently selected $R^C$ groups;

each $R^C$ is independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^eS(O)_2R^b$, $NR^cS(O)_2NR^cR^d$, $S(O)R^b$, $S(O)NR^cR^d$, $S(O)_2R^b$, and $S(O)_2NR^cR^d$; wherein the $C_{1-6}$ alkyl, $C_{2-6}$ alkenyl, $C_{2-6}$ alkynyl, and $C_{1-6}$ haloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a2}$, $SR^{a2}$, $C(O)R^{b2}$, $C(O)NR^{c2}NR^{d2}$, $C(O)OR^{a2}$, $OC(O)R^{b2}$, $OC(O)NR^{c2}R^{d2}$, $C(=NR^g)NR^{c2}R^{d2}$, $NR^{c2}C(=NR^g)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

Ar is a bicyclic azaheteroaryl group, substituted with n independently selected $R^D$ groups; wherein n is 0, 1, 2, 3, or 4;

each $R^D$ is, independently, $NR^{c1}R^{d1}$;

$R^1$ is, independently, $C_{1-6}$ alkyl;

$R^2$, $R^3$, $R^4$, and $R^5$ are independently selected from H, OH, halo, CN, $C_{1-6}$ alkyl, $C_{1-6}$ haloalkyl, $C_{1-4}$ alkoxy, $C_{1-4}$ haloalkoxy, amino, $C_{1-4}$ alkylamino, di($C_{1-4}$-alkyl)amino, carboxy, $C_{1-4}$ alkylcarbonyl, $C_{1-4}$ alkoxycarbonyl, carbamyl, $C_{1-4}$ alkylcarbamyl, di($C_{1-4}$-alkyl)carbamyl, $C_{1-4}$ alkylcarbonylamino, $C_{1-4}$ alkylthio, $C_{1-4}$ alkylsulfinyl, and $C_{1-4}$ alkylsulfonyl; and $R^6$ is H, CN, halo, or $C_{1-6}$ alkyl.

In some embodiments:

Z is NH;

Cy is heterocycloalkyl, aryl, or heteroaryl, each of which is optionally substituted with 1, 2, 3, 4, or 5 independently selected $R^C$ groups;

each $R^C$ is independently selected from halo, $C_{1-6}$ alkyl, $C_{2-6}$ alkenyl, $C_{2-6}$ alkynyl, $C_{1-6}$ haloalkyl, CN, $NO_2$, $OR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $S(O)R^b$, $S(O)NR^cR^d$, $S(O)_2R^b$, and $S(O)_2NR^cR^d$; wherein the $C_{1-6}$ alkyl is optionally substituted with 1, 2, 3, 4, or 5 substituents independently selected from hydroxy, $C_{1-6}$ alkoxy, and $C_{1-6}$ haloalkoxy;

Ar is a purine ring, substituted with n independently selected $R^D$ groups; wherein n is 0 or 1;

each $R^D$ is, independently, $NR^{c1}R^{d1}$;

$R^1$ is $C_{1-6}$ alkyl;

$R^2$, $R^3$, $R^4$, and $R^5$ are each independently selected from H, halo, CN, $C_{1-6}$ alkyl, $C_{1-6}$ haloalkyl, $C_{1-6}$ alkoxy, and $C_{1-6}$ haloalkoxy; and $R^6$ is H, CN, halo, or $C_{1-6}$ alkyl.

In some embodiments:

Z is NH;

Cy is heterocycloalkyl, aryl, or heteroaryl, each of which is optionally substituted with 1, 2, 3, 4, or 5 independently selected $R^C$ groups;

each $R^C$ is independently selected from halo, $C_{1-6}$ alkyl, $C_{2-6}$ alkenyl, $C_{2-6}$ alkynyl, $C_{1-6}$ haloalkyl, CN, $NO_2$, $OR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $S(O)R^b$, $S(O)N^cR^d$, $S(O)_2R^b$, and $S(O)_2NR^cR^d$; wherein the $C_{1-6}$ alkyl is optionally substituted with 1, 2, 3, 4, or 5 substituents independently selected from hydroxy, $C_{1-6}$ alkoxy, and $C_{1-6}$ haloalkoxy;

Ar is a moiety of formula:

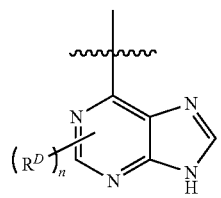

wherein n is 0 or 1;

each $R^D$ is, independently, $NR^{c1}R^{d1}$;

$R^1$ is $C_{1-6}$ alkyl;

$R^2$, $R^3$, $R^4$, and $R^5$ are each independently selected from H, halo, CN, $C_{1-6}$ alkyl, $C_{1-6}$ haloalkyl, $C_{1-6}$ alkoxy, and $C_{1-6}$ haloalkoxy; and $R^6$ is H, CN, halo, or $C_{1-6}$ alkyl.

In some embodiments:

Z is NH;

Cy is heterocycloalkyl, aryl or heteroaryl, each of which is optionally substituted with 1, 2, 3, 4, or 5 independently selected $R^C$ groups;

each $R^C$ is independently selected from halo, $C_{1-6}$ alkyl, $C_{2-6}$ alkenyl, $C_{2-6}$ alkynyl, $C_{1-6}$ haloalkyl, CN, $NO_2$, $OR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $S(O)R^b$, $S(O)NR^cR^d$, $S(O)_2R^b$, and $S(O)_2NR^cR^d$; wherein the $C_{1-6}$ alkyl is optionally substituted with 1, 2, 3, 4, or 5 substituents independently selected from hydroxy, $C_{1-6}$ alkoxy, and $C_{1-6}$ haloalkoxy;

Ar is a moiety of formula:

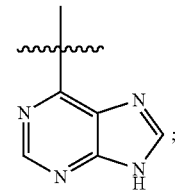 [SMILES: *c1ncnc2[nH]cnc12]

$R^1$ is $C_{1-6}$ alkyl;

$R^2$, $R^3$, $R^4$, and $R^5$ are each independently selected from H, halo, CN, $C_{1-6}$ alkyl, $C_{1-6}$ haloalkyl, $C_{1-6}$ alkoxy, and $C_{1-6}$ haloalkoxy; and $R^6$ is H, CN, halo, or $C_{1-6}$ alkyl.

In some embodiments:

Z is NH;

Cy is aryl, optionally substituted with 1, 2, 3, 4, or 5 independently selected $R^C$ groups;

each $R^C$ is independently selected from halo;

Ar is a moiety of formula:

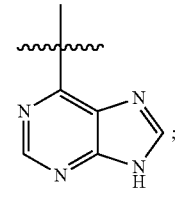 [SMILES: *c1ncnc2[nH]cnc12]

$R^1$ is $C_{1-6}$ alkyl; and $R^2$, $R^3$, $R^4$, $R^5$, and $R^6$ are each independently selected from H, halo, CN, $C_{1-6}$ alkyl, and $C_{1-6}$ haloalkyl.

In some embodiments, the compound is a compound of Formula II:

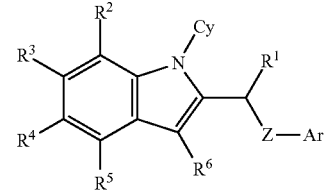

or a pharmaceutically acceptable salt thereof.

In some embodiments, the compound is a compound of Formula III:

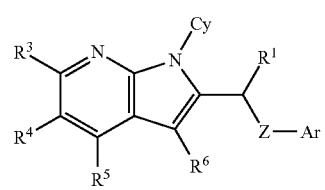

or a pharmaceutically acceptable salt thereof.

In some embodiments, the compound is a compound of Formula IIa:

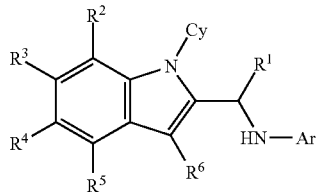

IIa or a pharmaceutically acceptable salt thereof.

In some embodiments, the compound is a compound of Formula IIIa:

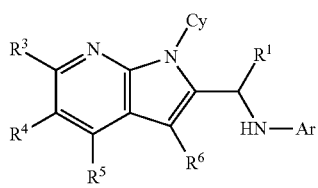

IIIa or a pharmaceutically acceptable salt thereof.

In some embodiments, the compound is selected from:

N-{1-[6-chloro-1-(3-fluorophenyl)-1H-indol-2-yl]ethyl}-9H-purin-6-amine;

N-{1-[4-chloro-1-(3-fluorophenyl)-1H-indol-2-yl]ethyl}-9H-purin-6-amine;

N-{1-[3-chloro-1-(3-fluorophenyl)-1H-indol-2-yl]ethyl}-9H-purin-6-amine;

N-{1-[3,4-dichloro-1-(3-fluorophenyl)-1H-indol-2-yl]ethyl}-9H-purin-6-amine;

N-{1-[3-bromo-1-(3-fluorophenyl)-1H-indol-2-yl]ethyl}-9H-purin-6-amine;

N-{1-[3-chloro-1-(3-fluorophenyl)-1H-pyrrolo[2,3-b]pyridin-2-yl]ethyl}-9H-purin-6-amine;

N-(1-(1-(3-fluorophenyl)-1H-pyrrolo[2,3-b]pyridin-2-yl)ethyl)-9H-purin-6-amine;

N-{1-[1-(3-fluorophenyl)-3-methyl-1H-indol-2-yl]ethyl}-9H-purin-6-amine;

2-(1-(9H-purin-6-ylamino)ethyl)-1-(3-fluorophenyl)-1H-indole-3-carbonitrile; and N-(1-(3-fluoro-1-(3-fluorophenyl)-1H-pyrrolo[2,3-b]pyridin-2-yl)ethyl)-9H-purin-6-amine;

or a pharmaceutically acceptable salt of any of the aforementioned.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R. In another example, when an optionally multiple substituent is designated in the form:

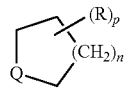

then it is to be understood that substituent R can occur p number of times on the ring, and R can be a different moiety at each occurrence. It is to be understood that each R group may replace any hydrogen atom attached to a ring atom, including one or both of the (CH$_2$)$_n$ hydrogen atoms. Further, in the above example, should the variable Q be defined to include hydrogens, such as when Q is the to be CH$_2$, NH, etc., any floating substituent such as R in the above example, can replace a hydrogen of the Q variable as well as a hydrogen in any other non-variable component of the ring.

As used herein, the phrase "optionally substituted" means unsubstituted or substituted. As used herein, the term "substituted" means that a hydrogen atom is removed and replaced by a substituent. It is to be understood that substitution at a given atom is limited by valency.

At various places in the present specification, rings are described (e.g., "a piperidine ring"). Unless otherwise specified, these rings can be attached to the rest of the molecule at any ring member as permitted by valency. For example, the term "a pyridine ring" may refer to a pyridin-2-yl, pyridin-3-yl, or pyridin-4-yl ring.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like.

As used herein, the term "alkylene", employed alone or in combination with other terms, refers to a divalent alkyl linking group. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like.

As used herein, "$C_{n-m}$ alkenyl", employed alone or in combination with other terms, refers to an alkyl group having one or more double carbon-carbon bonds and having n to m carbons. In some embodiments, the alkenyl moiety contains 2 to 6 or to 2 to 4 carbon atoms. Example alkenyl groups include, but are not limited to, ethenyl, n-propenyl, isopropenyl, n-butenyl, sec-butenyl, and the like.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), t-butoxy, and the like. In some embodiments, the alkyl group has 1 to 6 or 1 to 4 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6 or 1 to 4 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6 or 1 to 4 carbon atoms.

As used herein, the term "$C_{n-m}$ alkylcarbonyl" refers to a group of formula —C(O)— alkyl, wherein the alkyl group has n to m carbon atoms. In some embodiments, the alkyl group has 1 to 6 or 1 to 4 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6 or 1 to 4 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6 or 1 to 4 carbon atoms.

As used herein, the term "aminosulfonyl", employed alone or in combination with other terms, refers to a group of formula —S(O)$_2$NH$_2$, wherein the alkyl group has n to m carbon atoms.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6 or 1 to 4 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6 or 1 to 4 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6 or 1 to 4 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6 or 1 to 4 carbon atoms.

As used herein, the term "aminocarbonylamino" refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6 or 1 to 4 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6 or 1 to 4 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6 or 1 to 4 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6 or 1 to 4 carbon atoms.

As used herein, the term "$C_{n-m}$ alkylsulfinyl" refers to a group of formula —S(O)— alkyl, wherein the alkyl group has n to m carbon atoms. In some embodiments, the alkyl group has 1 to 6 or 1 to 4 carbon atoms.

As used herein, the term "$C_{n-m}$ alkylsulfonyl" refers to a group of formula —S(O)$_2$— alkyl, wherein the alkyl group has n to m carbon atoms. In some embodiments, the alkyl group has 1 to 6 or 1 to 4 carbon atoms.

As used herein, the term "amino" refers to a group of formula —NH$_2$.

As used herein, the term "aryl", employed alone or in combination with other terms, refers to a monocyclic or polycyclic (e.g., having 2, 3 or 4 fused rings) fully aromatic hydrocarbon, such as, but not limited to, phenyl, 1-naphthyl, 2-naphthyl, anthracenyl, phenanthrenyl, and the like. In some embodiments, aryl is $C_{6-12}$ aryl. In some embodiments, the aryl group is a naphthalene ring or phenyl ring. In some embodiments, the aryl group is phenyl.

As used herein, the term "arylalkyl" refers to a group of formula-alkylene-aryl. In some embodiments, arylalkyl is $C_{6-12}$ aryl-$C_{1-3}$ alkyl. In some embodiments, arylalkyl is benzyl.

As used herein, the term "carbamyl" refers to a group of formula —C(O)NH$_2$.

As used herein, the term "carbonyl", employed alone or in combination with other terms, refers to a —C(O)— group.

As used herein, the term "carboxy" refers to a group of formula —C(O)OH.

As used herein, the term "cycloalkyl", employed alone or in combination with other terms, refers to a non-aromatic cyclic hydrocarbon moiety, which may optionally contain one or more alkenylene groups as part of the ring structure. Cycloalkyl groups can include mono- or polycyclic (e.g., having 2, 3 or 4 fused rings) ring systems. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. One or more ring-forming carbon atoms of a cycloalkyl group can be oxidized to form carbonyl linkages. In some embodiments, cycloalkyl is $C_{3-12}$ cycloalkyl, which is monocyclic or bicyclic. Examplary cycloalkyl groups include 1,2,3,4-tetrahydro-naphthalene, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, the cycloalkyl group is cyclopropyl, cyclobutyl, cyclopentyl, or cyclohexyl.

As used herein, the term "cycloalkylalkyl" refers to a group of formula-alkylene-cycloalkyl. In some embodiments, cycloalkylalkyl is $C_{3-12}$ cycloalkyl-$C_{1-3}$ alkyl, wherein the cycloalkyl portion is monocyclic or bicyclic.

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6 or 1 to 4 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6 or 1 to 4 carbon atoms.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6 or 1 to 4 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6 or 1 to 4 carbon atoms.

As used herein, the term "fluorinated $C_{n-m}$ haloalkyl" refers to a $C_{n-m}$ haloalkyl wherein the halogen atoms are selected from fluorine. In some embodiments, fluorinated $C_{n-m}$ haloalkyl is fluoromethyl, difluoromethyl, or trifluoromethyl. In some embodiments, the alkyl group has 1 to 6 or 1 to 4 carbon atoms.

As used herein, "halosulfanyl" refers to a sulfur group having one or more halogen substituents. Example halosulfanyl groups include pentahalosulfanyl groups such as $SF_5$.

As used herein, the term "heteroaryl", employed alone or in combination with other terms, refers to a monocyclic or polycyclic (e.g., having 2, 3 or 4 fused rings) fully aromatic hydrocarbon moiety, having one or more heteroatom ring members selected from nitrogen, sulfur and oxygen. In some embodiments, heteroaryl is 5- to 10-membered $C_{1-9}$ heteroaryl, which is monocyclic or bicyclic and which has 1, 2, 3, or 4 heteroatom ring members independently selected from nitrogen, sulfur and oxygen. When the heteroaryl group contains more than one heteroatom ring member, the heteroatoms may be the same or different. Example heteroaryl groups include, but are not limited to, pyridine, pyrimidine, pyrazine, pyridazine, pyrrole, pyrazole, azolyl, oxazole, thiazole, imidazole, furan, thiophene, quinoline, isoquinoline, indole, benzothiophene, benzofuran, benzisoxazole, imidazo[1,2-b]thiazole, purine, or the like.

As used herein, the term "bicyclic azaheteroaryl" refers to a bicyclic fused heteroaryl group having 1, 2, 3, or 4 nitrogen ring members. The bicyclic azaheteroaryl group may optionally have O or S heterotom ring members in addition to the nitrogen ring members. In some embodiments, the only heteroatom ring members in the bicyclic azaheteroaryl group are nitrogen heteroatoms. In some embodiments, the bicyclic azaheteroaryl group is $C_{4-9}$ bicyclic azaheteroaryl, which has 7 to 10 ring forming atoms independently selected from carbon, nitrogen, sulfur and oxygen, wherein 1, 2, 3, or 4 of the ring forming atoms are independently selected from nitrogen, sulfur and oxygen provided that at least one ring atom is nitrogen. In some embodiments, bicyclic azaheteroaryl is a purine ring.

As used herein, the term "heteroarylalkyl" refers to a group of formula-alkylene-heteroaryl. In some embodiments, heteroarylalkyl is $C_{1-9}$ heteroaryl-$C_{1-3}$ alkyl, wherein the heteroaryl portion is monocyclic or bicyclic and has 1, 2, 3, or 4 heteroatom ring members independently selected from nitrogen, sulfur and oxygen.

As used herein, the term "heterocycloalkyl", employed alone or in combination with other terms, refers to non-aromatic ring system, which may optionally contain one or more alkenylene or alkynylene groups as part of the ring structure, and which has at least one heteroatom ring member independently selected from nitrogen, sulfur and oxygen. When the heterocycloalkyl groups contains more than one heteroatom, the heteroatoms may be the same or different. Heterocycloalkyl groups can include mono- or polycyclic (e.g., having 2, 3 or 4 fused rings) ring systems. Also included in the definition of heterocycloalkyl are moieties that have one or more aromatic rings fused (i.e., having a bond in common with) to the non-aromatic ring, for example, 1,2,3,4-tetrahydro-quinoline and the like. The carbon atoms or heteroatoms in the ring(s) of the heterocycloalkyl group can be oxidized to form a carbonyl, or sulfonyl group (or other oxidized linkage) or a nitrogen atom can be quaternized. In some embodiments, heterocycloalkyl is 5- to 10-membered $C_{2-9}$ heterocycloalkyl, which is monocyclic or bicyclic and which has 1, 2, 3, or 4 heteroatom ring members independently selected from nitrogen, sulfur and oxygen. Examples of heterocycloalkyl groups include 1,2,3,4-tetrahydro-quinoline, azetidine, azepane, pyrrolidine, piperidine, piperazine, morpholine, thiomorpholine, and pyran.

A five-membered ring heteroaryl is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, the term "heterocycloalkylalkyl" refers to a group of formula-alkylene-heterocycloalkyl. In some embodiments, heterocycloalkylalkyl is $C_{2-9}$ heterocycloalkyl-$C_{1-3}$ alkyl, wherein the heterocycloalkyl portion is monocyclic or bicyclic and has 1, 2, 3, or 4 heteroatom ring members independently selected from nitrogen, sulfur and oxygen.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution. For example, purine includes the 9H and a 7H tautomeric forms:

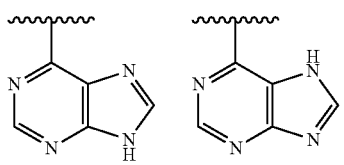

Compounds of the invention can include both the 9H and 7H tautomeric forms.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric iosomers, tautomers, and isotopes of the structures depicted. Compounds herein identified by name or structure as one particular tautomeric form are intended to include other tautomeric forms unless otherwise specified (e.g., in the case of purine rings, unless otherwise indicated, when the compound name or structure has the 9H tautomer, it is understood that the 7H tautomer is also encompassed).

All compounds, and pharmaceutically acceptable salts thereof, can be found together with other substances such as water and solvents (e.g. hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3rd Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS) or thin layer chromatography (TLC). Compounds can be purified by those skilled in the art by a variety of methods, including high performance liquid chromatography (HPLC) ("*Preparative LC-MS Purification: Improved Compound Specific Method Optimization*" Karl F. Blom, Brian Glass, Richard Sparks, Andrew P. Combs *J. Combi. Chem.* 2004, 6(6), 874-883, which is incorporated herein by reference in its entirety) and normal phase silica chromatography.

Example synthetic methods for preparing compounds of Formula I, wherein Z is $NR^A$, are provided in Scheme I. An ester compound of formula (i) (wherein R is alkyl (e.g., ethyl)) may be reacted with a compound of formula Cy-B(OH)$_2$ in the presence of cupric acetate to give a compound of formula (ii). The ester (ii) can then be reduced with an appropriate reducing agent, such as lithium tetrahydroaluminate, to give an alcohol compound of formula (iii). The alcohol (iii) can then be oxidized to an aldehyde compound of formula (iv) using an appropriate oxidizing agent. The aldehyde (iv) may then be reacted with a Grignard reagent of formula $R^1$—MgBr to give an alcohol of formula (v). The alcohol (v) can be converted to the mesylate and then reacted with sodium azide to give an azide compound of formula (vi). The azide (vi) can then be converted to an amine under appropriate conditions (e.g., treatment with trimethylphosphine) to give an amine of formula (vii). Finally, the amine (vii) can be reacted with an appropriate alkylating agent $R^AX$ (e.g., MeI) and then a heteroaryl halide compound (e.g., Ar—$X^1$, wherein $X^1$ is bromo, iodo, etc.) to give a compound of Formula I. The reaction of amine (vii) with $R^A$ can be eliminated to give compounds of Formula I where $R^A$ is H.

Scheme I

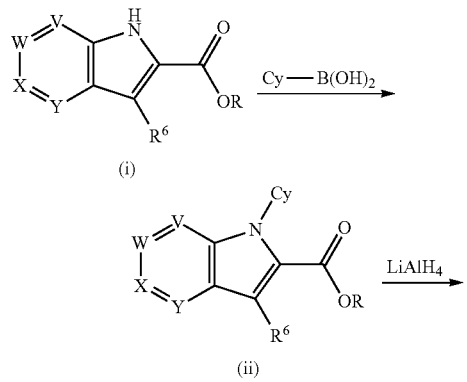

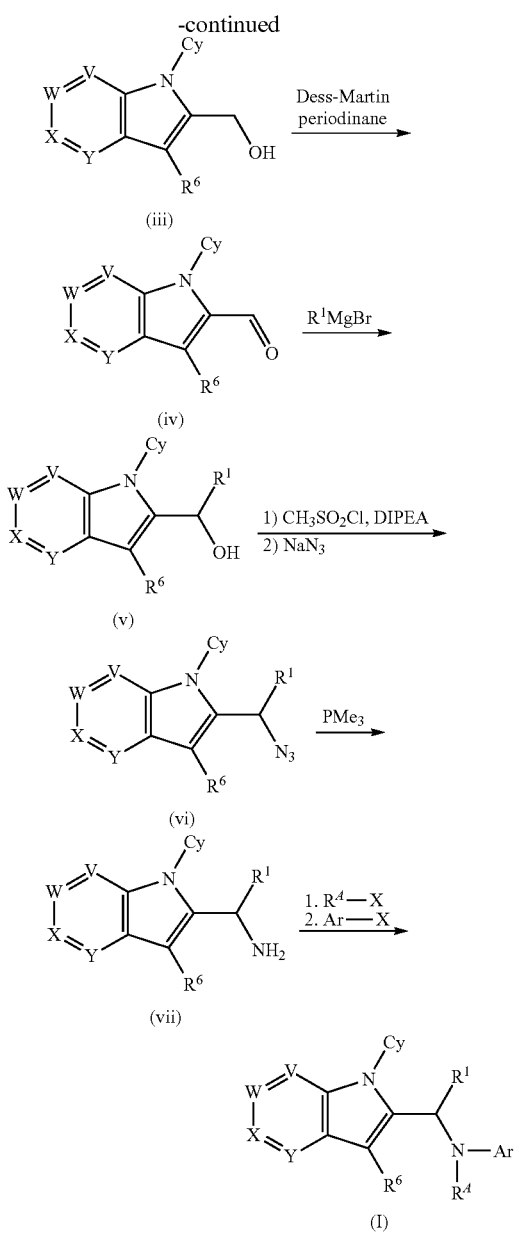

Compounds of Formula (I), wherein Z is $NR^A$, may also be synthesized as shown in Scheme II. Accordingly, a carboxylic acid of formula (a) can be directly activated with a coupling agent (e.g. HBTU, HATU) and then reacted with N,O-dimethylhydroxylamine to give a N-methoxy-N-methylcarboxamide derivative of formula (b). The carboxamide (ii) may then be reacted with a boronoic ester or acid (e.g., a compound of formula Cy-B(OH)$_2$) in the presence of cupric acetate and pyridine to give a compound of formula (c). Compound (c) can then be reacted with a Grignard reagent of formula $R^1$—MgBr to give a ketone of formula (d). The ketone (d) may be reacted with sodium cyanoborohydride in the presence of ammonium acetate to give the amine of formula (e). The amine (e) can be reacted with an appropriate alkylating agent $R^AX$ (e.g., MeI) and then a heteroaryl halide compound (e.g., Ar—X) to give a compound of Formula I. The reaction of amine (e) with $R^A$ can be eliminated to give compounds of Formula I where $R^A$ is H. Alternatively, the ketone (d) can be reduced to give an alcohol of formula (f) which can be converted to a compound of Formula I by substituting it for the compound of formula (v) in Scheme I.

Scheme II

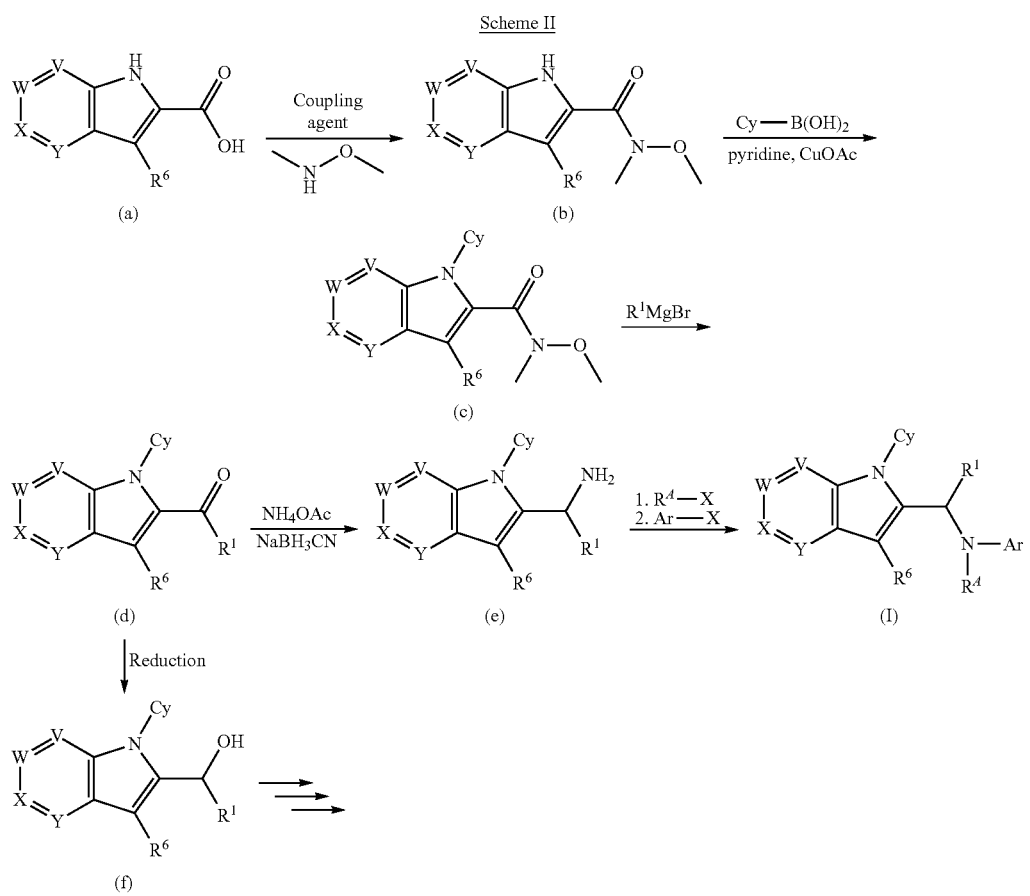

Compounds of Formula I, wherein $R^6$ is halogen, can also be synthesized as shown in Scheme III. Accordingly, the amine of formula (e) from Scheme II is first protected to give a Boc derivative of formula (g). The Boc derivative (g) can then be reacted with N-halosuccinimide, wherein $X^1$ is halogen (e.g., bromo, chloro, or iodo) to give a compound of formula (h). The compound of formula (h) can then be deprotected to give an amine compound, which can then be converted to a compound of Formula I using the methods in Scheme I or II (e.g., by substituting the amine compound for the compound of formula (vii) in Scheme I or the compound of formula (e) in Scheme II).

Scheme III

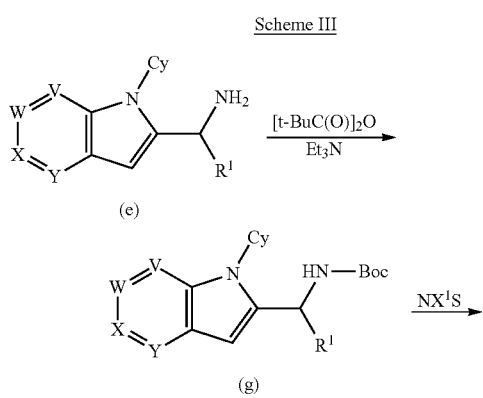

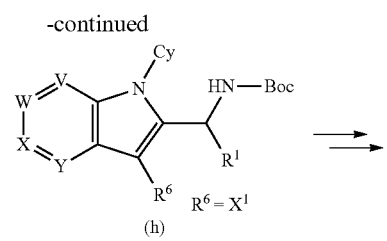

Alternatively, compounds of Formula I, wherein Z is O, S, or a bond, can be synthesized as shown in Scheme IV. The hydroxyl group of the compound of formula (v) from Scheme I or the compound of formula (f) from Scheme II can be transformed to a thiol group by activation with mesyl chloride to form a mesylate compound of formula (b-1), followed by conversion to the thioacetate and cleavage of the acetate to afford a thiol compound of formula (b-2). The hydroxyl compound (from Scheme I or II) or the thiol compound (b-2) can be reacted with an appropriate heteroaryl halide compound (e.g., Ar—Br) to give a compound of formula (a-1) or (b-3), respectively, with or without a catalyst. Alternatively, the mesylate (b-1) can be reacted with aryl or heteroaryl thiol (e.g., Ar—SH) to give a compound of formula (b-3). The mesylate (b-1) can also be reacted with a heteroaryl compound (e.g., Ar—H, wherein H is attached to a nitrogen atom in Ar) to give a compound of formula (b-4).

Scheme IV

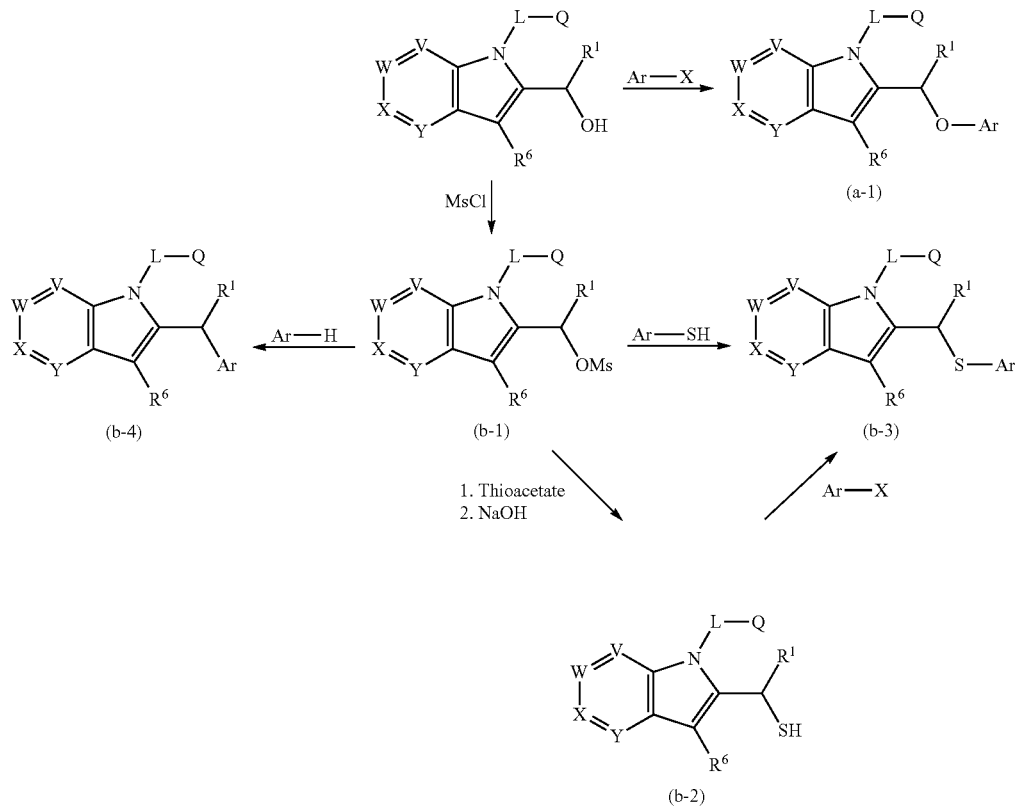

Compounds of Formula I, wherein Cy is heterocycloalkyl or cycloalkyl, can be synthesized as shown in Scheme V. Appropriate indole compound, for example compound (b) from Scheme II, can be reacted with Cy-X (X is a leaving group such as a bromine or tosylate, mesylate) in the presence of a suitable base (such as sodium hydride, potassium butoxide, or potassium hydroxide) in a suitable solvent (such as DMF or DMSO) to give compound (c). The latter can then be converted to compounds of Formula I, wherein Cy is heterocycloalkyl or cycloalkyl, as shown in Scheme II. Alternatively, compound (c) can be reacted with an allyl carbonate or allyl acetate (i) in the presence of a suitable palladium catalyst such as $Pd_2(dba)_3$, and a suitable ligand such as (1R,2R)-(+)-1,2-diaminocyclohexane-N,N'-bis(2-diphenylphosphinobenzoyl) to yield compound (k). Compound (c) can also be treated with vinyl triflate (l) under cross coupling conditions to give compound (m). Compound (k) and (m) can then be hydrogenated to compound (n), which can be further transformed to a compound of Formula I.

Scheme V

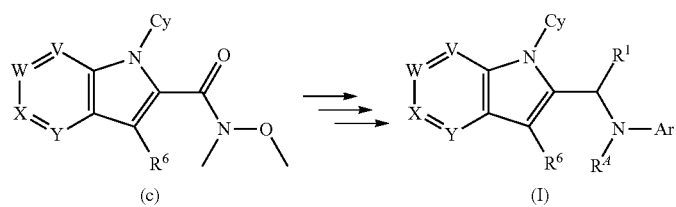

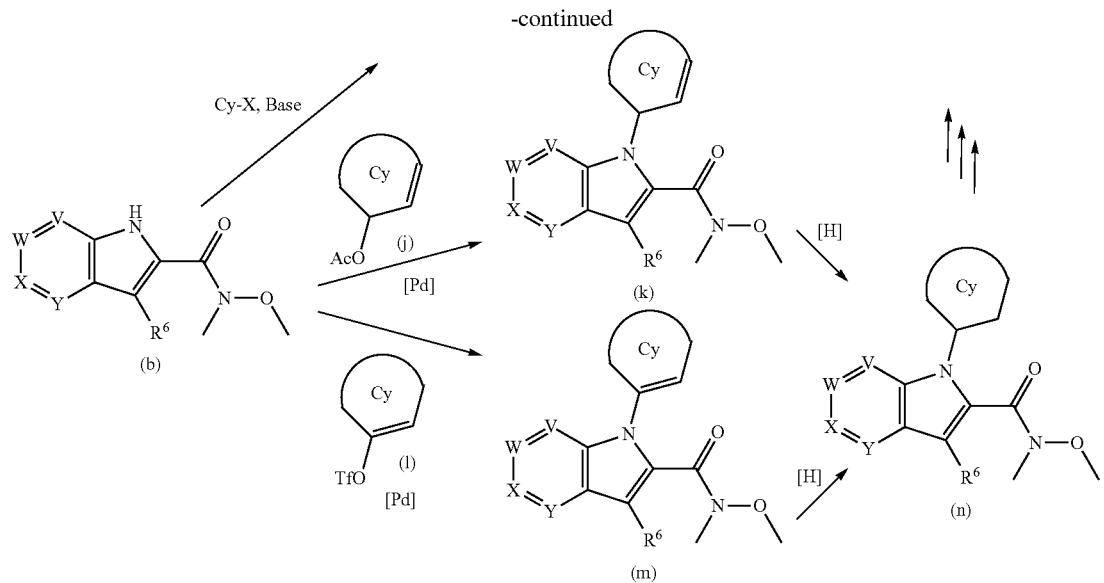

Compounds with Formulary I, wherein Cy is heterocycloalkyl, can also be prepared by methods analogous to those in Scheme VI. Compound (b) can be converted to compound (o) through coupling with a pyridine boronic acid in the presence of copper(II) acetate or Ulman-type coupling with pyridine iodide in the presence of copper or other modified catalyst. The pyridine ring in compound (o) can then be transformed to a saturated heterocycloalkyl by reaction with an acid chloride or chlorofomate followed by reduction with sodium boronhydride and then hydrogenation. The resultant compound (p) can be further modified to provide compounds of Formula I with desired substituted hyterocycloalkyl.

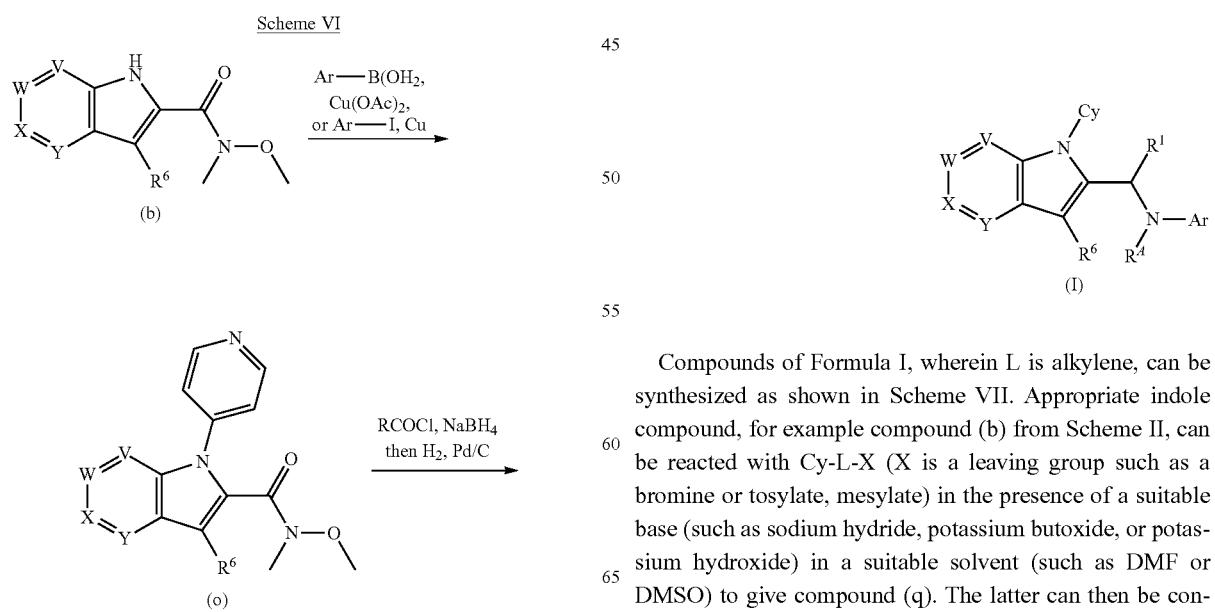

Compounds of Formula I, wherein L is alkylene, can be synthesized as shown in Scheme VII. Appropriate indole compound, for example compound (b) from Scheme II, can be reacted with Cy-L-X (X is a leaving group such as a bromine or tosylate, mesylate) in the presence of a suitable base (such as sodium hydride, potassium butoxide, or potassium hydroxide) in a suitable solvent (such as DMF or DMSO) to give compound (q). The latter can then be converted to compounds of Formula I, wherein L is alkylene.

Scheme VII

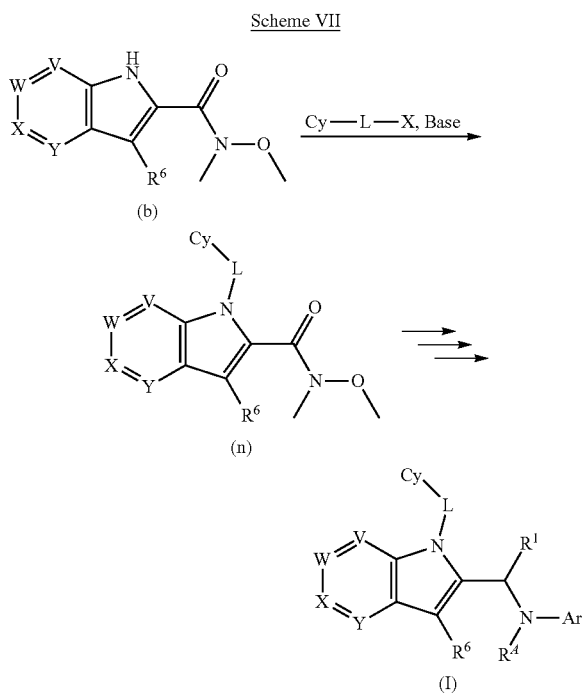

Compounds of Formula I, wherein Z is a bond, can be synthesized as shown in Scheme VIII. The hydroxyl group of the compound of formula (v) from Scheme I or the compound of formula (f) from Scheme II can be transformed to a leaving group (e.g. MsO or Br) by activation with mesyl chloride or conversion to halogen directly. The resulting compound (r) can then react with a heteroaryl with a nucleophilic group, for example 6-aminopurine, to give the desired compound of Formula I wherein Z is a bond.

Scheme VIII

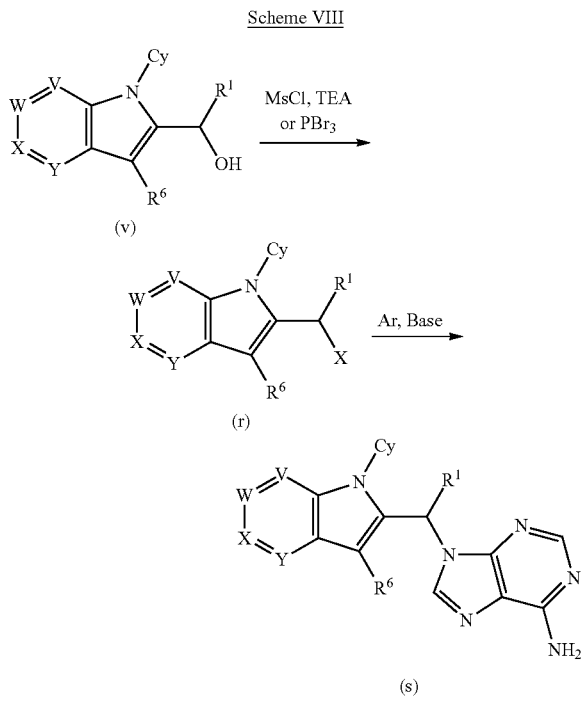

Methods

The compounds of the invention can modulate activity of one or more of various kinases including, for example, phosphoinositide 3-kinases (PI3Ks). The term "modulate" is meant to refer to an ability to increase or decrease the activity of one or more members of the PI3K family. Accordingly, the compounds of the invention can be used in methods of modulating a PI3K by contacting the PI3K with any one or more of the compounds or compositions described herein. In some embodiments, compounds of the present invention can act as inhibitors of one or more PI3Ks. In further embodiments, the compounds of the invention can be used to modulate activity of a PI3K in an individual in need of modulation of the receptor by administering a modulating amount of a compound of the invention, or a pharmaceutically acceptable salt thereof. In some embodiments, modulating is inhibiting.

Given that cancer cell growth and survival is impacted by multiple signaling pathways, the present invention is useful for treating disease states characterized by drug resistant kinase mutants. In addition, different kinase inhibitors, exhibiting different preferences in the kinases which they modulate the activities of, may be used in combination. This approach could prove highly efficient in treating disease states by targeting multiple signaling pathways, reduce the likelihood of drug-resistance arising in a cell, and reduce the toxicity of treatments for disease.

Kinases to which the present compounds bind and/or modulate (e.g., inhibit) include any member of the PI3K family. In some embodiments, the PI3K is PI3Kα, PI3Kβ, PI3Kγ, or PI3Kδ. In some embodiments, the PI3K is PI3Kγ or PI3Kδ. In some embodiments, the PI3K is PI3Kγ. In some embodiments, the PI3K is PI3Kδ. In some embodiments, the PI3K includes a mutation. A mutation can be a replacement of one amino acid for another, or a deletion of one or more amino acids. In such embodiments, the mutation can be present in the kinase domain of the PI3K.

In some embodiments, more than one compound of the invention is used to inhibit the activity of one kinase (e.g., PI3Kγ or PI3Kδ).

In some embodiments, more than one compound of the invention is used to inhibit more than one kinase, such as at least two kinases (e.g., PI3Kγ and PI3Kδ).

In some embodiments, one or more of the compounds is used in combination with another kinase inhibitor to inhibit the activity of one kinase (e.g., PI3Kγ or PI3Kδ).

In some embodiments, one or more of the compounds is used in combination with another kinase inhibitor to inhibit the activities of more than one kinase (e.g., PI3Kγ or PI3Kδ), such as at least two kinases.

The compounds of the invention can be selective. By "selective" is meant that the compound binds to or inhibits a kinase with greater affinity or potency, respectively, compared to at least one other kinase. In some embodiments, the compounds of the invention are selective inhibitors of PI3Kγ or PI3Kδ over PI3Kα and/or PI3Kβ. In some embodiments, the compounds of the invention are selective inhibitors of PI3Kδ (e.g., over PI3Kα, PI3Kβ and PI3Kγ). In some embodiments, the compounds of the invention are selective inhibitors of PI3Kγ (e.g., over PI3Kα, PI3Kβ and PI3Kδ). In some embodiments, selectivity can be at least about 2-fold, 5-fold, 10-fold, at least about 20-fold, at least about 50-fold, at least about 100-fold, at least about 200-fold, at least about 500-fold or at least about 1000-fold. Selectivity can be measured by methods routine in the art. In some embodiments, selectivity can be tested at the $K_m$ ATP concentration of each enzyme. In some embodiments, the selectivity of compounds of the invention can be determined by cellular assays associated with particular PI3K kinase activity.

Another aspect of the present invention pertains to methods of treating a kinase (such as PI3K)-associated disease or disorder in an individual (e.g., patient) by administering to the individual in need of such treatment a therapeutically effective amount or dose of one or more compounds of the present invention or a pharmaceutical composition thereof. A PI3K-associated disease can include any disease, disorder or condition that is directly or indirectly linked to expression or activity of the PI3K, including overexpression and/or abnormal activity levels. In some embodiments, the disease can be linked to Akt (protein kinase B), mammalian target of rapamycin (mTOR), or phosphoinositide-dependent kinase 1 (PDK1). In some embodiments, the mTOR-related disease can be inflammation, atherosclerosis, psoriasis, restenosis, benign prostatic hypertrophy, bone disorders, pancreatitis, angiogenesis, diabetic retinopathy, arthritis, immunological disorders, kidney disease, or cancer. A PI3K-associated disease can also include any disease, disorder or condition that can be prevented, ameliorated, or cured by modulating PI3K activity. In some embodiments, the disease is characterized by the abnormal activity of PI3K. In some embodiments, the disease is characterized by mutant PI3K. In such embodiments, the mutation can be present in the kinase domain of the PI3K.

Examples of PI3K-associated diseases include immune-based diseases involving the system including, for example, rheumatoid arthritis, allergy, asthma, glomerulonephritis, lupus, or inflammation related to any of the above.

Further examples of PI3K-associated diseases include cancers such as breast, prostate, colon, endometrial, brain, bladder, skin, uterus, ovary, lung, pancreatic, renal, gastric, or hematological cancer.

In some embodiments, the hematological cancer is acute myeloblastic leukemia (AML) or chronic myeloid leukemia (CML), or B cell lymphoma.

Further examples of PI3K-associated diseases include lung diseases such as acute lung injury (ALI) and adult respiratory distress syndrome (ARDS).

Further examples of PI3K-associated diseases include osteoarthritis, restenosis, atherosclerosis, bone disorders, arthritis, diabetic retinopathy, psoriasis, benign prostatic hypertrophy, inflammation, angiogenesis, pancreatitis, kidney disease, inflammatory bowel disease, myasthenia gravis, multiple sclerosis, or Sjögren's syndrome, and the like.

As used herein, the term "contacting" refers to the bringing together of indicated moieties in an in vitro system or an in vivo system. For example, "contacting" a PI3K with a compound of the invention includes the administration of a compound of the present invention to an individual or patient, such as a human, having a PI3K, as well as, for example, introducing a compound of the invention into a sample containing a cellular or purified preparation containing the PI3K.

As used herein, the term "individual" or "patient," used interchangeably, refers to any animal, including mammals, preferably mice, rats, other rodents, rabbits, dogs, cats, swine, cattle, sheep, horses, or primates, and most preferably humans As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some embodiments, the dosage of the compound, or a pharmaceutically acceptable salt thereof, administered to a patient or individual is about 1 mg to about 2 g, or about 50 mg to about 500 mg.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, as well as Bcr-Abl, Flt-3, EGFR, HER2, JAK, c-MET, VEGFR, PDGFR, cKit, IGF-1R, RAF and FAK kinase inhibitors such as, for example, those described in WO 2006/056399, or other agents such as, therapeutic antibodies can be used in combination with the compounds of the present invention for treatment of PI3K-associated diseases, disorders or conditions. The one or more additional pharmaceutical agents can be administered to a patient simultaneously or sequentially.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present invention and are presented as a non limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, Iressa, Tarceva, antibodies to EGFR, Gleevec™, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, ELOXATIN™, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225, Campath, Clofarabine, cladribine, aphidicolon, rituxan, sunitinib, dasatinib, tezacitabine, Sml1, fludarabine, pentostatin, triapine, didox, trimidox, amidox, 3-AP, and MDL-101,731.

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the compounds of the invention can be used in combination with one or more other kinase inhibitors including imatinib, particularly for treating patients resistant to imatinib or other kinase inhibitors.

In some embodiments, the compounds of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a PI3K inhibitor of the present invention with an additional agent. Furthermore, resistance of multiple myeloma cells to agents such as dexamethasone may be reversible upon treatment with the PI3K inhibitor of the present invention. The agents can be combined with the present compound in a single or continuous dosage form, or the agents can be administered simultaneously or sequentially as separate dosage forms.

In some embodiments, a corticosteroid such as dexamethasone is administered to a patient in combination with the compounds of the invention where the dexamethasone is administered intermittently as opposed to continuously.

In some embodiments, the compound is administered in combination with a kinase inhibitor that inhibits a kinase other than a PI3K kinase.

In some further embodiments, combinations of the compounds of the invention with other therapeutic agents can be administered to a patient prior to, during, and/or after a bone marrow transplant or stem cell transplant.

Pharmaceutical Formulations and Dosage Forms

In some embodiments, the present invention provides a composition comprising a compound of the invention, or a pharmaceutically acceptable salt thereof, and at least one pharmaceutically acceptable carrier. When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the invention contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the invention contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the invention.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating PI3K in tissue samples, including human, and for identifying PI3K ligands by inhibition binding of a labeled compound. Accordingly, the present invention includes PI3K assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2H$ (also written as D for deuterium), $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro PI3K labeling and competition assays, compounds that incorporate $^3H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^3H$, $^{14}C$, $^{125}I$, $^{35}S$ and $^{82}Br$.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a PI3K by monitoring its concentration variation when contacting with the PI3K, through tracking of the labeling. For example, a test compound (labeled) can be evaluated for its ability to reduce binding of another compound which is known to bind to a PI3K (i.e., standard compound). Accordingly, the ability of a test compound to compete with the standard compound for binding to the PI3K directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of PI3K-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be PI3K inhibitors according to at least one assay described herein.

EXAMPLES

The example compounds below containing one or more chiral centers were obtained in racemate form or as isomeric mixtures, unless otherwise specified.

Example 1

N-{1-[6-Chloro-1-(3-fluorophenyl)-1H-indol-2-yl]ethyl}-9H-purin-6-amine trifluoroacetate

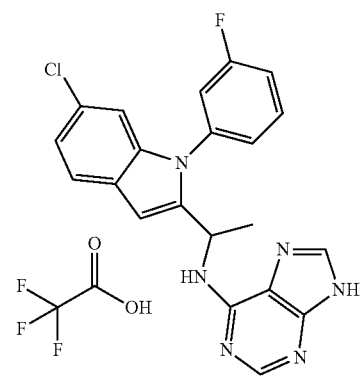

Step 1. Ethyl 6-chloro-1-(3-fluorophenyl)-1H-indole-2-carboxylate

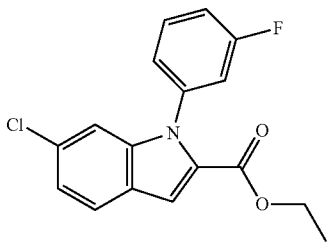 [SMILES: CCOC(=O)c1cc2ccc(Cl)cc2n1-c1cccc(F)c1]

Activated molecular sieves (8.9 g) 4 Å were placed in an oven dried round bottom flask and cooled to room temperature under nitrogen. Ethyl 6-chloro-1H-indole-2-carboxylate (from AsymChem, 0.500 g, 2.24 mmol), (3-fluorophenyl)boronic acid (0.938 g, 6.71 mmol), copper acetate (0.40 g, 3.3 mmol), methylene chloride (80 mL) was added to the flask, followed by pyridine (0.723 mL, 8.94 mmol). The reaction mixture was stirred at room temperature for 2 days, and then filtered through Celite. The filtrate was concentrated under reduced pressure. The resultant residue was purified by chromatography on silica gel (eluting with 0 to 50% EtOAc in hexane) to give the desired product (0.60 g). LCMS calculated for $C_{17}H_{14}ClFNO_2(M+H)^+$: m/z=318.1. Found: 318.1.

Step 2. [6-Chloro-1-(3-fluorophenyl)-1H-indol-2-yl]methanol

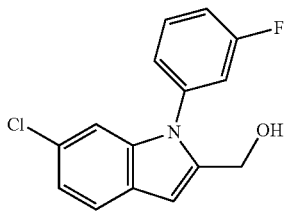 [SMILES: OCc1cc2ccc(Cl)cc2n1-c1cccc(F)c1]

A solution of ethyl 6-chloro-1-(3-fluorophenyl)-1H-indole-2-carboxylate (0.60 g, 1.9 mmol) in tetrahydrofuran (10 mL) was cooled at −78° C. Lithium tetrahydroaluminate (1 M) in tetrahydrofuran (6.0 mL, 6.0 mmol) was added dropwise and the resulting mixture was stirred at this temperature for 1 hour. The reaction was quenched by the addition of water (0.12 mL) and stirred for 10 minutes, warmed up to room temperature, followed by the addition of 5% aqueous NaOH solution (0.12 mL) with stirring for 10 minutes. Then additional water (0.36 mL) was added and stirring was continued for 10 minutes. The mixture was filtered, dried over $MgSO_4$ and concentrated to give the crude product (0.53 g). The residue was used in the next step directly. LCMS calculated for $C_{15}H_{12}ClFNO(M+H)^+$: m/z=276.1. Found: 276.0.

Step 3. 6-Chloro-1-(3-fluorophenyl)-1H-indole-2-carbaldehyde

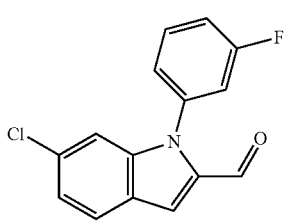 [SMILES: O=Cc1cc2ccc(Cl)cc2n1-c1cccc(F)c1]

Dess-Martin periodinane (1.3 g, 2.9 mmol) was added to a solution of [6-chloro-1-(3-fluorophenyl)-1H-indol-2-yl] methanol (0.53 g, 1.9 mmol) in methylene chloride (10 mL). The solution was stirred at room temperature for 2 hours. The reaction mixture was diluted with dichloromethane, washed with 1:1 aqueous saturated $Na_2S_2O_3$ and $NaHCO_3$. The organic layers were dried over $MgSO_4$, concentrated and purified on silica gel (eluting with 0-20% EtOAc in hexane) to give the desired product (50 mg). LCMS calculated for $C_{15}H_{10}ClFNO(M+H)^+$: m/z=274.0. Found: 274.0.

Step 4. 1-[6-Chloro-1-(3-fluorophenyl)-1H-indol-2-yl]ethanol

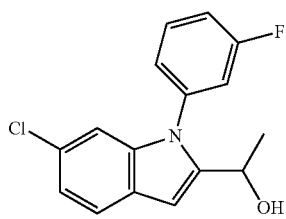 [SMILES: CC(O)c1cc2ccc(Cl)cc2n1-c1cccc(F)c1]

To a mixture of 6-chloro-1-(3-fluorophenyl)-1H-indole-2-carbaldehyde (50 mg, 0.18 mmol) in tetrahydrofuran (5 mL) was added 3.0 M methylmagnesium bromide in ether (0.091 mL, 0.27 mmol). The reaction was stirred at room temperature for 1 hour, quenched with water, and then extracted with ethyl acetate (EtOAc). The combined organic layers were washed with brine, dried over $MgSO_4$ and concentrated to give the desired product (51 mg). The crude product was used directly in next step. LCMS calculated for $C_{16}H_{14}ClFNO(M+H)^+$: m/z=290.1. Found: 289.7.

Step 5. 2-(1-azidoethyl)-6-chloro-1-(3-fluorophenyl)-1H-indole

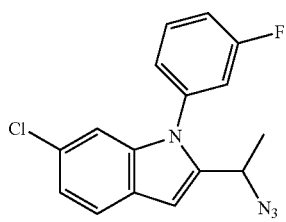 [SMILES: CC(N=[N+]=[N-])c1cc2ccc(Cl)cc2n1-c1cccc(F)c1]

To a mixture of 1-[6-chloro-1-(3-fluorophenyl)-1H-indol-2-yl]ethanol (51 mg, 0.18 mmol) and N,N-diisopropylethylamine (0.046 mL, 0.26 mmol) in dichloromethane (3 mL) was added methanesulfonyl chloride (0.018 mL, 0.23 mmol). The reaction was stirred at room temperature for 1 hour, quenched with water, and then extracted with dichloromethane. The organic layers were combined, washed with brine, dried over $MgSO_4$ and concentrated to give corresponding mesylate. LCMS $[M-MsO]^+$ m/z=272.0.

To the crude 1-[6-chloro-1-(3-fluorophenyl)-1H-indol-2-yl]ethyl methanesulfonate in N,N-dimethylformamide (1 mL) was added sodium azide (57 mg, 0.88 mmol). The reaction was stirred at room temperature for 2 hours, quenched with water, and then extracted with EtOAc. The extracts were combined, washed with brine, dried over $MgSO_4$ and concentrated to give the desired azide (55 mg), which was used directly in the next step. LCMS calculated for C₁₆H₁₂ClFN (M-N₃)⁺: m/z=272.1. Found: 271.9.

Step 6. 1-[6-Chloro-1-(3-fluorophenyl)-1H-indol-2-yl]ethanamine

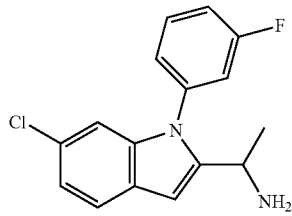 [SMILES: CC(N)c1cc2ccc(Cl)cc2n1-c1cccc(F)c1]

To a solution of 2-(1-azidoethyl)-6-chloro-1-(3-fluorophenyl)-1H-indole (55 mg, 0.17 mmol) in tetrahydrofuran (2 mL) was added 1.00 M of trimethylphosphine in tetrahydrofuran (0.26 mL, 0.26 mmol) and the resultant mixture was stirred at room temperature for 1 hour. The mixture was concentrated to give the desired amine (50 mg). The crude product was used directly in the next step. LCMS calculated for C₁₆H₁₂ClFN(M-NH₂)⁺: m/z=272.1. Found: 272.0.

Step 7. N-{1-[6-Chloro-1-(3-fluorophenyl)-1H-indol-2-yl]ethyl}-9H-purin-6-amine

A mixture of 1-[6-chloro-1-(3-fluorophenyl)-1H-indol-2-yl]ethanamine (50 mg, 0.17 mmol), 6-bromo-9H-purine (52 mg, 0.26 mmol) and N,N-diisopropylethylamine (0.060 mL, 0.35 mmol) in ethanol (0.5 mL) was heated at 110° C. overnight. The mixture was cooled and then filtered. The filtrate was purified on preparative-LCMS (XBridge C18 column, 19×100 mm, 5 μM; eluting with a gradient of acetonitrile/water containing 01.% TFA; at flow rate 30 mL/min; with injection volume of 2 mL) to give the desired product as a TFA salt. LCMS calculated for C₂₁H₁₇ClFN₆(M+H)⁺: m/z=407.1. Found: 407.0.

Example 2

N-{1-[4-Chloro-1-(3-fluorophenyl)-1H-indol-2-yl]ethyl}-9H-purin-6-amine trifluoroacetate

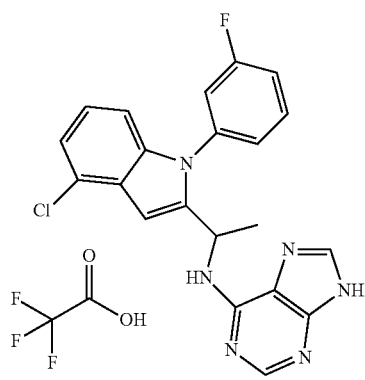 [SMILES: O=C(O)C(F)(F)F ; CC(Nc1ncnc2[nH]cnc12)c1cc2c(Cl)cccc2n1-c1cccc(F)c1]

Step 1. 4-Chloro-N-methoxy-N-methyl-1H-indole-2-carboxamide

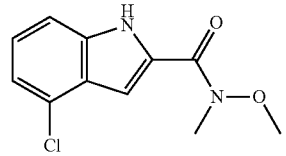 [SMILES: CON(C)C(=O)c1cc2c(Cl)cccc2[nH]1]

A mixture of 4-chloro-1H-indole-2-carboxylic acid (from Ryan Scientific, 1.0 g, 5.1 mmol), O-(benzotriazol-1-yl)-N,N,N',N'-tetramethyluronium hexafluorophosphate (2.9 g, 7.7 mmol) and triethylamine (3.6 mL, 26 mmol) in N,N-dimethylformamide (15 mL) was stirred at room temperature for 10 minutes. N,O-Dimethylhydroxylamine hydrochloride (0.75 g, 7.7 mmol) was added and the resulting suspension was stirred at room temperature overnight. The mixture was quenched with water and then extracted with EtOAc. The combined organic layers were dried over MgSO₄, concentrated and purified on silica gel (eluting with 0-35% EtOAc in hexane) to give the desired product (0.35 g, 29%). LCMS calculated for C₁₁H₁₂ClN₂O₂(M+H)⁺: m/z=239.1. Found: 239.1.

Step 2. 4-Chloro-1-(3-fluorophenyl)-N-methoxy-N-methyl-1H-indole-2-carboxamide

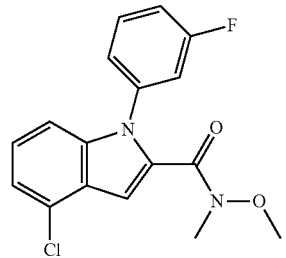 [SMILES: CON(C)C(=O)c1cc2c(Cl)cccc2n1-c1cccc(F)c1]

Activated molecular sieves (4.9 g) 4 Å were placed in an oven dried flask and cooled to room temperature under nitrogen. To the flask was charged with 4-chloro-N-methoxy-N-methyl-1H-indole-2-carboxamide (0.35 g, 1.5 mmol), (3-fluorophenyl)boronic acid (0.62 g, 4.4 mmol) and cupric acetate (0.40 g, 2.2 mmol), methylene chloride (65 mL) and then pyridine (0.47 mL, 5.9 mmol). The reaction mixture was stirred at room temperature overnight, then filtered through a pad of Celite. The filtrate was concentrated and purified on silica gel (eluting with 0-20% EtOAc in hexane) to give the desired product (0.44 g, 90%). LCMS calculated for C₁₇H₁₅ClFN₂O₂(M+H)⁺: m/z=333.1. Found: 333.0.

Step 3. 1-[4-Chloro-1-(3-fluorophenyl)-1H-indol-2-yl]ethanone

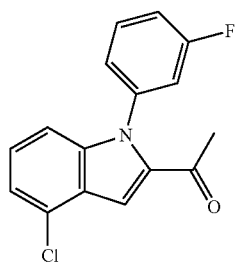 [SMILES: CC(=O)c1cc2c(Cl)cccc2n1-c1cccc(F)c1]

To a mixture of 4-chloro-1-(3-fluorophenyl)-N-methoxy-N-methyl-1H-indole-2-carboxamide (0.44 g, 1.3 mmol) in tetrahydrofuran (10 mL) was added 1.4 M methylmagnesium bromide in tetrahydrofuran (4.7 mL, 6.6 mmol) dropwise. The reaction was stirred at room temperature overnight, then quenched with aqueous saturated NH$_4$Cl solution and extracted with EtOAc. The extracts were dried over MgSO$_4$, concentrated and purified on silica gel (eluting with 0-10% EtOAc in hexane) to give the desired product (0.26 g, 68%). LCMS calculated for C$_{16}$H$_{12}$ClFNO(M+H)$^+$: m/z=288.1. Found: 288.0.

Step 4. 1-[4-Chloro-1-(3-fluorophenyl)-1H-indol-2-yl]ethanamine

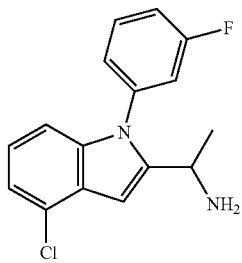 [SMILES: CC(N)c1cc2c(Cl)cccc2n1-c1cccc(F)c1]

A mixture of 1-[4-chloro-1-(3-fluorophenyl)-1H-indol-2-yl]ethanone (0.13 g, 0.45 mmol) and ammonium acetate (0.348 g, 4.52 mmol) in methanol (2.0 mL) and acetonitrile (2.0 mL) was heated at 65° C. in a sealed tube for 30 minutes. After cooling to room temperature, to the resultant mixture was added sodium cyanoborohydride (57 mg, 0.91 mmol). The reaction was heated at 65° C. for another 4 hours. After cooling to room temperature, the reaction was quenched with aqueous saturated NaHCO$_3$ solution and then extracted with dichloromethane. The combined organic layers were dried over MgSO$_4$ and concentrated to give the desired product (0.11 g), which was used directly in the next step. LCMS calculated for C$_{16}$H$_{12}$ClFN(M-NH$_2$)$^+$: m/z=272.1. Found: 272.0.

Step 5. N-{1-[4-Chloro-1-(3-fluorophenyl)-1H-indol-2-yl]ethyl}-9H-purin-6-amine

A mixture of 1-[4-chloro-1-(3-fluorophenyl)-1H-indol-2-yl]ethanamine (0.11 g, 0.38 mmol), 6-bromo-9H-purine (0.11 g, 0.57 mmol) and N,N-diisopropylethylamine (0.20 mL, 1.1 mmol) in ethanol (1.5 mL) was heated at 110° C. overnight. The mixture was filtered and the filtrate was purified on preparative-LCMS (XBridge C18 column, 19×100 mm, 5 μM; eluting with a gradient of acetonitrile/water containing 01.% TFA; at flow rate 30 mL/min; with injection volume of 2 mL) to give the desired product as a TFA salt. LCMS calculated for C$_{21}$H$_{17}$ClFN$_6$(M+H)$^+$: m/z=407.2. Found: 407.0. $^1$H NMR (DMSO-d$_6$, 400 MHz) δ 8.81 (1H, br s), 8.36 (1H, s), 8.31 (1H, m), 7.51 (1H, m), 7.35 (1H, m), 7.20 (1H, m), 7.16 (1H, d, J=7.6 Hz), 7.09 (1H, dd, J=8.0 and 7.6 Hz), 6.96 (1H, d, J=8.0 Hz), 6.78 (1H, s), 5.58 (1H, m), 1.60 (3H, d, J=6.4 Hz) ppm. $^{19}$F NMR (DMSO-d$_6$, 376.3 MHz) for the TFA salt: δ −74.7, −111.4 (0.5 F) and −112.0 (0.5 F) ppm.

Example 3

N-{1-[3-Chloro-1-(3-fluorophenyl)-1H-indol-2-yl]ethyl}-9H-purin-6-amine trifluoroacetate

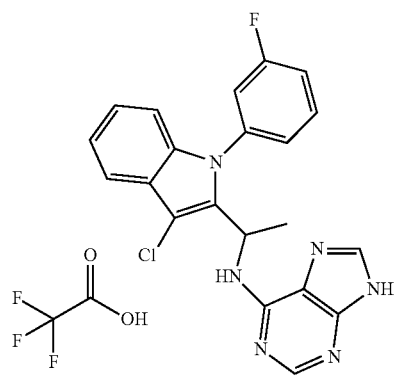

Step 1.
N-Methoxy-N-methyl-1H-indole-2-carboxamide

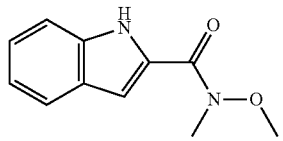

A mixture of 1H-indole-2-carboxylic acid (from Aldrich, 2.5 g, 16 mmol), O-(benzotriazol-1-yl)-N,N,N',N'-tetramethyluronium hexafluorophosphate (7.6 g, 20 mmol) and triethylamine (11 mL, 78 mmol) in N,N-dimethylformamide (20 mL) was stirred at room temperature for 10 minutes. N,O-Dimethylhydroxylamine hydrochloride (2.0 g, 20 mmol) was added and the resulting suspension was stirred at room temperature for 2 hours. The mixture was quenched with water, extracted with EtOAc. The combined organic layers were dried over Na$_2$SO$_4$, concentrated and purified on silica gel (eluting with 0-50% EtOAc in hexane) to give the desired product (2.7 g, 85%). LCMS calculated for C$_{11}$H$_{13}$N$_2$O$_2$(M+H)$^+$: m/z=205.1. Found: 205.1.

Step 2. 1-(3-Fluorophenyl)-N-methoxy-N-methyl-1H-indole-2-carboxamide

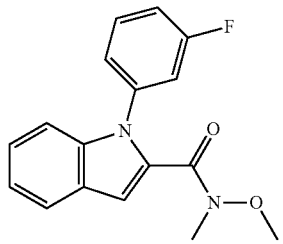 [SMILES: CON(C)C(=O)c1cc2ccccc2n1-c1cccc(F)c1]

Activated molecular sieves (6.0 g) 4 Å were placed in an oven dried flask and cooled to room temperature under nitrogen. To the flask was charged with N-methoxy-N-methyl-1H-indole-2-carboxamide (0.45 g, 2.2 mmol), (3-fluorophenyl) boronic acid (0.94 g, 6.7 mmol), cupric acetate (0.60 g, 3.3 mmol), and methylene chloride (80 mL) and then pyridine (0.72 mL, 8.9 mmol). The reaction mixture was stirred at room temperature over weekend, then filtered through a pad of Celite. The filtrate was concentrated and purified on silica gel (eluting with 0-25% EtOAc in hexane) to give the title compound (0.30 g, 46%). LCMS calculated for $C_{17}H_{16}FN_2O_2(M+H)^+$: m/z=299.1. Found: 299.0.

Step 3.
1-[1-(3-Fluorophenyl)-1H-indol-2-yl]ethanone

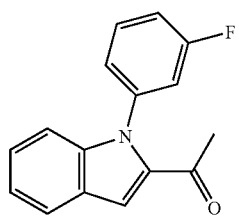 [SMILES: CC(=O)c1cc2ccccc2n1-c1cccc(F)c1]

To a mixture of 1-(3-fluorophenyl)-N-methoxy-N-methyl-1H-indole-2-carboxamide (0.30 g, 1.0 mmol) in tetrahydrofuran (6 mL) was added 1.4 M methylmagnesium bromide in tetrahydrofuran (1.1 mL, 1.5 mmol). The reaction was stirred at room temperature for 2 hours, then quenched with saturated $NH_4Cl$ solution, extracted with EtOAc. The combined organic layers were washed with brine, dried over $MgSO_4$ and concentrated to give the desired product (0.27 g). The crude product was used directly in next step. LCMS calculated for $C_{16}H_{13}FNO(M+H)^+$: m/z=254.1. Found: 254.1.

Step 4. 1-[1-(3-Fluorophenyl)-1H-indol-2-yl]ethanol

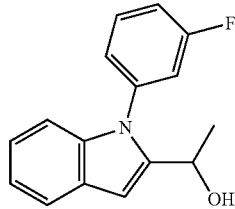 [SMILES: CC(O)c1cc2ccccc2n1-c1cccc(F)c1]

To a mixture of 1-[1-(3-fluorophenyl)-1H-indol-2-yl]ethanone (0.27 g, 1.1 mmol) in methanol (6 mL) was added sodium tetrahydroborate (41 mg, 1.1 mmol). The reaction was stirred at room temperature for 1 hour, quenched with water, and extracted with EtOAc. The combined organic layers were washed with brine, dried over $MgSO_4$ and concentrated to give title compound (0.26 g). The crude product was used directly in the next step. LCMS calculated for $C_{16}H_{13}FN$ $(M-OH)^+$: m/z=238.1. Found: 238.1.

Step 5. 2-(1-Azidoethyl)-1-(3-fluorophenyl)-1H-indole

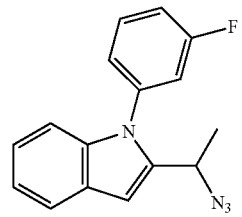 [SMILES: CC(N=[N+]=[N-])c1cc2ccccc2n1-c1cccc(F)c1]

To a mixture of 1-[1-(3-fluorophenyl)-1H-indol-2-yl]ethanol (0.26 g, 1.0 mmol) and N,N-diisopropylethylamine (0.27 mL, 1.5 mmol) in dichloromethane (6 mL) was added methanesulfonyl chloride (0.10 mL, 1.3 mmol). The reaction was stirred at room temperature for 1 hour, quenched with water, and extracted with dichloromethane. The combined extracts were washed with brine, dried over $MgSO_4$ and concentrated to give corresponding mesylate which was used directly in the next step. LCMS $[M-MsO]^+$ m/z=238.1.

To the crude 1-[1-(3-fluorophenyl)-1H-indol-2-yl]ethyl methanesulfonate in N,N-dimethylformamide (5 mL) was added sodium azide (0.20 g, 3.0 mmol). The reaction was stirred at room temperature for 2 hr, quenched with water, and extracted with EtOAc. The combined organic layers were dried over $MgSO_4$, concentrated and purified on silica gel (eluting with 0-30% EtOAc in hexane) to give the desired product (0.14 g, 49%). LCMS calculated for $C_{16}H_{13}FN(M-N_3)^+$: m/z=238.1. Found: 238.1.

Step 6.
1-[1-(3-Fluorophenyl)-1H-indol-2-yl]ethanamine

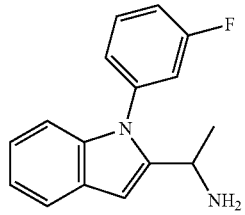 [SMILES: CC(N)c1cc2ccccc2n1-c1cccc(F)c1]

To a solution of 2-(1-azidoethyl)-1-(3-fluorophenyl)-1H-indole (0.14 g, 0.50 mmol) in tetrahydrofuran (3 mL) was added 1.00 M trimethylphosphine in tetrahydrofuran (0.75 mL, 0.75 mmol). The mixture was stirred at room temperature for 1 hour. The mixture was concentrated to give crude product (0.17 g), which was used directly in the next step. LCMS calculated for $C_{16}H_{13}FN(M-NH_2)^+$: m/z=238.1. Found: 238.1.

Step 7. tert-Butyl {1-[1-(3-fluorophenyl)-1H-indol-2-yl]ethyl}carbamate

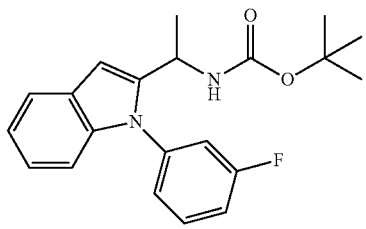 [SMILES: CC(NC(=O)OC(C)(C)C)c1cc2ccccc2n1-c1cccc(F)c1]

Di-tert-butyldicarbonate (0.23 mL, 1.0 mmol) was added to a mixture of 1-[1-(3-fluorophenyl)-1H-indol-2-yl]ethanamine (0.17 g, 0.67 mmol) and triethylamine (0.46 mL, 3.3 mmol) in tetrahydrofuran (3 mL). After 30 minutes, the mixture was quenched with saturated NaHCO$_3$ and extracted with EtOAc. The combined organic layers were dried over MgSO$_4$, concentrated, and purified on silica gel (eluting with 0-20% EtOAc in hexane) to give the desired product (35 mg). LCMS calculated for $C_{21}H_{24}FN_2O_2(M+H)^+$: m/z=355.2. Found: 355.1.

Step 8. tert-Butyl {1-[3-chloro-1-(3-fluorophenyl)-1H-indol-2-yl]ethyl}carbamate

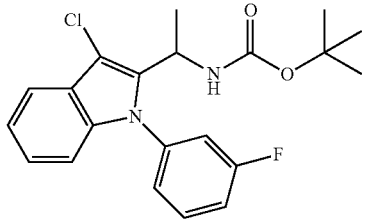 [SMILES: CC(NC(=O)OC(C)(C)C)c1c(Cl)c2ccccc2n1-c1cccc(F)c1]

A solution of N-chlorosuccinimide (0.015 g, 0.11 mmol) in DMF (0.1 mL) was added dropwise to an ice-cooled solution of tert-butyl {1-[1-(3-fluorophenyl)-1H-indol-2-yl]ethyl}carbamate (35 mg, 0.099 mmol) in N,N-dimethylformamide (0.5 mL, 6 mmol). The resulting mixture was allowed to warm to room temperature and stirred for an additional 4 hours. The mixture was then diluted with water and then extracted with EtOAc. The combined organic layers were dried over MgSO$_4$, concentrated, and purified on silica gel (eluting with 0-10% EtOAc in hexane) to give the desired product (36 mg, 94%).

Step 9. 1-[3-Chloro-1-(3-fluorophenyl)-1H-indol-2-yl]ethanamine

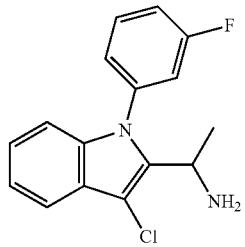 [SMILES: CC(N)c1c(Cl)c2ccccc2n1-c1cccc(F)c1]

Hydrogen chloride (4.0 M) in 1,4-dioxane (0.5 mL, 20 mmol) was added to a solution of tert-butyl {1-[3-chloro-1-(3-fluorophenyl)-1H-indol-2-yl]ethyl}carbamate (36 mg, 0.092 mmol) in 1,4-dioxane (1.0 mL) and the reaction was stirred at room temperature for 1 hour. The mixture was diluted with EtOAc, washed with saturated NaHCO$_3$ solution and water. The combined extracts were dried over MgSO$_4$ and concentrated to give the desired product (31.5 mg). LCMS calculated for $C_{16}H_{12}ClFN(M-NH_2)^+$: m/z=272.1. Found: 272.0.

Step 10. N-{1-[3-Chloro-1-(3-fluorophenyl)-1H-indol-2-yl]ethyl}-9H-purin-6-amine A mixture of 1-[3-chloro-1-(3-fluorophenyl)-1H-indol-2-yl]ethanamine (31 mg, 0.11 mmol), 6-bromo-9H-purine (32 mg, 0.16 mmol) and N,N-diisopropylethylamine (0.056 mL, 0.32 mmol) in ethanol (1.0 mL) was heated at 110° C. overnight. The mixture was filtered and the filtrate was purified on preparative-LCMS (XBridge C18 column, 19×100 mm, 5 μM; eluting with a gradient of acetonitrile/water containing 01.% TFA; at flow rate 30 mL/min; with injection volume of 2 mL) to give the desired product as a TFA salt. LCMS calculated for $C_{21}H_{17}ClFN_6(M+H)^+$: m/z=407.1. Found: 407.0. $^1$H NMR (DMSO-d$_6$, 400 MHz) δ 8.69 (1H, br s), 8.36 (1H, s), 8.33 (1H, m), 7.68 (1H, m), 7.60 (1H, m), 7.47 (1H, m), 7.41 (1H, m), 7.29 (1H, d, J=7.6 Hz), 7.16 (2H, m), 6.98 (1H, m), 5.25 (1H, m), 1.70 (3H, m) ppm. $^{19}$F NMR (DMSO-d$_6$, 376.3 MHz) for the TFA salt: δ −74.6, −111.6 ppm.

Example 4

N-{1-[3,4-Dichloro-1-(3-fluorophenyl)-1H-indol-2-yl]ethyl}-9H-purin-6-amine trifluoroacetate

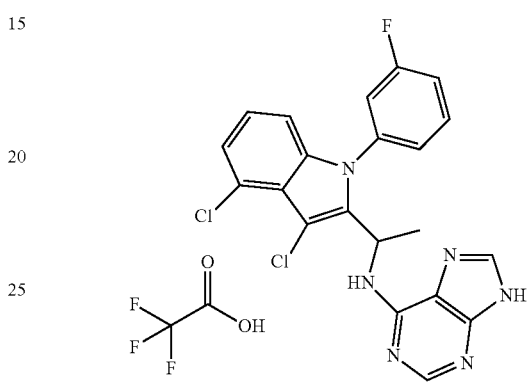

A mixture of N-{1-[4-chloro-1-(3-fluorophenyl)-1H-indol-2-yl]ethyl}-9H-purin-6-amine (40 mg, 0.099 mmol) and N-chlorosuccinimide (15 mg, 0.11 mmol) in N,N-dimethylformamide (0.5 mL) was stirred at room temperature overnight. The mixture was purified with preparative-LCMS (XBridge C18 column, 19×100 mm, 5 μM; eluting with a gradient of acetonitrile/water containing 01.% TFA; at flow rate 30 mL/min; with injection volume of 2 mL) to give the desired product as a TFA salt. LCMS calculated for $C_{21}H_{16}Cl_2FN_6(M+H)^+$: m/z=441.1. Found: 441.0. $^1$H NMR (DMSO-d$_6$, 400 MHz) δ 8.76 (1H, br s), 8.38 (2H, m), 7.71 (1H, m), 7.57 (1H, m), 7.43 (2H, m), 7.12 (2H, m), 6.89 (1H, m), 5.18 (1H, m), 1.71 (3H, m) ppm. $^{19}$F NMR (DMSO-d$_6$, 376.3 MHz) for the TFA salt: δ −74.7, −111.5 (0.5 F), −111.6 (0.5 F) ppm.

Example 5

N-{1-[3-Bromo-1-(3-fluorophenyl)-1H-indol-2-yl]ethyl}-9H-purin-6-amine trifluoroacetate

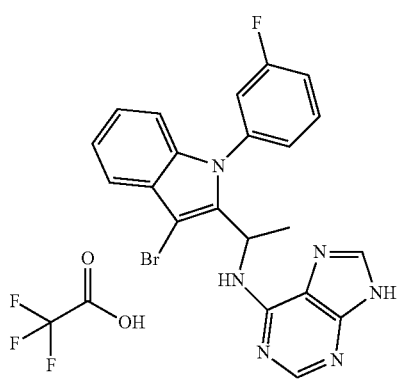

Step 1. 1-(3-Fluorophenyl)-N-methoxy-N-methyl-1H-indole-2-carboxamide

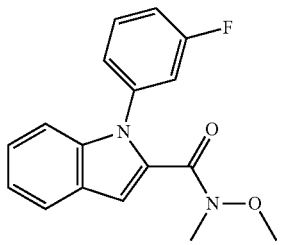 [SMILES: CON(C)C(=O)c1cc2ccccc2n1-c1cccc(F)c1]

Activated molecular sieves (13 g) 4 Å were placed in an oven dried round bottom flask and cooled to room temperature under nitrogen. To the flask was charged with N-methoxy-N-methyl-1H-indole-2-carboxamide (0.97 g, 4.7 mmol), (3-fluorophenyl)-boronic acid (1.5 g, 11 mmol), cupric acetate (1.3 g, 7.3 mmol), methylene chloride (130 mL) and then pyridine (1.5 mL, 19 mmol). The reaction mixture was stirred at room temperature over the weekend. The mixture was filtered through a pad of Celite. The filtrate was concentrated and purified on silica gel (eluting with 0-30% EtOAc/hexane) to give the title compound (0.52 g, 37%). LCMS calculated for $C_{17}H_{16}FN_2O_2(M+H)^+$: m/z=299.1. Found: 299.1.

Step 2. 1-[1-(3-Fluorophenyl)-1H-indol-2-yl]ethanone

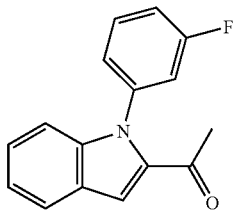 [SMILES: CC(=O)c1cc2ccccc2n1-c1cccc(F)c1]

To a mixture of 1-(3-fluorophenyl)-N-methoxy-N-methyl-1H-indole-2-carboxamide (0.52 g, 1.7 mmol) in tetrahydrofuran (10 mL) was added 3.0 M methylmagnesium bromide in ether (4.6 mL, 0.014 mol). The reaction was stirred at room temperature overnight. The reaction was quenched with saturated NH$_4$Cl solution and extracted with EtOAc. The combined organic layers were washed with water and brine, dried over MgSO$_4$, and concentrated to give crude product (0.4 g, 91%). The crude product was used directly in next step. LCMS calculated for $C_{16}H_{13}FNO(M+H)^+$: m/z=254.1. Found: 254.1.

Step 3. 1-[1-(3-Fluorophenyl)-1H-indol-2-yl]ethanamine

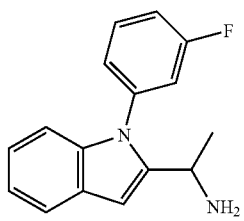

A mixture of 1-[1-(3-fluorophenyl)-1H-indol-2-yl]ethanone (0.40 g, 1.6 mmol) and ammonium acetate (1.22 g, 15.8 mmol) in methanol (5.0 mL) and acetonitrile (5.0 mL) was heated at 65° C. in a sealed tube for 30 minutes. After cooling to room temperature, sodium cyanoborohydride (0.20 g, 3.2 mmol) was added to the resultant mixture. The reaction was heated at 65° C. overnight. The reaction was cooled to room temperature and quenched with saturated NaHCO$_3$ solution and extracted with dichloromethane. The combined organic layers were dried over MgSO$_4$ and concentrated to give crude product (0.39 g, 97%), which was used directly in the next step. LCMS calculated for $C_{16}H_{13}FN$ (M-NH$_2$)$^+$: m/z=238.1. Found: 238.1.

Step 4. tert-Butyl {1-[1-(3-fluorophenyl)-1H-indol-2-yl]ethyl}carbamate

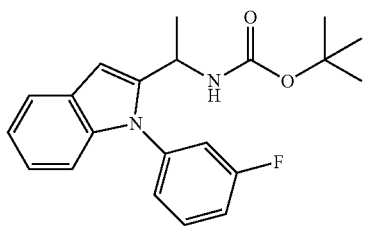 [SMILES: CC(NC(=O)OC(C)(C)C)c1cc2ccccc2n1-c1cccc(F)c1]

Di-tert-butyldicarbonate (1.4 g, 6.4 mmol) was added to a mixture of 1-[1-(3-fluorophenyl)-1H-indol-2-yl]ethanamine (0.39 g, 1.5 mmol) and triethylamine (1.8 mL, 13 mmol) in tetrahydrofuran (8 mL). After 30 min, the mixture was quenched with saturated NaHCO$_3$ solution and extracted with EtOAc. The combined organic layers were washed with brine, dried over MgSO$_4$, concentrated, and purified on silica gel (eluting with 0-20% EtOAc/hexane) to give the desired product (0.41 g, 75%). LCMS calculated for $C_{21}H_{24}FN_2O_2$ (M+H)$^+$: m/z=355.2. Found: 355.1.

Step 5. tert-Butyl {1-[3-bromo-1-(3-fluorophenyl)-1H-indol-2-yl]ethyl}carbamate

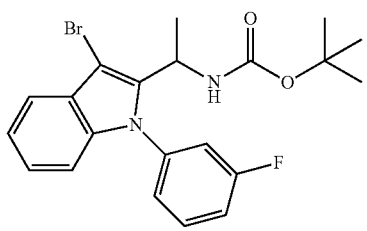 [SMILES: CC(NC(=O)OC(C)(C)C)c1c(Br)c2ccccc2n1-c1cccc(F)c1]

A solution of N-bromosuccinimide (0.24 g, 1.3 mmol) in DMF (1 mL) was added dropwise to an ice-cooled solution of tert-butyl {1-[1-(3-fluorophenyl)-1H-indol-2-yl]ethyl}carbamate (0.41 g, 1.2 mmol) in N,N-dimethylformamide (5 mL) The resulting mixture was allowed to warm to room temperature and stirred for an additional 4 hours. The mixture was diluted with water and extracted with EtOAc. The extracts were combined, dried over MgSO$_4$, concentrated, and purified on silica gel (eluting with 0-10% EtOAc/hexane) to give the desired product (0.34 g, 68%). LCMS calculated for $C_{21}H_{22}BrFN_2O_2Na(M+Na)^+$: m/z=455.1. Found: 455.0.

Step 6. 1-[3-Bromo-1-(3-fluorophenyl)-1H-indol-2-yl]ethanamine

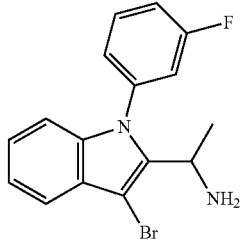 [SMILES: CC(N)c1c(Br)c2ccccc2n1-c1cccc(F)c1]

Hydrogen chloride (4.0 M) in 1,4-dioxane (1.2 mL, 4.8 mmol) was added to a solution of tert-butyl {1-[3-bromo-1-(3-fluorophenyl)-1H-indol-2-yl]ethyl}carbamate (0.15 g, 0.35 mmol) in 1,4-dioxane (2.0 mL) The reaction was stirred at room temperature for 2 hours. The mixture was diluted with EtOAc, washed with saturated NaHCO$_3$ solution, dried over MgSO$_4$ and concentrated to give the crude product (0.12 g). LCMS calculated for C$_{16}$H$_{12}$BrFN (M-NH$_2$)$^+$: m/z=316.0. Found: 316.0.

Step 7. N-{1-[3-Bromo-1-(3-fluorophenyl)-1H-indol-2-yl]ethyl}-9H-purin-6-amine trifluoroacetate A mixture of 1-[3-bromo-1-(3-fluorophenyl)-1H-indol-2-yl]ethanamine (0.12 g, 0.36 mmol), 6-bromo-9H-purine (0.11 g, 0.54 mmol) and N,N-diisopropylethylamine (0.19 mL, 1.1 mmol) in ethanol (2.0 mL) was heated at 110° C. overnight. The mixture was filtered, and the filtrate was purified on preparative-LCMS (XBridge C18 column, 19×100 mm, 5 µM; eluting with a gradient of acetonitrile/water containing 01.% TFA; at flow rate 30 mL/min; with injection volume of 2 mL) to give the desired compound as a TFA salt. LCMS calculated for C$_{21}$H$_{17}$BrFN$_6$ (M+H)$^+$: m/z=451.1. Found: 451.0. $^1$H NMR (DMSO-d$_6$, 400 MHz) δ 7.84 (1H, s), 7.70 (1H, m), 7.62 (1H, m), 7.45 (2H, m), 7.39 (2H, m), 7.15 (2H, m), 6.97 (1H, m), 5.34 (1H, m), 1.59 (3H, m) ppm.

Example 6

N-{1-[3-Chloro-1-(3-fluorophenyl)-1H-pyrrolo[2,3-b]pyridin-2-yl]ethyl}-9H-purin-6-amine bis(trifluoroacetate)

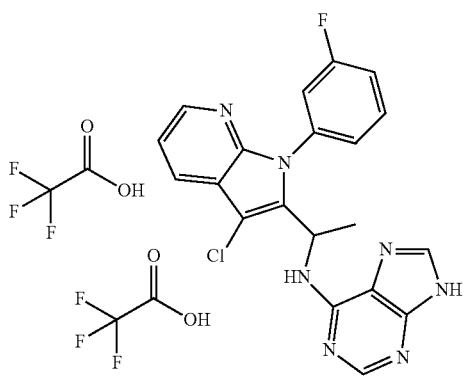

Step 1. N-Methoxy-N-methyl-1H-pyrrolo[2,3-b]pyridine-2-carboxamide

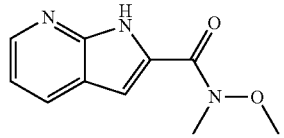

A mixture of 1H-pyrrolo[2,3-b]pyridine-2-carboxylic acid (from MolBridge, 1.0 g, 6.2 mmol), O-(benzotriazol-1-yl)-N,N,N',N'-tetramethyluronium hexafluorophosphate (3.0 g, 8.0 mmol) and triethylamine (4.3 mL, 31 mmol) in N,N-dimethylformamide (10 mL) was stirred at room temperature for 10 minutes. N,O-dimethylhydroxylamine hydrochloride (0.78 g, 8.0 mmol) was added and the resulting suspension was stirred at room temperature overnight. The mixture was quenched with water and extracted with EtOAc. The combined organic layers were dried over MgSO$_4$, concentrated, and purified on silica gel (eluting with 0-65% EtOAc/hexane) to give the desired product (1.0 g, 79%). LCMS calculated for C$_{10}$H$_{12}$N$_3$O$_2$(M+H)$^+$: m/z=206.1. Found: 206.1.

Step 2. 1-(3-Fluorophenyl)-N-methoxy-N-methyl-1H-pyrrolo[2,3-b]pyridine-2-carboxamide

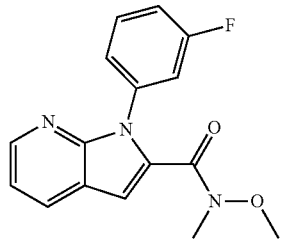 [SMILES: CON(C)C(=O)c1cc2cccnc2n1-c1cccc(F)c1]

Activated molecular sieves (3.8 g) 4 Å were placed in an oven dried flask and cooled to room temperature under nitrogen. To the flask was charged with N-methoxy-N-methyl-1H-pyrrolo[2,3-b]pyridine-2-carboxamide (0.29 g, 1.4 mmol), (3-fluorophenyl)boronic acid (0.59 g, 4.2 mmol), cupric acetate (0.38 g, 2.1 mmol), methylene chloride (35 mL) and then pyridine (0.46 mL, 5.6 mmol). The reaction mixture was stirred at room temperature overnight. The mixture was filtered through a pad of Celite. The filtrate was concentrated and purified on silica gel (eluting with 0-50% EtOAc/hexane followed by 0-5% MeOH/dichloromethane) to give the desired product (0.35 g, 83%). LCMS calculated for C$_{16}$H$_{15}$FN$_3$O$_2$(M+H)$^+$: m/z=300.1. Found: 300.0.

Step 3. 1-[1-(3-Fluorophenyl)-1H-pyrrolo[2,3-b]pyridin-2-yl]ethanone

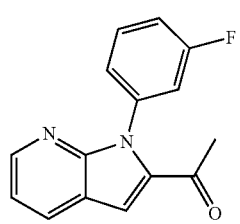 [SMILES: CC(=O)c1cc2cccnc2n1-c1cccc(F)c1]

To a mixture of 1-(3-fluorophenyl)-N-methoxy-N-methyl-1H-pyrrolo[2,3-b]pyridine-2-carboxamide (0.35 g, 1.2 mmol) in tetrahydrofuran (10 mL) was added 3.0 M methylmagnesium bromide in ether (3.1 mL, 9.4 mmol). The reaction was stirred at room temperature overnight. The reaction was quenched with saturated NH$_4$Cl solution and then extracted with EtOAc. The combined organic layers were washed with water and brine, dried over MgSO$_4$ and concentrated to give the desired product (0.24 g, 81%). The crude product was used directly in next step. LCMS calculated for C$_{15}$H$_{12}$FN$_2$O(M+H)$^+$: m/z=255.1. Found: 255.1.

Step 4. 1-[1-(3-Fluorophenyl)-1H-pyrrolo[2,3-b]pyridin-2-yl]ethanamine

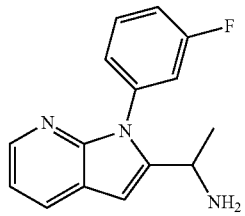 [SMILES: CC(N)c1cc2cccnc2n1-c1cccc(F)c1]

A mixture of 1-[1-(3-fluorophenyl)-1H-pyrrolo[2,3-b]pyridin-2-yl]ethanone (0.24 g, 0.94 mmol) and ammonium acetate (0.73 g, 9.5 mmol) in methanol (3.0 mL) and acetonitrile (3.0 mL) was heated at 65° C. in a sealed tube for 1 hour. After cooling to room temperature, sodium cyanoborohydride (0.18 g, 2.8 mmol) was added to the resultant mixture. The reaction was heated at 65° C. overnight. The reaction was then cooled to room temperature and quenched with saturated NaHCO$_3$ solution and then extracted with dichloromethane. The combined organic layers were dried over MgSO$_4$ and concentrated to give the crude amine (0.32 g), which was used directly in the next step. LCMS calculated for C$_{15}$H$_{15}$FN$_3$(M+H)$^+$: m/z=256.1. Found: 256.1.

Step 5. tert-Butyl {1-[1-(3-fluorophenyl)-1H-pyrrolo[2,3-b]pyridin-2-yl]ethyl}carbamate

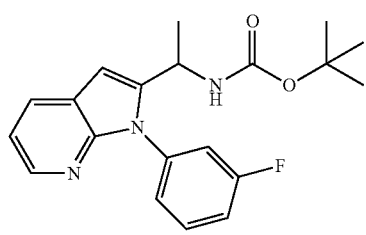 [SMILES: CC(NC(=O)OC(C)(C)C)c1cc2cccnc2n1-c1cccc(F)c1]

Di-tert-butyldicarbonate (0.82 g, 3.8 mmol) was added to a mixture of 1-[1-(3-fluorophenyl)-1H-pyrrolo[2,3-b]pyridin-2-yl]ethanamine (0.24 g, 0.94 mmol) and triethylamine (1.0 mL, 7.5 mmol) in tetrahydrofuran (8 mL). After 30 minutes, the mixture was quenched with saturated NaHCO$_3$ solution and then extracted with EtOAc. The combined organic layers were washed with brine, dried over MgSO$_4$, concentrated and purified on silica gel (eluting with 0-5% MeOH/dichloromethane) to give the desired product (0.16 g, 48%). LCMS calculated for C$_{20}$H$_{23}$FN$_3$O$_2$(M+H)$^+$: m/z=356.2. Found: 356.1.

Step 6. tert-Butyl {1-[3-chloro-1-(3-fluorophenyl)-1H-pyrrolo[2,3-b]pyridin-2-yl]ethyl}carbamate

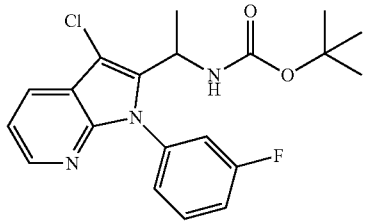 [SMILES: CC(NC(=O)OC(C)(C)C)c1c(Cl)c2cccnc2n1-c1cccc(F)c1]

A solution of N-chlorosuccinimide (24 mg, 0.18 mmol) in DMF (0.1 mL) was added dropwise to an ice-cooled solution of tert-butyl {1-[1-(3-fluorophenyl)-1H-pyrrolo[2,3-b]pyridin-2-yl]ethyl}carbamate (60 mg, 0.17 mmol) (5073-171) in N,N-dimethylformamide (1 mL). The resulting mixture was allowed to warm to room temperature and stirred overnight. The mix was diluted with water and extracted with EtOAc. The combined organic layers were dried over MgSO$_4$, concentrated, and purified on silica gel (eluting with 0-10% EtOAc/hexane) to give the desired product (26 mg, 40%). LCMS calculated for C$_{20}$H$_{22}$ClFN$_3$O$_2$(M+H)$^+$: m/z=390.1. Found: 390.1.

Step 7. 1-[3-Chloro-1-(3-fluorophenyl)-1H-pyrrolo[2,3-b]pyridin-2-yl]ethanamine

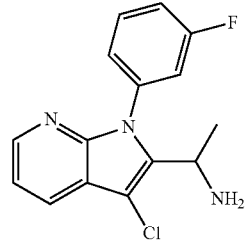 [SMILES: CC(N)c1c(Cl)c2cccnc2n1-c1cccc(F)c1]

4.0 M Hydrogen chloride in 1,4-dioxane (1.0 mL, 4.0 mmol) was added to a solution of tert-butyl {1-[3-chloro-1-(3-fluorophenyl)-1H-pyrrolo[2,3-b]pyridin-2-yl]ethyl}carbamate (26 mg, 0.067 mmol) in 1,4-dioxane (1.0 mL). The reaction was stirred at room temperature overnight. The mixture was then partitioned between EtOAc and water. The aqueous layer was adjusted to pH 9 with saturated NaHCO$_3$ solution and then extracted with EtOAc. The combined organic layers were dried over MgSO$_4$ and concentrated to give the desired amine (7 mg, 40%). LCMS calculated for C$_{15}$H$_{14}$ClFN$_3$(M+H)$^+$: m/z=290.1. Found: 290.0.

Step 8. N-{1-[3-Chloro-1-(3-fluorophenyl)-1H-pyrrolo[2,3-b]pyridin-2-yl]ethyl}-9H-purin-6-amine tris(trifluoroacetate)

A mixture of 1-[3-chloro-1-(3-fluorophenyl)-1H-pyrrolo[2,3-b]pyridin-2-yl]ethanamine (7.0 mg, 0.024 mmol), 6-bromo-9H-purine (7.2 mg, 0.036 mmol) and N,N-diisopropylethylamine (0.013 mL, 0.072 mmol) in ethanol (0.6 mL) was heated at 110° C. overnight. The mixture was filtered and the filtrate was purified on preparative-LCMS (XBridge C18 column, 19×100 mm, 5 μM; eluting with a gradient of acetonitrile/water containing 01.% TFA; at flow rate 30 mL/min; with injection volume of 2 mL) to give the desired product as a his TFA salt. LCMS calculated for C$_{20}$H$_{16}$ClFN$_7$(M+H)$^+$: m/z=408.1. Found: 408.0. $^1$H NMR (DMSO-d$_6$, 400 MHz) δ 8.36 (2H, m), 8.23 (1H, m), 7.91 (1H, m), 7.59 (2H, m), 7.48 (1H, m), 7.38 (1H, m), 7.23 (1H, m), 5.27 (1H, m), 1.71 (3H, d, J=6.8 Hz) ppm. $^{19}$F NMR (DMSO-d$_6$, 376.3 MHz) for the TFA salt: δ −74.7, −112.5 ppm.

Example 7

N-(1-(1-(3-Fluorophenyl)-1H-pyrrolo[2,3-b]pyridin-2-yl)ethyl)-9H-purin-6-amine bis(2,2,2-trifluoroacetate)

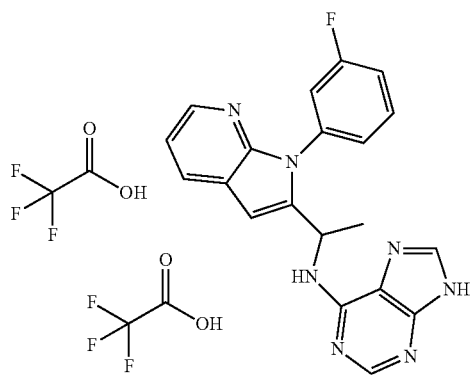

A mixture of 1-[1-(3-fluorophenyl)-1H-pyrrolo[2,3-b]pyridin-2-yl]ethanamine (24 mg, 0.094 mmol), 6-bromo-9H-purine (29 mg, 0.14 mmol) and N,N-diisopropylethylamine (0.049 mL, 0.28 mmol) in ethanol (1 mL) was heated at 110° C. overnight. The mixture was filtered and the filtrate was purified on preparative-LCMS (XBridge C18 column, 19×100 mm, 5 µM; eluting with a gradient of acetonitrile/water containing 01.% TFA; at flow rate 30 mL/min; with injection volume of 2 mL) to give the desired product as a his TFA salt. LCMS calculated for $C_{20}H_{17}FN_7(M+H)^+$: m/z=374.2. Found: 374.1. $^1H$ NMR (DMSO-$d_6$, 400 MHz) δ 9.16 (1H, br s), 8.46 (2H, m), 8.16 (1H, m), 8.04 (1H, m), 7.34 (2H, m), 7.16 (1H, m), 7.10 (1H, m), 6.79 (1H, s), 5.70 (1H, m), 1.62 (3H, d, J=6.4 Hz) ppm. $^{19}F$ NMR (DMSO-$d_6$, 376 MHz) for the TFA salt: δ −75.1, −112.8 ppm.

Example 8

N-{1-[1-(3-Fluorophenyl)-3-methyl-1H-indol-2-yl]ethyl}-9H-purin-6-amine trifluoroacetate

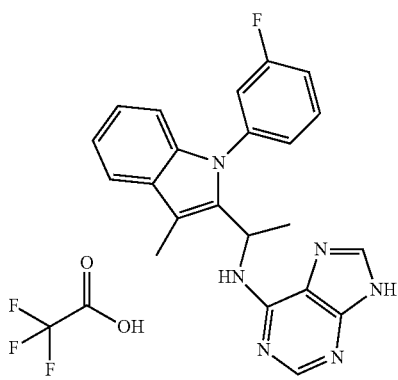 [SMILES: O=C(O)C(F)(F)F ; Cc1c(C(C)Nc2ncnc3[nH]cnc23)n(-c2cccc(F)c2)c2ccccc12]

Step 1. N-Methoxy-N,3-dimethyl-1H-indole-2-carboxamide

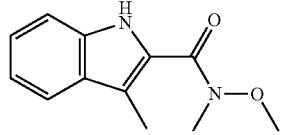 [SMILES: CON(C)C(=O)c1[nH]c2ccccc2c1C]

A mixture of 3-methyl-1H-indole-2-carboxylic acid (from Matrix Scientific, 1.0 g, 5.7 mmol), O-(benzotriazol-1-yl)-N,N,N',N'-tetramethyluronium hexafluorophosphate (4.3 g, 11 mmol) and triethylamine (4.0 mL, 28 mmol) in N,N-dimethylformamide (20 mL) was stirred at room temperature for 10 minutes. N,O-Dimethylhydroxylamine hydrochloride (0.84 g, 8.6 mmol) was added and the resulting suspension was stirred at room temperature over the weekend. The mixture was quenched with water and extracted with EtOAc. The combined organic layers were dried over MgSO$_4$, concentrated, and purified on silica gel (eluting with 0-30% EtOAc/hexane) to give the desired product (1.1 g, 88%). LCMS calculated for $C_{12}H_{15}N_2O_2(M+H)^+$: m/z=219.1. Found: 219.1.

Step 2. 1-(3-Fluorophenyl)-N-methoxy-N,3-dimethyl-1H-indole-2-carboxamide

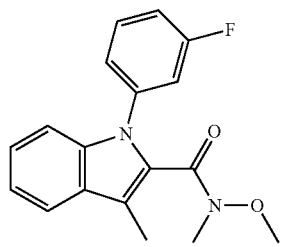 [SMILES: CON(C)C(=O)c1c(C)c2ccccc2n1-c1cccc(F)c1]

Activated molecular sieves (18 g) 4 Å were placed in an oven dried flask and cooled to room temperature under nitrogen. To the flask was charged with N-methoxy-N,3-dimethyl-1H-indole-2-carboxamide (1.5 g, 6.9 mmol), (3-fluorophenyl)boronic acid (2.9 g, 21 mmol), cupric acetate (1.9 g, 10 mmol), methylene chloride (130 mL) and pyridine (2.2 mL, 27 mmol). The reaction mixture was stirred at room temperature for 2 days. The mixture was filtered through a pad of Celite. The filtrate was concentrated and purified on silica gel (eluting with 0-30% EtOAc/hexane) to give the desired product (0.27 g, 12%). LCMS calculated for $C_{18}H_{18}FN_2O_2(M+H)^+$: m/z=313.1. Found: 313.0.

Step 3. 1-[1-(3-Fluorophenyl)-3-methyl-1H-indol-2-yl]ethanone

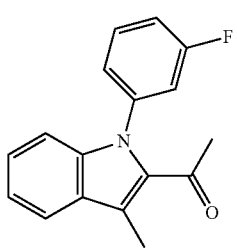 [SMILES: CC(=O)c1c(C)c2ccccc2n1-c1cccc(F)c1]

To a mixture of 1-(3-fluorophenyl)-N-methoxy-N,3-dimethyl-1H-indole-2-carboxamide (0.27 g, 0.86 mmol) in tetrahydrofuran (5 mL) was added 3.0 M methylmagnesium bromide in ether (2.3 mL, 6.9 mmol). The reaction was stirred at room temperature overnight. The reaction was quenched with saturated NH4Cl solution and extracted with EtOAc. The combined organic layers were dried over MgSO4, concentrated, and purified on silica gel (eluting with 0-15% EtOAc/hexane) to give the desired product (0.165 g, 71%). LCMS calculated for $C_{17}H_{15}FNO(M+H)^+$: m/z=268.1. Found: 268.0.

Step 4. 1-[1-(3-Fluorophenyl)-3-methyl-1H-indol-2-yl]ethanamine

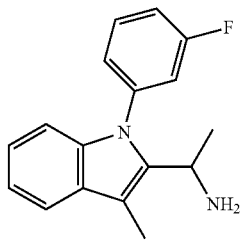 [SMILES: Cc1c(C(C)N)n(-c2cccc(F)c2)c2ccccc12]

A mixture of 1-[1-(3-fluorophenyl)-3-methyl-1H-indol-2-yl]ethanone (0.165 g, 0.617 mmol) and ammonium acetate (0.476 g, 6.17 mmol) in methanol (2.0 mL) and acetonitrile (2.0 mL) was heated at 65° C. in a sealed tube for 1 hour. After cooling to room temperature, sodium cyanoborohydride (0.12 g, 1.9 mmol) was added to the resultant mixture. The reaction was heated at 65° C. over the weekend. The reaction was cooled to room temperature and quenched with saturated NaHCO3 solution and then extracted with dichloromethane, dried over MgSO4 and concentrated to give the crude amine (0.16 g), which was used directly in next step. LCMS calculated for $C_{17}H_{18}FN_2(M+H)^+$: m/z=269.1. Found: 252.1.

Step 5. N-{1-[1-(3-Fluorophenyl)-3-methyl-1H-indol-2-yl]ethyl}-9H-purin-6-amine trifluoroacetate A mixture of 1-[1-(3-fluorophenyl)-3-methyl-1H-indol-2-yl]ethanamine (0.11 g, 0.41 mmol), 6-bromo-9H-purine (0.12 g, 0.61 mmol) and N,N-diisopropylethylamine (0.21 mL, 1.2 mmol) in ethanol (2 mL) was heated at 110° C. overnight. The mixture was purified on preparative-LCMS (XBridge C18 column, 19×100 mm, 5 μM; eluting with a gradient of acetonitrile/water containing 01.% TFA; at flow rate 30 mL/min; with injection volume of 2 mL) to give the desired product as a TFA salt. LCMS calculated for $C_{22}H_{20}FN_6(M+H)^+$: m/z=387.2. Found: 387.1. $^1H$ NMR (DMSO-$d_6$, 400 MHz) δ 8.98 (1H, br s), 8.39 (2H, m), 7.58 (1H, m), 7.49 (1H, m), 7.35 (1H, m), 7.30 (1H, m), 7.05 (2H, m), 6.88 (1H, m), 5.31 (1H, m), 2.36 (3H, s), 1.63 (3H, d, J=6.0 Hz) ppm. $^{19}F$ NMR (DMSO-$d_6$, 376 MHz) for the TFA salt: δ −74.7, −111.9 ppm.

Example 9

2-(1-(9H-Purin-6-ylamino)ethyl)-1-(3-fluorophenyl)-1H-indole-3-carbonitrile 2,2,2-trifluoroacetate

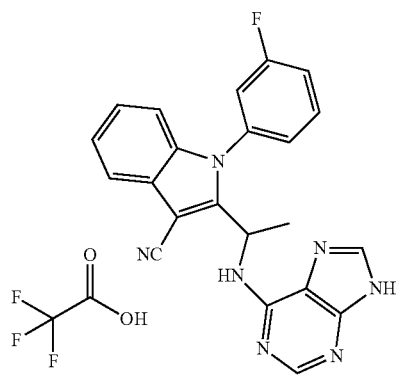 [SMILES: O=C(O)C(F)(F)F ; CC(Nc1ncnc2[nH]cnc12)c1c(C#N)c2ccccc2n1-c1cccc(F)c1]

Step 1. Methyl 3-cyano-1H-indole-2-carboxylate

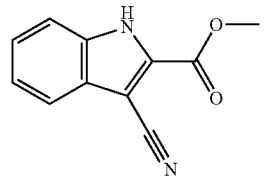

To a mixture of methyl 3-[(E)-(hydroxyimino)methyl]-1H-indole-2-carboxylate (from Key Organics, 1.0 g, 4.6 mmol) and pyridine (7.4 mL, 92 mmol) in 1,4-dioxane (20 mL) was added methanesulfonyl chloride (1.4 mL, 18 mmol). The reaction was heated at 60° C. for 2 hours. The reaction was diluted with water and extracted with EtOAc. The combined organic layers were dried over MgSO4, concentrated, and purified on silica gel (eluting with 0-5% MeOH/dichloromethane) to give the desired product (0.7 g, 76%). LCMS calculated for $C_{11}H_9N_2O_2(M+H)^+$: m/z=201.1. Found: 201.1.

Step 2. Methyl 3-cyano-1-(3-fluorophenyl)-1H-indole-2-carboxylate

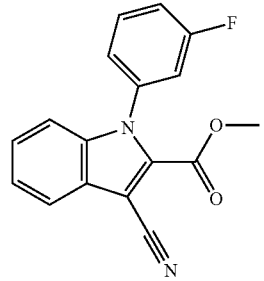 [SMILES: COC(=O)c1c(C#N)c2ccccc2n1-c1cccc(F)c1]

Activated molecular sieves (6.0 g, 27 mmol) 4 Å were placed in an oven dried flask and cooled to room temperature under nitrogen. To the flask was charged with methyl 3-cyano-1H-indole-2-carboxylate (0.45 g, 2.2 mmol), (3-fluorophenyl)boronic acid (0.94 g, 6.7 mmol), cupric acetate (0.61 g, 3.4 mmol), methylene chloride (43 mL) and pyridine (0.73 mL, 9.0 mmol). The reaction mixture was stirred at room temperature over the weekend. The mixture was filtered through a pad of Celite. The filtrate was concentrated and purified on silica gel (eluting with 0-60% EtOAc/hexane) to give the desired product (0.39 g, 59%). LCMS calculated for $C_{17}H_{12}FN_2O_2(M+H)^+$: m/z=295.1. Found: 295.0.

Step 3.
3-Cyano-1-(3-fluorophenyl)-1H-indole-2-carboxylic acid

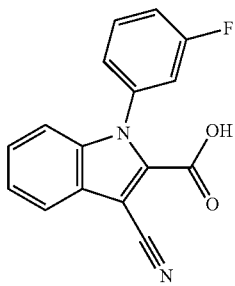 [SMILES: N#Cc1c(C(=O)O)n(-c2cccc(F)c2)c2ccccc12]

Methyl 3-cyano-1-(3-fluorophenyl)-1H-indole-2-carboxylate (0.13 g, 0.44 mmol) was treated with 1.0 M lithium hydroxide in water (0.66 mL, 0.66 mmol) in methanol (3 mL) at room temperature for 3 hours. The reaction was diluted with 1 N HCl and extracted with EtOAc. The extracts were combined, washed with brine, dried over MgSO$_4$ and concentrated to give the desired acid (0.12 g, 97%). LCMS calculated for $C_{16}H_{10}FN_2O_2(M+H)^+$: m/z=281.1. Found: 281.1.

Step 4. 3-Cyano-1-(3-fluorophenyl)-N-methoxy-N-methyl-1H-indole-2-carboxamide

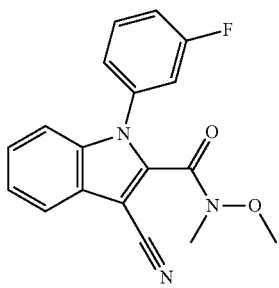 [SMILES: CON(C)C(=O)c1c(C#N)c2ccccc2n1-c1cccc(F)c1]

A mixture of 3-cyano-1-(3-fluorophenyl)-1H-indole-2-carboxylic acid (0.12 g, 0.43 mmol), O-(benzotriazol-1-yl)-N,N,N',N'-tetramethyluronium hexafluorophosphate (0.32 g, 0.86 mmol) and N,N-diisopropylethylamine (0.37 mL, 2.1 mmol) in N,N-dimethylformamide (5 mL) was stirred at room temperature for 10 minutes. N,O-Dimethylhydroxylamine hydrochloride (63 mg, 0.64 mmol) was added and the resulting suspension was stirred at room temperature overnight. The mixture was quenched with water and extracted with EtOAc. The extracts were combined, dried over MgSO$_4$, concentrated, and purified on silica gel (eluting with 0-25% EtOAc/hexane) to give the desired product (90 mg, 65%). LCMS calculated for $C_{18}H_{15}FN_3O_2(M+H)^+$: m/z=324.1. Found: 324.0.

Step 5. 2-Acetyl-1-(3-fluorophenyl)-1H-indole-3-carbonitrile

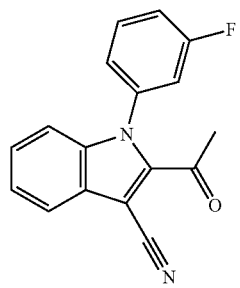 [SMILES: CC(=O)c1c(C#N)c2ccccc2n1-c1cccc(F)c1]

To a mixture of 3-cyano-1-(3-fluorophenyl)-N-methoxy-N-methyl-1H-indole-2-carboxamide (90 mg, 0.28 mmol) in tetrahydrofuran (3 mL) was added 3.0 M methylmagnesium bromide in ether (0.93 mL, 2.8 mmol). The reaction was stirred at room temperature overnight. The reaction was quenched with saturated NH$_4$Cl solution and extracted with EtOAc. The combined organic layers were dried over MgSO$_4$, concentrated, and purified on silica gel (eluting with 0-15% EtOAc/hexane) to give the desired product (43 mg, 56%). LCMS calculated for $C_{17}H_{12}FN_2O(M+H)^+$: m/z=279.1. Found: 279.0.

Step 6. 2-(1-Aminoethyl)-1-(3-fluorophenyl)-1H-indole-3-carbonitrile

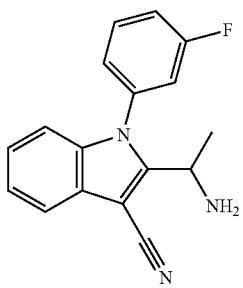 [SMILES: CC(N)c1c(C#N)c2ccccc2n1-c1cccc(F)c1]

A mixture of 2-acetyl-1-(3-fluorophenyl)-1H-indole-3-carbonitrile (43 mg, 0.15 mmol) and ammonium acetate (0.119 g, 1.54 mmol) in methanol (1.5 mL) and acetonitrile (1.5 mL) was heated at 65° C. in a sealed tube for 1 hour. After cooling to room temperature, sodium cyanoborohydride (29 mg, 0.46 mmol) was added to the resultant mixture. The reaction was heated at 65° C. overnight. The reaction was then cooled to room temperature, quenched with saturated NaHCO$_3$ solution, and extracted with dichloromethane. The combined organic layers were dried over MgSO$_4$ and concentrated to give the desired product (43 mg), which was used directly in the next step. LCMS calculated for $C_{17}H_{15}FN_3 (M+H)^+$: m/z=280.1. Found: 280.1.

Step 7. 2-(1-(9H-Purin-6-ylamino)ethyl)-1-(3-fluorophenyl)-1H-indole-3-carbonitrile 2,2,2-trifluoroacetate A mixture of 2-(1-aminoethyl)-1-(3-fluorophenyl)-1H-indole-3-carbonitrile (4.0 mg, 0.014 mmol), 6-bromo-9H-purine (4.3 mg, 0.021 mmol) and N,N-diisopropylethylamine (7.5 µL, 0.043 mmol) in ethanol (0.6 mL) was heated at 110° C. overnight. The mixture was purified on preparative-LCMS (XBridge C18 column, 19×100 mm, 5 µM; eluting with a gradient of acetonitrile/water containing 01.% TFA; at flow rate 30 mL/min; with injection volume of 2 mL) to give the desired product as a TFA salt. LCMS calculated for $C_{22}H_{17}FN_7(M+H)^+$: m/z=398.2. Found: 397.9. $^1$H NMR (DMSO-$d_6$, 400 MHz) δ 8.79 (1H, br s), 8.33 (1H, m), 8.28 (1H, m), 7.41 (1H, m), 7.38 (1H, m), 7.32 (1H, m), 7.27 (1H, m), 7.22 (2H, m), 7.11 (1H, m), 6.93 (1H, m), 5.50 (1H, m), 1.71 (3H, d, J=6.6 Hz) ppm. $^{19}$F NMR (DMSO-$d_6$, 376 MHz) for the TFA salt: δ −74.7, −112.7 ppm.

Example 10

N-(1-(3-Fluoro-1-(3-fluorophenyl)-1H-pyrrolo[2,3-b]pyridin-2-yl)ethyl)-9H-purin-6-amine bis(2,2,2-trifluoroacetate)

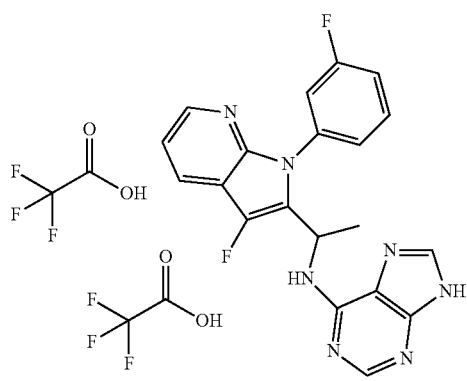

Step 1. tert-Butyl {1-[3-fluoro-1-(3-fluorophenyl)-1H-pyrrolo[2,3-b]pyridin-2-yl]ethyl}carbamate

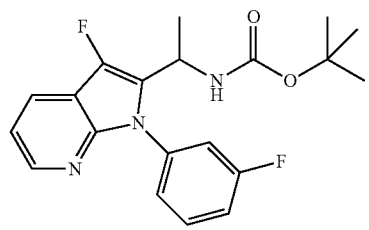 [SMILES: CC(NC(=O)OC(C)(C)C)c1c(F)c2cccnc2n1-c1cccc(F)c1]

A mixture of tert-butyl {1-[1-(3-fluorophenyl)-1H-pyrrolo[2,3-b]pyridin-2-yl]ethyl}carbamate (0.10 g, 0.28 mmol) and 1-(chloromethyl)-4-fluoro-1,4-diazoniabicyclo[2.2.2]octane ditetrafluoroborate (0.10 g, 0.28 mmol) in acetonitrile (1.5 mL, 29 mmol) and water (0.15 mL, 8.3 mmol) was heated at 50° C. overnight. The reaction was cooled and extracted with dichloromethane. The combined organic layers were dried over MgSO$_4$, concentrated and purified on silica gel (eluting with 0-20% EtOAc/hexane) to give the desired product (16 mg, 15%). LCMS calculated for $C_{20}H_{22}F_2N_3O_2(M+H)^+$: m/z=374.2. Found: 374.1.

Step 2. 1-[3-Fluoro-1-(3-fluorophenyl)-1H-pyrrolo[2,3-b]pyridin-2-yl]ethanamine

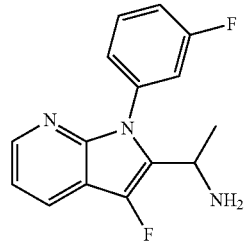 [SMILES: CC(N)c1c(F)c2cccnc2n1-c1cccc(F)c1]

To a mixture of tert-butyl {1-[3-fluoro-1-(3-fluorophenyl)-1H-pyrrolo[2,3-b]pyridin-2-yl]ethyl}carbamate (16 mg, 0.043 mmol) in methylene chloride (1 mL) was added trifluoroacetic acid (0.033 mL, 0.43 mmol). The reaction was stirred at room temperature for 1 hour. The reaction was quenched with saturated NaHCO$_3$ solution and then extracted with dichloromethane. The combined organic layers were dried over MgSO$_4$ and concentrated to give the desired amine (11 mg, 94%). LCMS calculated for $C_{15}H_{14}F_2N_3(M+H)^+$: m/z=274.1. Found: 274.1.

Step 3. N-(1-(3-Fluoro-1-(3-fluorophenyl)-1H-pyrrolo[2,3-b]pyridin-2-yl)ethyl)-9H-purin-6-amine bis(2,2,2-trifluoroacetate)

A mixture of 1-[3-fluoro-1-(3-fluorophenyl)-1H-pyrrolo[2,3-b]pyridin-2-yl]ethanamine (11 mg, 0.040 mmol), 6-bromo-9H-purine (9.6 mg, 0.048 mmol) and N,N-diisopropylethylamine (0.018 mL, 0.10 mmol) in ethanol (0.5 mL) was heated at 110° C. overnight. The mixture was purified on preparative-LCMS (XBridge C18 column, 19×100 mm, 5 µM; eluting with a gradient of acetonitrile/water containing 01.% TFA; at flow rate 30 mL/min; with injection volume of 2 mL) to give the desired product as a bis TFA salt. LCMS calculated for $C_{20}H_{16}F_2N_7(M+H)^+$: m/z=392.1. Found: 392.0.

Example A

PI3Kδ Scintillation Proximity Assay

Materials

[γ-$^{33}$P]ATP (10 mCi/mL) was purchased from Perkin-Elmer (Waltham, Mass.). Lipid kinase substrate, D-myo-Phosphatidylinositol 4,5-bisphosphate (PtdIns(4,5)P2)D (+)-sn-1,2-di-O-octanoylglyceryl, 3-O-phospho linked (PIP2), CAS 204858-53-7, was purchased from Echelon Biosciences (Salt Lake City, Utah). PI3Kδ (p110δ/p85α) was purchased from Millipore (Bedford, Mass.). ATP, MgCl$_2$, DTT, EDTA, MOPS and CHAPS were purchased from Sigma-Aldrich (St. Louis, Mo.). Wheat Germ Agglutinin (WGA) YSi SPA Scintillation Beads was purchased from GE healthcare life sciences (Piscataway, N.J.).

The kinase reaction was conducted in polystyrene 384-well matrix white plate from Thermo Fisher Scientific in a final volume of 25 µL. Inhibitors were first diluted serially in DMSO and added to the plate wells before the addition of other reaction components. The final concentration of DMSO in the assay was 0.5%. The PI3K assays were carried out at room temperature in 20 mM MOPS, pH 6.7, 10 mM MgCl$_2$, 5 mM DTT and CHAPS 0.03%. Reactions were initiated by the addition of ATP, the final reaction mixture consisted of 20 μM PIP2, 20 μM ATP, 0.2 μCi [γ-$^{33}$P] ATP, 4 nM PI3Kδ. Reactions were incubated for 210 min and terminated by the addition of 40 μL SPA beads suspended in quench buffer: 150 mM potassium phosphate pH 8.0, 20% glycerol. 25 mM EDTA, 400 μM ATP. The final concentration of SPA beads was 1.0 mg/mL After the plate sealing, plates were shaken overnight at room temperature and centrifuged at 1800 rpm for 10 minutes, the radioactivity of the product was determined by scintillation counting on Topcount (Perkin-Elmer). IC$_{50}$ determination was performed by fitting the curve of percent control activity versus the log of the inhibitor concentration using the GraphPad Prism 3.0 software. See Table 1 for data related to compounds of the invention (TFA salts of racemates of each of the compounds were tested).

TABLE 1

| Example | PI3Kδ IC$_{50}$ (nM)* |
|---|---|
| 1 | +++ |
| 2 | + |
| 3 | + |
| 4 | ++ |
| 5 | ++ |
| 6 | + |
| 7 | ++++ |
| 8 | + |
| 9 | + |
| 10 | +++ |

*50 nM or less (+); >50 nM to 100 nM (++); >100 nM to 250 nM (+++); >250 nM to 750 nM (++++); and >1000 nM (+++++)

Example B

B Cell Proliferation Assay

To acquire B cells, human PBMC are isolated from the peripheral blood of normal, drug free donors by standard density gradient centrifugation on Ficoll-Hypague (GE Healthcare, Piscataway, N.J.) and incubated with anti-CD19 microbeads (Miltenyi Biotech, Auburn, Calif.). The B cells are then purified by positive immunosorting using an autoMacs (Miltenyi Biotech) according to the manufacture's instruction.

The purified B cells (2×10$^5$/well/200 μL) are cultured in 96-well ultra-low binding plates (Corning, Corning, N.Y.) in RPMI1640, 10% FBS and goat F(ab')2 anti-human IgM (10 μg/ml) (Invitrogen, Carlsbad, Calif.), in the presence of different amount of test compounds, for three days. [$^3$H]-thymidine (1 μCi/well) (PerkinElmer, Boston, Mass.) in PBS is then added to the B cell cultures for an additional 12 hours before the incorporated radioactivity are separated by filtration with water through GF/B filters (Packard Bioscience, Meriden, Conn.) and measured by liquid scintillation counting with a TopCount (Packard Bioscience).

Example C

Pfeiffer Cell Proliferation Assay

Pfeiffer cell line (diffuse large B cell lymphoma) is purchased from ATCC (Manassas, Va.) and maintained in the culture medium recommended (RPMI and 10% FBS). To measure the anti-proliferation activity of the PI3Kδ submittals, the Pfeiffer cells are plated with the culture medium (2×10$^3$ cells/well/per 200 μl) into 96-well ultra-low binding plates (Corning, Corning, N.Y.), in the presence or absence of a concentration range of test compounds. After 3-4 days, [$^3$H]-thymidine (1 μCi/well) (PerkinElmer, Boston, Mass.) in PBS is then added to the cell culture for an additional 12 hrs before the incorporated radioactivity was separated by filtration with water through GF/B filters (Packard Bioscience, Meridenj, Conn.) and measured by liquid scintillation counting with a TopCount (Packard Bioscience).

Example D

Akt Phosphorylation Assay

Ramos cells (B lymphocyte from Burkitts lymphoma) are obtained from ATCC (Manassas, Va.) and maintained in RPMI1640 and 10% FBS. The cells (3×10$^7$ cells/tube/3 mL in RPMI) are incubated with different amounts of test compounds for 2 hours at 37° C. and then stimulated with goat F(ab')2 anti-human IgM (5 μg/mL) (Invitrogen) for 17 minutes. in a 37° C. water bath. The stimulated cells are spun down at 4° C. with centrifugation and whole cell extracts are prepared using 300 μL lysis buffer (Cell Signaling Technology, Danvers, Mass.). The resulting lysates are sonicated and supernatants are collected. The phosphorylation level of Akt in the supernatants are analyzed by using PathScan phospho-Akt1 (Ser473) sandwich ELISA kits (Cell Signaling Technology) according to the manufacture's instruction.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:
1. A compound of Formula IIa or IIIa:

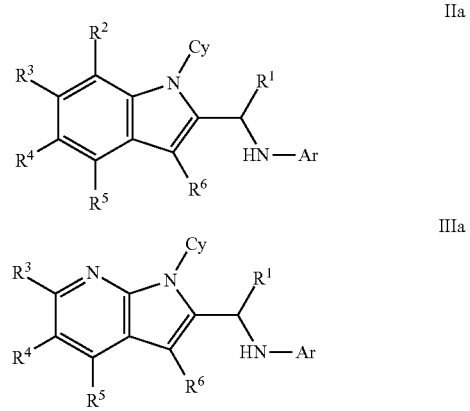

or a pharmaceutically acceptable salt thereof; wherein:
Cy is heterocycloalkyl, aryl or heteroaryl, each of which is optionally substituted with 1, 2, 3, 4, or 5 independently selected R$^C$ groups;
each R$^C$ is independently selected from halo, C$_{1-6}$ alkyl, C$_{2-6}$ alkenyl, C$_{2-6}$ alkynyl, C$_{1-6}$ haloalkyl, CN, NO$_2$, OR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, S(O)R$^b$, S(O)NR$^c$R$^d$, S(O)$_2$R$^b$, and S(O)$_2$NR$^c$R$^d$; wherein said C$_{1-6}$ alkyl is optionally substituted with 1, 2, 3, 4, or 5 substituents independently selected from hydroxy, $C_{1-6}$ alkoxy, and $C_{1-6}$ haloalkoxy;

Ar is a moiety of formula:

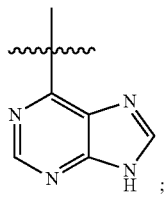

$R^1$ is $C_{1-6}$ alkyl;

$R^2$, $R^3$, $R^4$, and $R^5$ are each independently selected from H, halo, CN, $C_{1-6}$ alkyl, $C_{1-6}$ haloalkyl, $C_{1-6}$ alkoxy, and $C_{1-6}$ haloalkoxy;

$R^6$ is H, CN, halo, or $C_{1-6}$ alkyl;

each $R^a$, $R^c$, and $R^d$ is independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{1-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from OH, $NO_2$, CN, halo, $C_{1-6}$ alkyl, $C_{2-6}$ alkenyl, $C_{2-6}$ alkynyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and each $R^b$ is independently selected from $C_{1-6}$ alkyl, $C_{1-6}$ alkenyl, $C_{1-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ alkenyl, $C_{1-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from OH, $NO_2$, CN, halo, $C_{1-6}$ alkyl, $C_{2-6}$ alkenyl, $C_{2-6}$ alkynyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

or any $R^c$ and $R^d$ together with the N atom to which they are attached form a 4-, 5-, 6-, or 7-membered heterocycloalkyl group or a heteroaryl group, each optionally substituted with 1, 2, or 3 substituents independently selected from OH, $NO_2$, CN, halo, $C_{1-6}$ alkyl, $C_{2-6}$ alkenyl, $C_{2-6}$ alkynyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

2. The compound of claim 1, or a pharmaceutically acceptable salt thereof, wherein Cy is aryl, optionally substituted with 1, 2, 3, 4, or 5 independently selected $R^C$ groups.

3. The compound of claim 1, or a pharmaceutically acceptable salt thereof, wherein Cy is a phenyl ring, which is optionally substituted with 1, 2, 3, 4, or 5 independently selected $R^C$ groups.

4. The compound of claim 1, or a pharmaceutically acceptable salt thereof, wherein each $R^C$ is independently halo.

5. The compound of claim 1, or a pharmaceutically acceptable salt thereof, wherein $R^1$ is methyl.

6. A compound of claim 1, or a pharmaceutically acceptable salt thereof, wherein:

Cy is aryl, optionally substituted with 1, 2, 3, 4, or 5 independently selected $R^C$ groups;

each $R^C$ is independently selected from halo;

Ar is a moiety of formula:

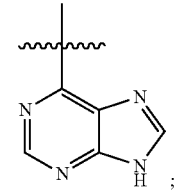

$R^1$ is $C_{1-6}$ alkyl;

$R^2$, $R^3$, $R^4$, and $R^5$ are each independently selected from H, halo, CN, $C_{1-6}$ alkyl, and $C_{1-6}$ haloalkyl;

and $R^6$ is selected from H, halo, CN, and $C_{1-6}$ alkyl.

7. The compound of claim 1, having Formula IIa:

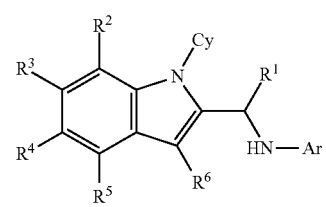

IIa or a pharmaceutically acceptable salt thereof.

8. The compound of claim 1, having Formula IIIa:

![Formula IIIa structure]

or a pharmaceutically acceptable salt thereof.

9. The compound according to claim 1, selected from:

N-{1-[6-chloro-1-(3-fluorophenyl)-1H-indol-2-yl]ethyl}-9H-purin-6-amine;

N-{1-[4-chloro-1-(3-fluorophenyl)-1H-indol-2-yl]ethyl}-9H-purin-6-amine;

N-{1-[3-chloro-1-(3-fluorophenyl)-1H-indol-2-yl]ethyl}-9H-purin-6-amine;

N-{1-[3,4-dichloro-1-(3-fluorophenyl)-1H-indol-2-yl]ethyl}-9H-purin-6-amine;

N-{1-[3-bromo-1-(3-fluorophenyl)-1H-indol-2-yl]ethyl}-9H-purin-6-amine;

N-{1-[3-chloro-1-(3-fluorophenyl)-1H-pyrrolo[2,3-b]pyridin-2-yl]ethyl}-9H-purin-6-amine;

N-(1-(1-(3-fluorophenyl)-1H-pyrrolo[2,3-b)]pyridin-2-yl)ethyl)-9H-purin-6-amine;

N-{1-[1-(3-fluorophenyl)-3-methyl-1H-indol-2-yl]ethyl}-9H-purin-6-amine;

2-(1-(9H-purin-6-ylamino)ethyl)-1-(3-fluorophenyl)-1H-indole-3-carbonitrile; and N-(1-(3-fluoro-1-(3-fluorophenyl)-1H-pyrrolo[2,3-b)]pyridin-2-yl)ethyl)-9H-purin-6-amine;

or a pharmaceutically acceptable salt of any of the aforementioned.

10. A composition comprising a compound according to claim 1, or a pharmaceutically acceptable salt thereof, and at least one pharmaceutically acceptable carrier.

11. A method of inhibiting an activity of a PI3δ kinase, comprising contacting the kinase with a compound of claim 1, or a pharmaceutically acceptable salt thereof.

12. The compound of claim 6, having Formula IIa:

![Formula IIa structure]

or a pharmaceutically acceptable salt thereof.

13. The compound of claim 6, having Formula IIIa:

![Formula IIIa structure]

or a pharmaceutically acceptable salt thereof.

14. A method of treating rheumatoid arthritis in a patient, comprising administering to said patient a therapeutically effective amount of a compound of claim 1, or a pharmaceutically acceptable salt thereof, wherein said treating refers to inhibiting or ameliorating.

15. A method of treating acute myeloblastic leukemia in a patient, comprising administering to said patient a therapeutically effective amount of a compound of claim 1, or a pharmaceutically acceptable salt thereof, wherein said treating refers to inhibiting or ameliorating.

16. A method of treating B cell lymphoma in a patient, comprising administering to said patient a therapeutically effective amount of a compound of claim 1, or a pharmaceutically acceptable salt thereof, wherein said treating refers to inhibiting or ameliorating.

17. A method of treating chronic myeloid leukemia in a patient, comprising administering to said patient a therapeutically effective amount of a compound of claim 1, or a pharmaceutically acceptable salt thereof, wherein said treating refers to inhibiting or ameliorating.

18. A method of treating diffuse large B cell lymphoma in a patient, comprising administering to said patient a therapeutically effective amount of a compound of claim 1, or a pharmaceutically acceptable salt thereof, wherein said treating refers to inhibiting or ameliorating.

* * * * *

UNITED STATES PATENT AND TRADEMARK OFFICE
CERTIFICATE OF CORRECTION

PATENT NO.        : 9,062,055 B2
APPLICATION NO.   : 13/165187
DATED             : June 23, 2015
INVENTOR(S)       : Yun-Long Li and Andrew P. Combs Page 1 of 1

It is certified that error appears in the above-identified patent and that said Letters Patent is hereby corrected as shown below:

Claims

Col. 67, Line 27, in Claim 1, delete "alkenyl, $C_{1-6}$" and insert -- alkenyl, $C_{2-6}$- --

Col. 67, Line 46-47, in Claim 1, delete "$C_{1-6}$ alkenyl, $C_{1-6}$" and insert -- $C_{2-6}$ alkenyl, $C_{2-6}$- --

Col. 67, Line 50, in Claim 1, delete "$C_{1-6}$ alkenyl, $C_{1-6}$" and insert -- $C_{2-6}$ alkenyl, $C_{2-6}$- --

Col. 69, Line 31, in Claim 9, delete "[2,3-b)]" and insert -- [2,3-b] --

Col. 69, Line 33, in Claim 9, delete "methyl- 1H" and insert -- [2,3-b] --

Col. 69, Line 46, in Claim 11, delete "PI3δ" and insert -- PI3Kδ --

Signed and Sealed this
First Day of March, 2016

Michelle K. Lee
*Director of the United States Patent and Trademark Office*